(12) United States Patent
Rother et al.

(10) Patent No.: US 7,393,648 B2
(45) Date of Patent: Jul. 1, 2008

(54) HYBRID ANTIBODIES

(75) Inventors: Russell Rother, Prospect, CT (US); Dayang Wu, Cheshire, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 462 days.

(21) Appl. No.: 10/453,698

(22) Filed: Jun. 3, 2003

(65) Prior Publication Data
US 2004/0038308 A1 Feb. 26, 2004

Related U.S. Application Data

(63) Continuation-in-part of application No. 10/308,817, filed on Dec. 3, 2002.

(60) Provisional application No. 60/336,591, filed on Dec. 3, 2001.

(51) Int. Cl.
*C12P 21/08* (2006.01)
*C07H 21/04* (2006.01)
*G01N 33/53* (2006.01)
*C12N 5/06* (2006.01)
*C12P 21/06* (2006.01)

(52) U.S. Cl. .................. 435/7.1; 530/387.3; 536/23.53
(58) Field of Classification Search .................. 435/7.1; 530/387.3; 536/23.53
See application file for complete search history.

(56) References Cited

U.S. PATENT DOCUMENTS

| | | | |
|---|---|---|---|
| 4,470,925 A | 9/1984 | Auditore-Hargreaves | |
| 5,530,101 A | 6/1996 | Queen et al. | |
| 5,585,089 A | 12/1996 | Queen et al. | |
| 5,908,925 A * | 6/1999 | Cohen et al. | 536/23.53 |
| 6,254,868 B1 | 7/2001 | Leung et al. | |
| 2002/0177170 A1 | 11/2002 | Luo et al. | |
| 2003/0040606 A1* | 2/2003 | Leung | 530/387.3 |
| 2003/0109680 A1 | 6/2003 | Wong et al. | |
| 2003/0190705 A1* | 10/2003 | Wong et al. | 435/69.1 |

FOREIGN PATENT DOCUMENTS

| | | |
|---|---|---|
| EP | 0939127 A3 | 9/1999 |
| WO | WO03/002607 A1 | 1/2003 |
| WO | WO03/025019 A1 | 3/2003 |

OTHER PUBLICATIONS

Rudikoff et al (Proc. Natl. Acad. Sci. USA 79:1979 (1982).*
Rosok et al. J. Biol. Biochem. 271:22611-22618 (1996).*
Harris et al., Prot. Sci. 4:306-310 (1995)*
"Humanization of Immu31, an α-Fetoprotein-specific Antibody", Qu et al., *Clinical Cancer Reasearch, The American Association For Cancer Research, US*, vol. 5, No. 10, pp.3095S-3100S (1999).
"Construction and Characterization of a Humanized, Internalizing, B-Cell (CD22)-Specific, Leukemia/Lymphoma Antibody, LL2", Leung et al., *Molecular Immunology*, vol. 31, pp. 17-18 (1995).
Takeda S., *Nature*, Apr. 4-10, 1985; 314 (6010):452-4, "Construction of Chimaeric Processed Immunoglobulin Genes Containing Mouse Variable and Human Constant Region Sequence".
Jones PT., *Nature*, May 29-June 4, 1986; 321 (6069); 522-5, "Replacing the Complementaryity-Determining Regions in a Human Antibody With Those From a Mouse".
Sato K., *Immunol.*, Apr. 1995; 31 (5):371-81, "Humanization of a Mouse Anti-Human Interleukin-6 Receptor Antibody Comparing Two Methods For Selecting Human Framework Regions".
Chothia C.; *J. Moi Biol.*, Aug. 1987; 196 (4): 901-17, "Canonical Structures For the Hypervariable Regions of Immunoglobulins".
Foote J., *J. Moi Biol.*, Mar. 20, 1992; 224 (2) 487-99, "Antibody Framework Residues Affecting the Conformation of the Hypervariable Loops".
Santos AD., *Prog. Nucleic Acid Res. Moi Biol.* 1998; 60:164-94, "Development of More Efficacious Antibody for Medical Therapy and Diagnosis".
Rosok MJ, *J. Biol. Chem.l* Sep. 13, 1996; 271 (37): 2211-8, "A Combinatorial Library Strategy for the Rapid Humanization of Anticarcinoma BR96 Fab."
Reichmann L. et al., *Nature* 1988, 332, 323-327, "Reshaping Human Antibodies for Therapy".
Yelton et al., *The Journal of Immunology* 1995, pp. 1994-2004, "Affinity Maturation of the BR96 Anti-Carcinoma Antibody By Condo Based Mutagenesis".
vol. 272, No. 16, Issue of Apr. 18, 1997, pp. 10678-10684, "Antibody Humanization Using Momovalent Phage Display".
Baca, M. et al., "Antibody Humanization Using Monovalent Phage Display," *J. Biol. Chem.* 272(16): 10678-10684, (1997).
Benhar, I. et al., "Rapid humanization of the Fv of monoclonal antibody B3 by using framework exchange of the recombinant immunotoxin B3(Fv)-PE38," *Proc. Natl. Acad. Sci. USA 91*: 12051-12055, (Dec. 1994).
Couto, J. et al., "Anti-BA46 Monoclonal Antibody Mc3: Humanization Using a Novel Positional Consensus and *in Vivo* and *in Vitro* Characterization," *Cancer Res.* 55:1717-1722, (Apr. 15, 1995).
Leung, S-O, et al., "Construction and Characterization of a Humanized, Internalizing, B-Cell (CD22)-Specific Leukemia/Lymphoma Antibody, LL2," *Mol. Immunol.* 32(17/18): 1413-1427, (1995).

(Continued)

*Primary Examiner*—Larry Helms
*Assistant Examiner*—Lynn Bristol
(74) *Attorney, Agent, or Firm*—Ropes & Gray LLP

(57) ABSTRACT

Hybrid antibodies and/or hybrid antibody fragments and methods of making them are provided. In one embodiment the hybrid antibodies and/or hybrid antibody fragments contain heavy and/or light variable regions that contain two or more framework regions derived from at least two antibodies. In another embodiment, at least two of the framework regions are classified in the same germline gene family. In one embodiment, at least two framework regions are classified in the same germline gene family member. The hybrid antibodies or hybrid antibody fragments may contain human framework regions and nonhuman CDRs.

15 Claims, 22 Drawing Sheets

OTHER PUBLICATIONS

Radar, C. et al. "A phage display approach for rapid antibody humanization: Designed combinatorial V gene libraries," *Proc. Natl. Acad. Sci. USA 95*: 8910-8915, (Jul. 1998).

Ohtomo, T. et al. "Humanization of Mouse ONS-M21 Antibody with the aid of hybrid variable regions," *Mol. Immunol.* 32(6): 407-416, (1995).

Rosok et al., "A Combinatorial Library Stategy for the Rapid Humanization of Anticarcinoma BR96 Fab," Journal of Biological Chemistry, 271(37):22611-22618, (1996).

Rudikoff et al., "Single amino acid substitution altering antigen-binding specificity," Proc. Natl. Acad. Sci. USA, 79:1979-1983, (1982).

* cited by examiner

Vκ Exon—Amino acid sequence alignment

| L1-L2-L3 | Locus | FR1 | CDR1 (L1) | FR2 | CDR2 (L2) | FR3 | CDR3 (L3) | SEQ ID No. |
|---|---|---|---|---|---|---|---|---|
| | | 1234567890123456789 0123 | 4567890 1abcdef 234 | 567890 123456789 | 0123456 | 7890 1234567890 1234567890 12345678 | 9012345 | |
| VKI | | | | | | | | |
| 2-1-(1) | O12 | DIQMTQSPSSLSASVGDRVTITC | RASQSISS------YLN | WYQQKPGKAPKLLIY | AASSLQS | GVPSRFSGSGSGTDFTLTISSLQPEDFATYYC | QQSYSTP | 1 |
| 2-1-(1) | O2 | DIQMTQSPSSLSASVGDRVTITC | RASQSISS------YLN | WYQQKPGKAPKLLIY | AASSLQS | GVPSRFSGSGSGTDFTLTISSLQPEDFATYYC | QQSYSTP | 2 |
| 2-1-(1) | O18 | DIQMTQSPSSLSASVGDRVTITC | QASQDISN------YLN | WYQQKPGKAPKLLIY | DASNLET | GVPSRFSGSGSGTDFTFTISSLQPEDIATYYC | QQYDNLP | 3 |
| 2-1-(1) | O8 | DIQMTQSPSSLSASVGDRVTITC | QASQDISN------YLN | WYQQKPGKAPKLLIY | DASNLET | GVPSRFSGSGSGTDFTFTISSLQPEDIATYYC | QQYDNLP | 4 |
| 2-1-(U) | A20 | DIQMTQSPSSLSASVGDRVTITC | RASQGISN------YLA | WYQQKPGKAPKRLIY | AASTLQS | GVPSRFSGSGSGTDFTLTISSLQPEDVATYYC | QKYNSAP | 5 |
| 2-1-(1) | A30 | DIQMTQSPAMSASVGDRVTITC | RASQGISN------DLG | WYQQKPGKVPKHLIY | AASSLQS | GVPSRFSGSGSGTEFTLTISSLQPEDFATYYC | LQHNSYP | 6 |
| 2-1-(1) | L14 | NIQMTQSPSSLSASVGDRVTITC | RARQGISN------YLA | WFQQKPGKAPKRLIY | AASSLQS | GVPSRFSGSGSGTDFTLTISSLQPEDFATYYC | LQHNSYP | 7 |
| 2-1-(1) | L1 | DIQMTQSPSSLSASVGDRVTITC | RASQGISN------YLA | WFQQKPGKVPKLLIY | AASSLQS | GVPSRFSGSGSGTDFTLTISSLQPEDFATYYC | QQYNSYP | 8 |
| 2-1-(1) | L15 | AIQLTQSPSSLSASVGDRVTITC | RASQGISN------WLA | WYQQKPEKAPKSLIY | DASSLES | GVPSRFSGSGSGTDFTLTISSLQPEDFATYYC | QQFNSYP | 9 |
| 2-1-(1) | L4 | AIQLTQSPSSLSASVGDRVTITC | RASQGISS------ALA | WYQQKPGKAPKLLIY | DASSLES | GVPSRFSGSGSGTDFTLTISSLQPEDFATYYC | QQFNSYP | 10 |
| 2-1-(1) | L18 | DIQMTQSPSSVSASVGDRVTITC | RASQGISS------WLA | WYQQKPGKAPKLLIY | AASSLQS | GVPSRFSGSGSGTDFTLTISSLQPEDFATYYC | QQANSFP | 11 |
| 2-1-(1) | L5 | DIQMTQSPSSVSASVGDRVTITC | RASQGISS------WLA | WYQQKPGKAPKLLIY | AASTLQS | GVPSRFSGSGSGTDFTLTISSLQPEDFATYYC | QQANSFP | 12 |
| 2-1-(1) | L19 | DIQLTQSPSSFLSASVGDRVTITC | RASQGISS------YLA | WYQQKPAKAPKLFIY | YASSLQS | GVPSRFSGSGSGTDFTLTISSLQPEDFATYYC | QQLNSYP | 13 |
| 2-1-(1) | L8 | AIRMTQSPFSLSASVGDRVTITC | WASQGISS------YLA | WYQQKPGKAPELLIY | AASTLQS | GVPSRFSGSGSGTDFTLCLQSEDFATYYC | QQYSTP | 14 |
| 2-1-(1) | L23 | AIRMTQSPSSFSASTGDRVTITC | RASQGISS------YLA | WYQQKPGKAPKLLIY | AASSLQS | GVPSRFSGSGSGTDFTLTISCLQSEDFATYYC | QQYYSFP | 15 |
| 2-1-(1) | L9 | VIMMTQSPSSLLSASTGDRVTITC | RMSQGISS------YLA | WYQQKPGKAPKLLIY | AASTLQS | GVPSRFSGSGSGTDFTLTISSLQPEDFATYYC | QQYSFP | 16 |
| 2-1-(1) | L24 | AIQMTQSPSSLSASVGDRVTITC | RASQGIRN------DLG | WYQQKPGKAPELLIY | AASSLQS | GVPSRFSGSGSGTDFTLTISSLQPEDFATYYC | LQDYNP | 17 |
| 2-1-(1) | L11 | DIQMTQSPSTLSASVGDRVTITC | RASQSISS------WLA | WYQQKPGKAPKLLIY | DASSLES | GVPSRFSGSGSGTDFTLTISSLQPDDFATYYC | QQYNSYS | 18 |
| 2-1-(U) | L12 | | | | | | | 19 |
| VKII | | | | | | | | |
| 3-1-(1) | O11 | DIVMTQTPLSLPVTPGEPASISC | RSSQSLLDSDDGNTYLD | WYLQKPGQSPQLLIY | TLSYRAS | GVPDRFSGSGSGTDFTLKISRVEAEDVGVYYC | MQRIEFP | 20 |
| 3-1-(1) | O1 | DIVMTQTPLSLPVTPGEPASISC | RSSQSLLDSDDGNTYLD | WYLQKPGQSPQLLIY | TLSYRAS | GVPDRFSGSGSGTDFTLKISRVEAEDVGVYYC | MQRIEFP | 21 |
| 4-1-(1) | A17 | DVVMTQSPLSLPVTLGQPASISC | RSSQSLVYS-DGNTYLN | WFQQRPGQSPRRLIY | KVSNRDS | GVPDRFSGSGSGTDFTLKISRVEAEDVGVYYC | MQGTHWP | 22 |
| 4-1-(1) | A1 | DVVMTQSPLSLPVTLGQPASISC | RSSQSLVYS-DGNTYLN | WFQQRPGQSPRRLIY | KVSNWDS | GVPDRFSGSGSGTDFTLKISRVEAEDVGVYYC | MQGTHWP | 23 |
| 4-1-(1) | A18 | DIVMTQTPLSLSVTPGQPASISC | KSSQSLLHS-DGKTYLY | WYLQKPGQSPQLLIY | EVSSRFS | GVPDRFSGSGSGTDFTLKISRVEAEDVGVYYC | MQGIHLP | 24 |
| 4-1-(1) | A2 | DIVMTQTPLSLSVTPGQPASISC | KSSQSLLHS-DGKTYLY | WYLQKPGQSPQLLIY | EVSNRFS | GVPDRFSGSGSGTDFTLKISRVEAEDVGVYYC | MQSIQLP | 25 |
| 4-1-(1) | A19 | DIVMTQTPLSLSVTPGEPASISC | RSSQSLLHS-NGYNYLD | WYLQKPGQSPQLLIY | EVSNRFS | GVPDRFSGSGSGTDFTLKISRVEAEDVGVYYC | MQSIQLP | 26 |
| 4-1-(1) | A3 | DIVMTQTPLSLPVTPGEPASISC | RSSQSLLHS-NGYNYLD | WYLQKPGQSPQLLIY | LGSNRAS | GVPDRFSGSGSGTDFTLKISRVEAEDVGVYYC | MQALQTP | 27 |
| 4-1-(1) | A23 | DIVMTQTPLSSPVTLGQPASISC | RSSQSLVHS-DGNTYLS | WLQQRPGQPPRLLIY | KISNRFS | GVPDRFSGSGAGTDFTLKISRVEAEDVGVYYC | MQATQFP | 28 |

*FIG. 1A*

Vκ Exon—Amino acid sequence alignment

| | | FR1 | L1 CDR1 | FR2 | L2 CDR2 | FR3 | L3 CDR3 | SEQ ID No. |
|---|---|---|---|---|---|---|---|---|
| | L1-L2-L3 Locus | 1234567890123456789 0123 | 4567890 1abcdef234 | 5678901234 56789 | 0123456 | 7890123456789012345678901 2345678 | 9012345 | |
| VκIII | 6-1-(1) A27 | EIVLTQSPGTLSLSPGERATLSC | RASQSVSSS------YLA | WYQQKPGQAPRLLIY | GASSRAT | GIPDRFSGSGSGTDFTLTISRLEPEDFAVYYC | QQYGSSP | 29 |
| | 6-1-(1) A11 | EIVLTQSPATLSLSPGERATLSC | GASQSVSSS------YLA | WYQQKPGLAPRLLIY | DASSRAT | GIPDRFSGSGSGTDFTLTISRLEPEDFAVYYC | QQYGSSP | 30 |
| | 2-1-(1) L2 | EIVMTQSPATLSVSPGERATLSC | RASQSVSS-------NLA | WYQQKPGQAPRLLIY | GASTRAT | GIPARFSGSGSGTEFTLTITSSLQSEDFAVYYC | QQYNNWP | 31 |
| | 2-1-(1) L16 | EIVMTQSPATLSVSPGERATLSC | RASQSVSS-------NLA | WYQQKPGQAPRLLIY | GASTRAT | GIPARFSGSGSGTEFTLTISSLQSEDFAVYYC | QQYNNWP | 32 |
| | 2-1-(1) L6 | EIVLTQSPATLSLSPGERATLSC | RASQSVSS-------YLA | WYQQKPGQAPRLLIY | DASNRAT | GIPARFSGSGSGTDFTLTISSLEPEDFAVYYC | QQRSNWP | 33 |
| | 2-1-(1) L20 | EIVLTQSPATLSLSPGERATLSC | RASQGVSS-------YLA | WYQQKPGQAPRLLIY | DASNRAT | GIPARFSGSGSGTDFTLTISSLEPEDFAVYYC | QQRSNWH | 34 |
| | 6-1-(1) L25 | EIVMTQSPATLSLSPGERATLSC | RASQSVSSS------YLS | WYQQKPGQAPRLLIY | GASTRAT | GIPARFSGSGSGTDFTLTISSLQPEDFAVYYC | QQDYNLP | 35 |
| VκIV | 3-1-(1) B3 | DIVMTQSPDSLAVSLGERATINC | KSSQSVLYSSNNKNYLA | WYQQKPGQPPKLLIY | WASTRES | GVPDRFSGSGSGTDFTLTISSLQAEDVAVYYC | QQYYSTP | 36 |
| VκV | 2-1-(1) B2 | ETTLTQSPAFMSATPGDKVNISC | KASQDIDD-------DMN | WYQQKPGEAAIFIIQ | EATTLVP | GIPPRFSGSGYGTDFTLTINNIESEDAAYFC | LQHDNFP | 37 |
| VκVI | 2-1-(1) A26 | EIVLTQSPDFQSVTPKEKVTITC | RASQSIGS-------SLH | WYQQKPDQSPKLLIK | YASQSFS | GVPSRFSGSGSGTDFTLTINSLEAEDAATYYC | HQSSSLP | 38 |
| | 2-1-(1) A10 | EIVLTQSPDFQSVTPKEKVTITC | RASQSIGS-------SLH | WYQQKPDQSPKLLIK | YASQSFS | GVPSRFSGSGSGTDFTLTINSLEAEDAATYYC | HQSSSLP | 39 |
| | 2-1-(1) A14 | DVVMTQSPAFLSVTPGEKVTITC | QASEGIGN-------YLY | WYQQKPDQAPKLLIK | YASQSIS | GVPSRFSGSGSGTDFTFTISSLEAEDAATYYC | QQGNKHP | 40 |

FIG. 1B

VH Exon—Amino acid sequence alignment

| | Locus | H1-H2 | FR1 | CDR1 (H1) | FR2 | CDR2 (H2) | FR3 | SEQ ID No. |
|---|---|---|---|---|---|---|---|---|
| | | | 1234567890123456789012345467890 | 1ab2345 | 67890123456789 | 012abc3456789012345 | 67890123456789012abc345678901234 | |
| | | | FR1 positions 1-30 | | FR2 positions 4-9 | CDR2 5-6 | FR3 positions 7-9 | |
| VH1 | 1-02 | 1-3 | QVQLVQSGAEVKKPGASVKVSCKASGYTFT | G--YMH | WVRQAPGQGLEWMG | WINP--NSGGTNYAQKFQG | RVTMTRDTSISTAYMELSSLRLSDDTAVYYCAR | 41 |
| | 1-03 | 1-3 | QVQLVQSGAEVKKPGASVKVSCKASGYTFT | S--YAMH | WVRQAPGQRLEWMG | WINA--GNGNTKYSQKFQG | RVTITRDTSASTAYMELSSLRSEDTAVYYCAR | 42 |
| | 1-08 | 1-3 | QVQLVQSGAEVKKPGASVKVSCKASGYTFT | S--YDIN | WVRQATGQGLEWMG | WMNP--NSGNTGYAQKFQG | RVTMTRNTSISTAYMELSSLRSEDTAVYYCAR | 43 |
| | 1-18 | 1-2 | QVQLVQSGAEVKKPGASVKVSCKVSGYTFT | S--YGIS | WVRQAPGQGLEWMG | WISA--YNGNTNYAQKLQG | RVTMTTDTSTSTAYMELRSLRSDDTAVYYCAR | 44 |
| | 1-24 | 1-U | QVQLVQSGAEVKKPGASVKVSCKVSGYTLT | E--LSMH | WVRQAPGKGLEWMG | GFDP--EDGETYNAQKFQG | RVTMTEDTSTDTAYMELSSLRSEDTAVYYCAR | 45 |
| | 1-45 | 1-3 | QMQLVQSGAEVKKTGSSVKVSCKASGYTFT | Y--RYLH | WVRQAPGQALEWMG | WITP--FNGNTNYAQKFQD | RVTMTRDRSMSTAYMELSSLRSEDTAMYYCAR | 46 |
| | 1-46 | 1-3 | QVQLVQSGAEVKKPGASVKVSCKASGYTFT | S--YYMH | WVRQAPGQGLEWMG | WITP--SGGSTSYAQKFQG | RVTMTRDTSTVMELSSLRSEDTAVYYCAR | 47 |
| | 1-58 | 1-3 | QMQLVQSGPEVKKPGTSVKVSCKASGFTFT | S--SAVQ | WVRQARGQRLEWMG | WIVV--GSGNTNYAQKFQE | RVTITRDMSTSTAYMELSSLRSEDTAVYYCAA | 48 |
| | 1-69 | 1-3 | QVQLVQSGAEVKKPGSSVKVSCKASGGTFS | S--YAIS | WVRQAPGQGLEWMG | GIIP--IFGTANYAQKFQG | RVTITADESTSTAYMELSSLRSEDTAVYYCAR | 49 |
| | 1-e | 1-2 | QVQLVQSGAEVKKPGSSVKVSCKASGGTFS | S--YAIS | WVRQAPGQGLEWMG | GIIP--IFGTANYAQKFQG | RVTITADKSTSTAYMELSSLRSEDTAVYYCAR | 50 |
| | 1-f | 1-2 | EVQLVQSGAEVKKPGATVKISCKVSGYTFT | D--YYMH | WVQQAPGKGLEWMG | LVDP--EDGETYAEKFQG | RVTITADTSTDTAYMELSSLRSEDTAVYYCAT | 51 |
| VH2 | 2-05 | 3-1/2-1 | QITLKESGPTLVKPTQTLTLTCTFSGFSLS | TSGVGVG | WIRQPPGKALEWLA | LIY--WNDDKRYSPSLKS | RLJTIKDTSKNQVVLTMTNMDPVDTATYCAHR | 52 |
| | 2-26 | 3-1 | QVTLKESGPVLVKPTETLTLTCVSGFSLS | NARMGVS | WIRQPPGKALEWLA | HIF--SNDEKSYSTSLKS | RLTISKDTSKSQVVLTMTNMDPVDTATYYCARI | 53 |
| | 2-70 | 3-1 | QVTLKESGPALVKPTQLTLTLTCTFSGFSLS | TSGMRVS | WIRQPPGKALEWLA | RID--WDDDKFYSTSLKT | RLTISKDTSKNQVVLTMTNMDPVDTATYYCARI | 54 |
| VH3 | 3-07 | 1-3 | EVQLVESGGGLVQPGGSLRLSCAASGFTFS | S--YWMS | WVRQAPGKGLEWVS | NIKQ-DGSEKYYVDSVKG | RFTISRDNAKNSLYLQMNSLRAEDTAVYYCAR | 55 |
| | 3-09 | 1-3 | EVQLVESGGGLVQPGRSLRLSCAASGFTFD | D--YAMH | WVRQAPGKGLEWVS | GISW--NSGSTGYADSVKG | RFTISRDNAKNSLYLQMNSLRAEDTALYLYCAKD | 56 |
| | 3-11 | 1-3 | EVQLVESGGGLVQPGGSLRLSCAASGFTFS | D--YYMS | WIRQAPGKGLEWVS | YISS--SGSTIYYADSVKG | RFTISRDNAKNSLYLQMNSLRAGDTAVYYCAR | 57 |
| | 3-13 | 1-3 | EVQLVESGGGLVQPGGSLRLSCAASGFTFS | D--YDMH | WVRQATGKGLEWVS | AIG--TAGDTYPGSVKG | RFTISRENAKNSLYLQMNSLRAEDTALYYCAR | 58 |
| | 3-15 | 1-U | EVQLVESGGGVVQPGRSLRLSCAASGFTFS | N--AWMS | WVRQAPGKGLEWVG | RIKSKTDGGTDYAAPVKG | RFTISRDDSKNTLYLQMNSLKTEDTAVYYCTT | 59 |
| | 3-20 | 1-3 | EVQLVESGGGLVKPGGSLRLSCAASGFTFD | D--YGMS | WVRQAPGKGLEWVS | GINW--NGGSTGYADSVKG | RFTISRDNAKNSLYLQMNSLRAEDTALYHCAR | 60 |
| | 3-21 | 1-3 | EVQLIESGGGLVQPGGSLRLSCAASGFTFS | S--YSMN | WVRQAPGKGLEWVS | SISS--SSSYIYYADSVKG | RFTISRDNAKNSLYLQMNSLRAEDTAVYYCAR | 61 |
| | 3-23 | 1-3 | EVQLLESGGGLVQPGGSLRLSCAASGFTFS | S--YAMS | WVRQAPGKGLEWVS | AISG--SGGSTYYADSVKG | RFTISRDNSKNTLYLQMNSLRAEDTAVYYCAK | 62 |
| | 3-30 | 1-3 | QVQLVESGGGVVQPGRSLRLSCAASGFTFS | S--YGMH | WVRQAPGKGLEWVA | VISY--DGSNKYYADSVKG | RFTISRDNSKNTLYLQMNSLRAEDTAVYYCAK | 63 |
| | 3-30.3 | 1-3 | QVQLVESGGGVVQPGRSLRLSCAASGFTFS | S--YAMH | WVRQAPGKGLEWVA | VISY--DGSNKYYADSVKG | RFTISRDNSKNTLYLQMNSLRAEDTAVYYCAR | 64 |
| | 3-30.5 | 1-3 | QVQLVESGGGVVQPGRSLRLSCAASGFTFS | S--YGMH | WVRQAPGKGLEWVA | VISY--DGSNKYYADSVKG | RFTISRDNSKNTLYLQMNSLRAEDTAVYYCAK | 65 |
| | 3-33 | 1-3 | QVQLVESGGGVVQPGRSLRLSCAASGFTFS | S--YGMH | WVRQAPGKGLEWVA | VIWY--DGSNKYYADSVKG | RFTISRDNSKNTLYLQMNSLRAEDTAVYYCAR | 66 |

VH Exon-Amino acid sequence alignment

| H1-H2 | Locus | FR1 | CDR1 | FR2 | CDR2 | FR3 | SEQ ID No. |
|---|---|---|---|---|---|---|---|
| 1-3 | 3-43 | EVQLVESGGVVQPGGSLRLSCAASGFTFD | D--YTMH | WVRQAPGKGLEWVS | LISW---DGGSTYYADSVKG | RFTISRDNSKNSLYLQMNSLRTEDTALYYCAKD | 67 |
| 1-3 | 3-48 | EVQLVESGGGLVQPGGSLRLSCAASGFTFS | S--YSMN | WVRQAPGKGLEWVS | YISS---SSSTIYYADSVKG | RFTISRDNAKNSLYLQMNSLRDEDTAVYYCAR | 68 |
| 1-U | 3-49 | EVQLVESGGGLVQPGRSLRLSCTASGFTFG | D--YAMS | WFRQAPGKGLEWVG | FIRSKAYGGTTEYTASVKG | RFTISRDGSKSIAYLQMNSLKTEDTAVYCTR | 69 |
| 1-1 | 3-53 | EVQLVETGGGLIQPGGSLRLSCAASGFTVS | S--NYMS | WVRQAPGKGLEWVS | VIY----SGGSTYYADSVKG | RFTISRDNSKNTLYLQMNSLRAEDTAVYYCAR | 70 |
| 1-1 | 3-64 | EVQLVESGGGLVQPGGSLRLSCAASGFTFS | S--YAMH | WVRQAPGKGLEYVS | AISS---NGGSTYYANSVKG | RFTISRDNSKNTLYLQMGSLRAEDMAVYYCAR | 71 |
| 1-3 | 3-66 | EVQLVESGGGLVQPGGSLRLSCAASGFTVS | S--NYMS | WVRQAPGKGLEWVS | VIY----SGGSTYYADSVKG | RFTISRDNSKNSLYLQMNSLRAEDTAVYYCAR | 72 |
| 1-4 | 3-72 | EVQLVESGGGLVQPGGSLRLSCAASGFTFS | D--HYMD | WVRQAPGKGLEWVG | RTRNKANSYTTEYAASVKG | RFTISRDDSKNSLYLQMNSLKTEDTAVYYCTR | 73 |
| 1-4 | 3-73 | EVQLVESGGGLVKPGGSLKLSCAASGFTFS | G--SAMH | WVRQASGKGLEWVG | RIRSKANSYATAYAASVKG | RFTISRDNAKNTLYLQMNSLRAEDTAVYYCAR | 74 |
| 1-3 | 3-74 | EVQLVESGGGLVQPGGSLRLSCAASGFTFS | S--YWMH | WVRQAPGKGLVWVS | RINS---DGSSTYADSVKG | RFTISRDNAKNTLYLQMNSLRAEDTAVYYCAR | 75 |
| 1-6 | 3-d | EVQLVESRGVLVQPGGSLRLSCAASGFTVS | S--NEMS | WVRQAPGKGLEWVS | SI-----SGGSTYYADSRKG | RFTISRDNSKNTLHLQMNSLRAEDTAVYYCKK | 76 |

| VH4 | | | | | | | |
|---|---|---|---|---|---|---|---|
| 2-1/1-1 | 4-04 | QVQLQESGPGLVKPSGTLSLTCAVSGGSIS | SS--NWMS | WVRQPPGKGLEWIG | EIY----HSGSTNYNPSLKS | RVTISVDKSKNQFSLKLSSVTAADTAVYYCAR | 77 |
| | 4-28 | QVQLQESGPGLVKPSDTLSLTCAVSGYSIS | SS--NWWG | WIRQPPGKGLEWIG | YIY----YSGSTYYNPSLKS | RVTMSVDTSKNQFSLKLSSVTAVDTAVYYCAR | 78 |
| | 4-30.1 | QVQLQESGPGLVKPSQTLSLTCTVSGGSIS | SGGYYWS | WIRQHPGKGLEWIG | YIY----YSGSTYYNPSLKS | RVTISVDTSKNQFSLKLSSVTAADTAVYYCAR | 79 |
| | 4-30.2 | QVQLQESGPGLVKPSQTLSLTCTVSGGSIS | SGGVYWS | WIRQPPGKGLEWIG | YIY----HSGSTYYNPSLKS | RVTISVDTSKNQFSLKLSSVTAADTAVYYCAR | 80 |
| | 4-30.4 | QLQLQESGPGLVKPSQTLSLTCTVSGGSIS | SGDYYWS | WIRQHPGKGLEWIG | YIY----YSGSTYYNPSLKS | RVTISVDTSKNQFSLKLSSVTAADTAVYYCAR | 81 |
| | 4-31 | QVQLQESGPGLVKPSQTLSLTCTVSGGSIS | SGGYYWS | WIRQHPGKGLEWIG | YIY----YSGSTYYNPSLKS | RVTISVDTSKNQFSLKLSSVTAADTAVYYCAR | 82 |
| | 4-34 | QVQLQQWGAGLLKPSETLSLTCAVYGGSFS | G--YYWS | WIRQPPGKGLEWIG | EIN----HSGSTNYNPSLKS | RVTISVDTSKNQFSLKLSSVTAADTAVYYCAR | 83 |
| | 4-39 | QLQLQESGPGLVKPSETLSLTCTVSGGSIS | SSSYYWG | WIRQPPGKGLEWIG | SIY----YSGSTYYNPSLKS | RVTISVDTSKNQFSLKLSSVTAADTAVYYCAR | 84 |
| | 4-59 | QVQLQESGPGLVKPSETLSLTCTVSGGSIS | S--YYWS | WIRQPPGKGLEWIG | YIY----YSGSTYYNPSLKS | RVTISVDTSKNQFSLKLSSVTAADTAVYYCAR | 85 |
| | 4-61 | QVQLQESGPGLVKPSETLSLTCTVSGGSVS | SGSYYWS | WIRQPPGKGLEWIG | YIY----YSGSTNYNPSLKS | RVTISVDTSKNQFSLKLSSVTAADTAVYYCAR | 86 |
| 2-1 | 4-b | QVQLQESGPGLVQPSQTLSLTCAVSGYSIS | SG-YYWG | WIRQPPGKGLEWIG | SI-----HSGSTYYNPSLKS | RVTISVDTSKNQFSLKLSSVTAADTAVYYCAR | 87 |

| VH5 | | | | | | | |
|---|---|---|---|---|---|---|---|
| 1-2 | 5-51 | EVQLVQSGAEVKKPGESLKISCKGSGYSFT | S--YWIG | WVRQMPGKGLEWMG | IIYP--GDSDTRYSPSFQG | QVTISADKSISTAYLQWSSLKASDTAMYCAR | 88 |
| 1-2 | 5-a | EVQLVQSGAEVKKPGESLRISCKGSGYSFT | S--YWIS | WVRQMPGKGLEWMG | RIDP--SDSYTNYSPSFQG | HVTISADKSISTAYLQWSSLKASDTAMYCAR | 89 |

| VH6 | | | | | | | |
|---|---|---|---|---|---|---|---|
| 3-5 | 6-01 | QVQLQQSGPGLVKPSQTLSLTCAIGDSVS | SNSAAWN | WIRQSPSRGLEWLG | RTYYR-SKWYNDYAVSVKS | RITINPDTSKNQFSLQLNSVTPEDTAVYYCAR | 90 |

| VH6 | | | | | | | |
|---|---|---|---|---|---|---|---|
| 1-2 | 7-4.1 | QVQLVQSGSELKKPGASVKVSCKASGYTFT | S--YAMN | WVRQAPGQGLEWMG | WINT--NTGNPTYAQGFTG | RFVFSLDTSVSTAYLQICSLKAEDTAVYYCAR | 91 |

Vλ Exon—Amino acid sequence alignment

| CDR1-2 | Locus | FR1 | CDR1 | FR2 | CDR2 | FR3 | CDR3 | SEQ ID No. |
|---|---|---|---|---|---|---|---|---|
| | | 1234567890123 | 45678901abc234 | 567890123456789 | 01abcde23456 | 7890123456789012345678 | 9012345abcde | |
| Vλ1 | | | | | | | | |
| 13-7(A) | 1a | QSVLTQPPSVSEAPRQRVTISC | SGSSSNIGNN-AVN | WYQQLPGKAPKLLIY | YD-----DLLPS | GVSDRFSGSKSG--TSASLAISGLQSEDEADYYC | AAWDSLNG | 92 |
| 14-7(A) | 1e | QSVLTQPPSVSGAPGQRVTISC | TGSSSNIGAGYDVH | WYQQLPGTAPKLLIY | GN-----SNRPS | GVPDRFSGSKSG--TSASLAITGLQAEDEADYYC | QSYDSSLSG | 93 |
| 13-7(A) | 1c | QSVLTQPPSASGTPGQRVTISC | SGSSSNIGSN-TVN | WYQQLPGTAPKLLIY | SN-----NQRPS | GVPDRFSGSKSG--TSASLAISGLQSEDEADYYC | AAWDSLNG | 94 |
| 13-7(A) | 1g | QSVLTQPPSASGTPGQRVTISC | SGSSSNIGSN-YVY | WYQQLPGTAPKLLIY | RN-----NQRPS | GVPDRFSGSKSG--TSASLAISGLRSEDEADYYC | AAWDSLSG | 95 |
| 13-7(A) | 1b | QSVLTQPPSVSAAPGQKVTISC | SGSSSNIGNN-YVS | WYQQLPGTAPKLLIY | DN-----NKRPS | GIPDRFSGSKSG--TSATLGITGLQTGDEADYYC | GTWDSLSG | 96 |
| Vλ2 | | | | | | | | |
| 14-7(A) | 2c | QSALTQPPSASGSPGQSVTISC | TGTSSDVGGYNYVS | WYQQHPGKAPKLMIY | EV-----SKRPS | GVPDRFSGSKSG--NTASLTVSGLQAEDEADYYC | SSYAGSNNF | 97 |
| 14-7(A) | 2e | QSALTQPRSVSGSPGQSVTISC | TGTSSDVGGYNYVS | WYQQHPGKAPKLMIY | DV-----SKRPS | GVPDRFSGSKSG--NTASLTISGLQAEDEADYYC | CSYAGSYTF | 98 |
| 14-7(A) | 2a2 | QSALTQPASVSGSPGQSITISC | TGTSSDVGGYNYVS | WYQQHPGKAPKLMIY | EV-----SNRPS | GVSNRFSGSKSG--NTASLTISGLQAEDEADYYC | SSYTSSSTL | 99 |
| 14-7(A) | 2d | QSALTQPPSVGSPGQSVTISC | TGTSSDVGSYNRVS | WYQQPPGTAPKLMIY | EV-----SNRPS | GVPDRFSGSKSG--NTASLTISGLQAEDEADYYC | SLYTSSSTF | 100 |
| 14-7(A) | 2b2 | QSALTQPASVSGSPGQSITISC | TGTSSDVGSYNLVS | WYQQHPGKAPKLMIY | EV-----SKRPS | GVSNRFSGSKSG--NTASLTISGLQAEDEADYYC | CSYAGSSTE | 101 |
| Vλ3 | | | | | | | | |
| 11-7 | 3r | SYELTQPPSVSVSPGQTASITC | SG-DK-LGDK-YAC | WYQQKPGQSPVLVIY | QD-----SKRPS | GIPERFSGSNSG--NTATLTISGTQAMDEADYYC | QAWDSSTA | 102 |
| 11-7 | 3j | SYELTQPLSVFSVSPGQTARITC | GG-NN-IGSK-NVH | WYQQKGQAPVLVIY | RD-----SNRPS | GIPERFSGSNSG--NTATLTISRAQGDEADYYC | QVWDSSTA | 103 |
| 11-7 | 3p | SYELTQPPSVSVSPGQTARITC | SG-DA-LPKK-YAY | WYQKSGQAPVLVIY | ED-----SKRPS | GIPERFSGSSSG--TMATLTISGAQVEDEADYYC | YSTDSSGNH | 104 |
| 11-7 | 3a | SYELTQPPSVSVSLGQMARITC | SG-EA-LPKK-YAY | WYQKPGQFPVLVIY | KD-----SERPS | GIPERFSGSSSG--TIVTLTISGVQAEDEADYYC | LSADSSGTY | 105 |
| 11-7 | 3l | SSELTQDPAVSVALGQTVRITC | QG-DS-LRSY-YAS | WYQKPGQAPVLVIY | GK-----NNRPS | GIPERFSGSNSG--NTASLTITGAQAEDEADYYC | NSRDSSGNH | 106 |
| 11-7 | 3h | SYVLTQPPSVSAPGKTARITC | GG-NN-IGSK-SVH | WYQKPGQAPVLVIY | YD-----SDRPS | GIPERFSGSNSG--NTATLTISRVEAGDEADYYC | QVWDSSSDH | 107 |
| 11-7 | 3e | SYELTQLPSVSVSPGQTARITC | SG-DV-LGEN-YAD | WYQQKPGQAPELVIY | ED-----SERYP | GIPERFSGSTSG--NTTTLTISRVLTEDEADYYC | LSGDEDN | 108 |
| 11-7 | 3m | SYELMQPPSVSVSPGQTARITC | SG-DA-LPKQ-YAY | WYQQKPGQAPVLVIY | KD-----SERPS | GIPERFSGSSSG--TTVTLTISGVQAEDEADYYC | QSADSSGTY | 109 |
| 11-7 | 2-19 | SYELTQPSSVSVSPGQTARITC | SG-DV-LAKK-YAR | WFQQKPGQAPVLVIY | KD-----SERPS | GIPERFSGSSSG--TTVTLTISGAQVEDEADYYC | YSAADNN | 110 |

*FIG. 3A*

Vλ Exon—Amino acid sequence alignment

| | Locus | FR1<br>1234567891234567890123 | CDR1<br>45678901abc234 | FR2<br>5678901234567890 | CDR2<br>01abcde23456 | FR3<br>78901234567ab901234567890123456 | FR3 (cont)<br>8<br>78901234567 | CDR3<br>9<br>9012345abcde | SEQ ID No. |
|---|---|---|---|---|---|---|---|---|---|
| Vλ4 | 4c | LPVLTQPPSASALLGASIKLTC | TLSSEHSTY--TIE | WYQQRPGRSPQYIMK | VKS-DGSHSKGD | GIPDRFMGSSSG--ADRYLTFSNLQSDDEAEYHC | | GESHTIDGQVG* | 111 |
| | 4a | QPVLTQSSSASASLGSSVKLTC | TLSSGHSSY--IIA | WHQQQPGKAPRYLMK | LEG-SGSYNKGS | GVPDRFSGSSSG--ADRYLTISNLQLEDEADYYC | | ETWDSNT | 112 |
| | 4b | QLVLTQSPSASASLGASVKLTC | TLSSGHSSY--AIA | WHQQQPEKGPRYLMK | LNS-DGSHSKGD | GIPDRFSGSSSG--AERYLTISSLQSEDEADYYC | | QTWGTGI | 113 |
| Vλ5 | 5e | QPVLTQPSSSASPGESARLTC | TLPSDINVGSYNIY | WYQQKPGSPPPRYLLY | YYS-DSDKGQQS | GVPSRFSGSKDASANTGILLISGLQSDEADYYC | | MIWPSNAS | 114 |
| | 5c | QAVLTQPASLSASPGASASLTC | TLRSGINVGTYRIY | WYQQKPGSPPQYLLR | YKS-DSDKQQGS | GVPSRFSGSKDASANAGILLISGLQSDEADYYC | | MIWHSSAS | 115 |
| | 5b | QPVLTQPSSHSASSGASVRLTC | MLSSGFSVGDFWIR | WYQQKPGNPPRYLLY | YHS-DSNKGQGS | GVPSRFSGSNDASANAGILRISGLQPEDEADYYC | | GTWHSNSKT | 116 |
| Vλ6 | 6a | NFMLTQPHSVSESPGKTVTISC | TRSSGSIASN--YVQ | WYQQRPGSSPTTVIY | ED-----NQRPS | GVPDRFSGSIDSSSNSASLTISGLKTEDEADYYC | | QSYDSSN | 117 |
| Vλ7 | 7a | QTVVTQEPSLTVSPGGTVTLTC | ASSTGAVTSGYYPN | WFQKKPGQAPRALIY | ST-----SNKHS | WTPARFSGSLLG--GKAALTLSGVQPEDEAEYYC | | LLYYGGAQ | 118 |
| | 7b | QAVVTQEPSLTVSPGGTVTLTC | GSSTGAVTSGHYPY | WFQKKPGQAPRTLIY | DT-----SNKHS | WTPARFSGSLLG--GKAALTLSGAQPEDEAEYYC | | LLSYSGAR | 119 |
| Vλ8 | 8a | QTVVTQEPSFSVSPGGTVTLTC | GLSSGSVSTSYYPS | WYQQTPGQAPRTLIC | ST-----NTRSS | GVPDRFSGSILG--NKAALTITGAQADDESDYYC | | VLYMGSGI | 120 |
| Vλ9 | 9a | QPVLTQPPSASALGASVTLIC | TLSSGYSNY--KVD | WYQQRPGKGPRFVMR | VGTGGIVGSKGD | GIPDRFSVLGSG--LNRYLTIKNIQEEDESDYHC | | GADHGSGSNFV* | 121 |
| Vλ10 | 10a | QAGLTQPPSVSKGLRQTATLTC | TGNSNNVGNQ-GAA | WLQQHQGHPPKLLSY | RN-----NNRPS | GISERLSASRSG--NTASLTITGLQPEDEADYYC | | SAWDSSLSA | 122 |

FIG. 3B

Initial antibody VL protein sequence (SEQ ID NO. 123)

| DIVLTQSPATLSVTPGDSVSLSC | RASQSISNDLH | WYQQKSHESPRLLIK | YASQSIS | GIPSRFSG SGSGTDFTLSINSVETEDFGMYFC | QQSNSWPYT | FGGGTKLEIK |
|---|---|---|---|---|---|---|
| FR1 | CDR1 | FR2 | CDR2 | FR3 | CDR3 | FR4 |

FIG. 4A

Framework 1 specific rearranged antibody (SEQ ID NO. 124)
Antibody sequence GI (gene identification) number: 3747016 which belong to VkIII (either L2 or L16)

*EIVLTQSPATLSVSPGESATLSC RASQSVSSNLA WYQQKPGQAPRLLIY GASTRAT GIPARFSGSGSGTEFTLTISSLQSEDFAVYYC QQSNKWPRT FGQGTKVEIK*
78%

FIG. 4B

Framework 2 specific rearranged antibody (SEQ ID NO. 125)
Antibody sequence GI (gene identification) number: 5833827 which belong to VkIII (either L2 or L16)

*LSVSPGERVTFSC RASQTLATNFLA WYQQKSDQAPRLLIY DSSTRST GIPPRFSGTGSGTDFTLTISSLQSDDFAVYFC QQYHDMPLT FGG*
73%

FIG. 4C

Framework 3 specific rearranged antibody (SEQ ID NO. 126)
Antibody sequence GI (gene identification) number: 722614 which belong to VkIII (L6)

*ATLSLSPGEGATLSC RASQSVNTFVA WYQQKSGQAPRLLIY DASKRAA DIPSRFSGSGSGTDFTLTISSLEPEDFGVYFC QQRSYWPQI FGQGTKLEIK*
81%

FIG. 4D

Framework 4 specific rearranged antibody (SEQ ID NO. 127)
Antibody sequence GI (gene identification) number: 1785870

*MAELTQSPATLSVSPGETASLSC RASQSVSNNLA WYQQKPGQAPRLLIY AASTRAP GIAARFSGSVSGAD FTLTISRLEPEDFAAYFC QQYGRTPLLT FGGGTKLEIK*
100%

FIG. 4E hybrid antibody VL sequence (SEQ ID NO. 128)
EIVLTQSPATLSVSPGESATLSC RASQSISNDLH WYQQKSDQAPRLLIY YASQSIS DIPSRFSGSGSGTDFTLTISSLEPEDFGVYFC QQSNSWPYT FGGGTKLEIK
78%                                          73%                                              81%                           100%

*FIG. 4F*

Sequence homologies of initial, hybrid and germline VL sequences

|    | Antibody comparisons | Frameworks | CDRs | Whole VL |
|----|----------------------|------------|------|----------|
| VL | Hybrid antibody versus initial antibody sequence | (65/80)81% | (27/27)100% | (92/107)86% |
| VL | Hybrid antibody versus the most similar human germline sequences VκVI (A10/A26) | (49/70)70%* | (18/25)72%* | (67/95)71%* |
| VL | The most similar human rearranged CDR grafted VL versus initial antibody sequence | (62/80)77% | (27/27)100% | (89/107)83% |
| VL | The most similar human rearranged CDR grafted VL versus the most similar human germline sequence VκVI (A14) | (49/70)70%* | (15/25)60%* | (64/95)67%* |

*Does not include J region sequence

*FIG. 4G*

Search with complete VL of initial antibody (SEQ ID NO. 129)
Antibody sequence GI (gene identification) number: 418844 which belong to VκVI (A14)
DVLLTQSPAILSVSPGERVSFSC RASQSIGTSIH WYQQRTNGPPRLLIK YASESIS GIPSRFSGSGSGTDFTLSISSVESEDIADYYC QQTNSWPTT FGGGTKLEIK
                                                 67%                                              81%                           100%

*FIG. 4H*

Search with VL combined framework (excluding CDRs) of initial antibody (SEQ ID NO. 130)
Antibody sequence GI (gene identification) number: 418844 which belong to VκVI (A14)
DVLLTQSPAILSVSPGERVSFSC RASQSIGTSIH WYQQRTNGPPRLLIK YASQSIS GIPSRFSGSGSGTDFTLSISSVESEDIADYYC QQTNSWPTT FGGGTKLEIK
      70%                                         67%                                              81%                           100%

*FIG. 4I*

Initial antibody VH protein sequence (SEQ ID NO. 131)
VQLQESGPGLVKPSQSLSLTCTVT GYSITSDYAWN WIRQFPGNKLEWMG YISYSGSTYNPSLKS RVSITRDTSKNQFFLQLNSVTTEDTATYYCAR WESWFAY WGQGTLVTVSA
    FR1                    CDR1             FR2                CDR2                              FR3                              CDR3     FR4

FIG. 5A

Framework 1 specific rearranged antibody (SEQ ID NO. 132)
Antibody sequence GI (gene identification) number: 563649 which belong to VH4-31
VQLQESGPGLVKPSQTLSLTCTVS GGSISSGRYYWS *WVRQPAGKGLEWIG RIYSTGTTKYNSSLKS RITISVDTSKNQFSLKLSSVIPADTAVYYCAR* EVDGDYIFDY WGQGTLVTVSS
91%

FIG. 5B

Framework 2 specific rearranged antibody (SEQ ID NO. 133)
Antibody sequence GI (gene identification) number: 951263 which belong to VH4-31
VQLQQWGAGLLKPSETLSLTCAVS GGSFSVDYWS WIRQFPGKGLEWIG EINDSGSTNYKSSLKS RVTIS IDTSKNQFSLNLSAVTAADTAVYFCAR DRRVGTYNWFDP WGQGTLVTVSS
                                                                78.5%

FIG. 5C

Framework 3 specific rearranged antibody (SEQ ID NO. 134)
Antibody sequence GI (gene identification) number: 484852 which belong to VH4-4 or VH4-31
PGLVKPSQTLSLTCTVS GGSISSGSYYWN *WIRQPGGKGLEWIG RIYTSGSTNYNPSLKS* RVTISVDTSKNQFSLQLNSVTPEDTAVYYCAR QSNWFDP WGQGTLVTVSS
                                                                                               81%

FIG. 5D

Framework 4 specific rearranged antibody (SEQ ID NO. 135)
Antibody sequence GI (gene identification) number: 2367531
VQLLESGGGLVQPGGSLRLSCAAS GFTFSSYAMN WVRQAPGKGLEWVS TISGSGDNTIIYADSVRG *RFTISRDNSKNTLSLQMNISLGAEDTAVYCAK* DLVVVYDSSGYSII WGQGTLVTVSA
                                                                                                                                              100%

FIG. 5E hybrid antibody VL sequence (SEQ ID NO. 136)
VQLQESGPGLVKPSQTLSLTCTVS GYSITSDYAWN WIRQFPGKGLEWIG YISYSGSTSYNPSLKS RVTISVDTSKNQFSLQLNSVTPEDTAVYYCAR WESWFAY WGQGTLVTVSA
91%                                                78.5%                                        81%                                     100%

FIG. 5F

Sequence homologies of initial, hybrid and germline VH sequences

| | Antibody comparisons | Frameworks | CDRs | Whole VH |
|---|---|---|---|---|
| VH | Hybrid antibody versus initial antibody | (70/81)86.4% | (34/34)100% | (104/115)90% |
| VH | Hybrid antibody versus the most similar human germline sequence (VH4-31) | (65/70)92.8%* | (19/27)70%* | (84/97)86.6%* |
| VH | The most similar human rearranged CDR grafted VH versus initial antibody | (65/81)80% | (34/34)100% | (99/115)86% |
| VH | The most similar human rearranged CDR grafted VH versus the most similar human germline sequence (VH4-31) | (68/70)97%* | (19/27)70%* | (87/97)89.6%* |

*Does not include D or J region sequence

FIG. 5G

Search with complete VH of initial antibody (SEQ ID NO. 137)
Antibody sequence name: 4995411
VQLQESGPGLVKPSQTLSLTCTVS GGSISSGGYWN WIRQHPGKGLEWIG YIYYSGSTYNPSLKS RVTISVDTSKNQFSLKLSSVTAADTAVYYCAR GLKWGSNHYFDY WGQGTLVTVSS
91%                                71%                                                       69%                                  91%

FIG. 5H

Search with VH combined framework (excluding CDRs) of initial antibody (SEQ ID NO. 138)
Antibody sequence name: 1791179
VQLQESGPGLVKPSQTLSLTCTVS GGSISSGGYWS WIRQHPGKGLEWIG YIYYSASTYYKQSLKS RVFISLDTSKNQFSLKLSSVTAADTAVYYCAR GCEEYYFDH WGQGTLVTVSS
91%                                71%                                                        72%                                 91%

FIG. 5I

JH-Amino acid sequence alignment

```
                H3
              ------
             CDR3
           --------
             100        110
              |          |
JH1    ---AEYFQHWGQGTLVTVSS     (SEQ ID NO. 139)
JH2    ---YWYFDLWGRGTLVTVSS     (SEQ ID NO. 140)
JH3    -----AFDIWGQGTMVTVSS     (SEQ ID NO. 141)
JH4    -----YFDYWGQGTLVTVSS     (SEQ ID NO. 142)
JH5    ----NWFDPWGQGTLVTVSS     (SEQ ID NO. 143)
JH6    YYYYYGMDVWGQGTTVTVSS     (SEQ ID NO. 144)
```

Jk-Amino acid sequence alignment

```
           L3
           -
          CDR3
           --
           100
            |
Jk1    WTFGQGTKVEIK     (SEQ ID NO. 145)
Jk2    YTFGQGTKLEIK     (SEQ ID NO. 146)
Jk3    FTFGPGTKVDIK     (SEQ ID NO. 147)
Jk4    LTFGGGTKVEIK     (SEQ ID NO. 148)
Jk5    ITFGQGTRLEIK     (SEQ ID NO. 149)
```

Jλ-Amino acid sequence alignment

```
          CDR3
           --
           100
            |
Jλ1    YVFGTGTKVTVL     (SEQ ID NO. 150)
Jλ2    VVFGGGTKLTVL     (SEQ ID NO. 151)
Jλ3    VVFGGGTKLTVL     (SEQ ID NO. 152)
Jλ7    AVFGGGTQLTVL     (SEQ ID NO. 153)
```

*FIG. 6*

Hybrid antibody variable light chain (VL) and variable heavy chain (VH)
(Frameworks are underlined, changed amino acid and nucleotides are in bold)

VL

GAA ATT GTG CTA ACT CAG TCT CCA GCC ACC CTG TCT GTG AGT CCA GGA GAT AGC GCC
 E   I   V   L   T   Q   S   P   A   T   L   S   V   S   P   G   E   S   A

ACT CTT TCC TGC AGG GCC AGC CAA AGT ATT AGC AAC GAC CTA CAC TGG TAT CAA CAA
 T   L   S   C   R   A   S   Q   S   I   S   N   D   L   H   W   Y   Q   Q

AAA TCA GAT CAG GCT CCA AGG CTT CTC ATC TAC TAT GCT TCC CAG TCC ATC TCT GAT
 K   S   D   Q   A   P   R   L   L   I   Y   Y   A   S   Q   S   I   S   D

ATC CCC TCC CGG TTC AGT GGC AGT GGA TCA GGG ACA GAT TTC ACT CTC ACT ATC AGC
 I   P   S   R   F   S   G   S   G   S   G   T   D   F   T   L   T   I   S

AGT CTG GAG CCT GAA GAT TTT GGA GTG TAT TTC TGT CAA CAG AGT AAC AGC TGG CCG
 S   L   E   P   E   D   F   G   V   Y   F   C   Q   Q   S   N   S   W   P

TAC ACG TTC GGA GGG GGG ACC AAG CTG GAA ATA AAA     (SEQ ID NO. 154)
 Y   T   F   G   G   G   T   K   L   E   I   K      (SEQ ID NO. 155)

VH

GAT GTG CAG CCT CAG GAG TCG GGA CCT GGC CTG GTG AAA CCT TCT CAG ACT CTG TCC
 D   V   Q   L   Q   E   S   G   P   G   L   V   K   P   S   Q   T   L   S

CTC ACC TGC ACT GTC TCT GGC TAC TCA ATC ACC AGT GAT TAT GCC TGG AAC TGG ATC
 L   T   C   T   V   S   G   Y   S   I   T   S   D   Y   A   W   N   W   I

CGG CAG TTT CCA GGA AAA GGA CTG GAG TGG ATT GGC TAC ATA AGC TAC AGT GGT AGC
 R   Q   F   P   G   K   G   L   E   W   I   G   Y   I   S   Y   S   G   S

ACT AGC TAC AAC CCA TCT CTC AAA AGT CGA GTC ACT ATC TCT GTA GAC ACA TCC AAG
 T   S   Y   N   P   S   L   K   S   R   V   T   I   S   V   D   T   S   K

AAC CAG TTC TCC CTG CAG TTG AAT TCT GTG ACT CCT GAG GAC ACA GCC GTA TAT TAC
 N   Q   F   S   L   Q   L   N   S   V   T   P   E   D   T   A   V   Y   Y

TGT GCA AGA TGG GAG TCC TGG TTT GCT TAC TGG GGC CAA GGG ACT CTG GTC ACT GTC
 C   A   R   W   E   S   W   F   A   Y   W   G   Q   G   T   L   V   T   V

TCT GCA    (SEQ ID NO. 156)
 S   A     (SEQ ID NO. 157)

Oligo1 (SEQ ID NO. 158)
5'GATATACCC ATGG GAA ATT GTG CTA ACT CAG
Oligo2 (SEQ ID NO. 159)
5'GCC ACC CTG TCT GTG AGT CCA GGA GAT AGC GCC ACT CTT TCC TGC AGG
Oligo3 (SEQ ID NO. 160)
5'TAT CAA CAA AAA TCA GAT CAG GCT CCA AGG CTT CTC ATC
Oligo4 (SEQ ID NO. 161)
5'AGG CTT CTC ATC TAC TAT GCT TCC CAG TCC ATC
Oligo5 (SEQ ID NO. 162)
5'CAG TCC ATC TCT GAT ATC CCC TCC CGG
Oligo6 (SEQ ID NO. 163)
5'ACA GAT TTC ACT CTC ACT ATC AGC AGT CTG GAG CCT GAA GAT TTT
Oligo7 (SEQ ID NO. 164)
5'GAA GAT TTT GGA GTG TAT TTC TGT CAA CAG

VH

Oligo8 (SEQ ID NO. 165)
5'GGC CTG GTG AAA CCT TCT CAG ACT CTG TCC CTC ACC
Oligo9 (SEQ ID NO. 166)
5'CTC ACC TGC ACT GTC TCT GGC TAC TCA ATC ACC
Oligo10 (SEQ ID NO. 167)
5'CAG TTT CCA GGA AAA GGA CTG GAG TGG ATT GGC TAC ATA AGC
Oligo11 (SEQ ID NO. 168)
5'CCA TCT CTC AAA AGT CGA GTC ACT ATC TCT GTA GAC ACA TCC AAG
Oligo12 (SEQ ID NO. 169)
5'TCC AAG AAC CAG TTC TCC CTG CAG TTG AAT TCT
Oligo13 (SEQ ID NO. 170)
5'TTG AAT TCT GTG ACT CCT GAG GAC ACA GCC
Oligo14 (SEQ ID NO. 171)
5'GAG GAC ACA GCC GTA TAT TAC TGT GCA

*FIG. 8*

D1 light Chain

Initial antibody VL protein sequence (SEQ ID NO. 172)
*L1,L2,L3: loop regions structural criteria defined by Chothia
CDRs: CDRs are according to Kabat

```
                                    1 abcdef
1(D)    10(S)    20(S)    30(V) 32(Y)         40(P)    50(K)         60(D)    70(D)    80(A)         90(Q)         100(G) 107(K)
                         ----L1-----                   --L2--                                         --L3--
DVLMTQSPLSLPVSLGDKASASC  RSSQNIVHSNGDTYLE  WYLQRPGQSPKLLIF  KVSNRFS  GVPDRFSGSGSGTDFTLKISRVEAEDLGVYYC  FQGSHVPWT  FGGGTKLEIK
FR1                      CDR1              FR2              CDR2     FR3                              CDR3       FR4
```

Framework 1 specific rearranged antibody
Antibody sequence GI (gene identification) number: 441333 (germlinenVkII A17),
also the same % with A1 and A17 (SEQ ID NO. 173)
DVVMTQSPLSLPVTLGQSASISC TSSQSLVYTDGKIYLN WFQQRPGQSPRRLIF KVSNRDS GVPDRFSGSGSGTDFTLKISRVEAEDVAIYYC MQGTHWPGT FGQGTKVEIKR
82%

Antibody sequence GI (gene identification) number: 5578780 (germline VkII A3 or A19), (SEQ ID NO. 174)
DVVMTQSPLSLPVTPGEPASISC RSSQSLLHSNGYNYFA WYLQKPGQSPQLLV YLGSNRAS GSGTDFTLKISRVEAEDVGIYYC MQVLQTPYT FGQGTKLEIS
78%

*FIG. 9A*

Framework 2 specific rearranged antibody
Antibody sequence GI (gene identification) number: 4324018 (germlinenVkII A3. GI:33613)
*not chose this one because AA change in position close to CDR2 (SEQ ID NO. 175)
A------LPVTPGEPASISC RSSQSLLHSNGKNYLD WYLQKPGQSPKLLIY FGSTRAS GVPDRFSGSGSGTDFTLKISRVEAEDVGIYYC MKAQQTPA FGPGTKVEIK Antibody sequence GI (gene identification) number: 18041766 (germline VkII A3. GI:33613) (SEQ ID NO. 176)
B------LPVTPGEPASISC RSSQSLLPGNGYNYLD WFLQRPGQSPQLLIF LTSNRAS GVPDRFSGSGSGTDFTLKISRVEAEDVGVYYC MQARQTPYI FGQGTKL
86%

Framework 3 specific rearranged antibody
Antibody sequence GI (gene identification) number: 553476 AND 33251 (germlinenVkII A3.) (seq id no. 177)
DIVMTQSPLSLPVTPGEPASISC RSSQSLLHSNGYNYLD WYLQKPGQSPQLLIY LGSNRAS GVPDRF SGSGSGTDFTLKISRVEAEDVGVYYC MQALQTPQT FGQGTKVEIKR
93%

*FIG. 9D*

Fig. 9E Framework 4 specific rearranged antibody

Antibody sequence GI (gene identification) number 446245 (SEQ ID NO. 178)

DIVMTQAAFSNPVTLGTSASISC RSSKNLLHSNGITFLY WYLQRPGQSPQLLIY RVSNLAS GVPNRFSGS ESGTDFTLRISRVEAEDVGVYYC AQLLELPYT. FGGGTKLEIK
100%

Fig. 9F Hybrid antibody VL sequence

D1V1 FRs with highest homologies (SEQ ID NO. 179)

DVVMTQSPLSLPVTLGQSASISC RSSQNIVHSNGDTYLE WFLQRPGQSPQLLIF KVSNRFS GVPDRFSGSGSGTDFTLKISRVEAEDVGVYYC FQGSHVPWT FGGGTKLEIK
82%                                                      86%                                     93%                          100%

D1V2 FRs from same family member VkII A3 (SEQ ID NO. 180)

DVVMTQSPLSLPVTLGEPASISC RSSQNIVHSNGDTYLE WFLQRPGQSPQLLIF KVSNRFS GVPDRFSGSGSGTDFTLKISRVEAEDVGVYYC FQGSHVPWT FGGGTKLEIK
78%                                                      86%                                     93%                          100%

D1L (SEQ ID NO. 181)

—L1—                                    —L2—                                    —L3—
DVLMTQSPLSLPVSLGDKASISC RSSQNIVHSNGDTYLE WYLQRPGQSPKLLIF KVSNRFS GVPDRFSGSGSGTDFTLKISRVEAEDLGVYYC FQGSHVPWT FGGGTKLEIK
       FR1                      CDR1              FR2              CDR2                    FR3                CDR3         FR4

Fig. 9H Search with VL combined framework(excluding CDRs) of initial antibody Antibody sequence GI (gene identification) number 929641 which belong to VkII (A3) (SEQ ID NO: 182)

DIVMTQSPLSLPVTLGEPASISC RSSQNIVHSNGDTYLE WYLQKPGQSPQLLIY KVSNRFS GVPDRFSGSGSGTDFTLKISRVEAEDVGVYYC FQGSHVPWT FGGGTKVEIK
74%                                                      80%                                     93%                          90%

Sequence homologies of initial, hybrid and bermline VL sequences

| | Antibody comparisons | Frameworks | CDRs | Whole VL |
|---|---|---|---|---|
| VL | Hybrid antibody versus initial antibody sequence | (72/80) 90% | (32/32) 100% | (104/112) 93% |
| VL | Hybrid antibody versus the most similar human germline sequences VkII (A17) | (65/70) 93% | (16/23) 70% | (81/93) 87% |
| VL | The most similar human rearranged CDR grafted VL versus initial antibody sequence | (68/80) 85% | (32/32) 100% | (100/112) 89% |
| VL | The most similar human rearranged CDR grafted VL versus the most similar human germline sequence VkII (A17) | (62/70) 88% | (16/23) 70% | (78/93) 84% |

FIG. 9G

D1 Heavy Chain

Initial antibody VH protein sequence (SEQ ID NO: 183)
*H1,H2,H3: loop regions structural criteria defined by Chothia
CDRs: are according to Kabat

```
         10(Q)      20(I)      30(T)               40(R)               50(M)      60(N)              70(T)       80(M)                    90(Y)          100(F)---          110(T)
                             --H1---                                 --H2---                                    12abc3                  ↓              ---H3---
                                                                    12a34                                                                              RNGGYYVFDS      WGQGTTLVTVSS
QVQLQQSGPQSVRPGASVKISCKAS    GYSFTSYWMH   WVKQRPGQGLEWIG     MIDPFDSESRLNQEFKD   KATLTVDKSSSTVYMQLSSPTSEDSAIYYCVR                                                       
         FR1                  CDR1             FR2                    CDR2                        FR3                                                        CDR3              FR4
```

*FIG. 10A*

Framework 1 specific rearranged antibody
Antibody sequence GI (gene identification) number: 18698373 (closest germline:VH7-81, GI:4512268) (SEQ ID NO. 184)
QVQLQQSGSELKKPGASVKISCKAS GYSLTDYTIN WVRQA PGQGLEWMG WINTKTGNSTYAQDFIG REVRALDTSVSTAYLQISSLKAEDTALYYCAR GRYSLTRFDP WGQGTLVTVSTS
80%

Antibody sequence GI (gene identification) number: 392677 (closest germline:VH1-2, GI:4512302) (SEQ ID NO. 185)
QVQLVQSGPEVKKPGASVKVSCKAS GYTFTSYGVS WVRQAPGQGLEWMG WISTSDGNTRYPQKLQG RVTM TDTSTSTTYMELRSLRPDDTAVYFCAR DKEPAYFDY WGQGTLVTVSS
76%

*FIG. 10B*

Framework 2 specific rearranged antibody
Antibody sequence GI (gene identification) number: 886288 (closest germline:VH1-2, GI:4512313) (SEQ ID NO. 186)
QVQLLESGAVLARPGTSVKISCKAS GYNFTSYWML WVKQRPGQG LEWIG RAKLTAATSASIAYLEFSSLTNEDSAVYYCAR GDFGAMDY WGQGTLVTVSS Antibody sequence GI (gene identification) number: 999106
(closest germline:VH1-46, GI:4512284-66% OR VH1-69-GI:6512273-69%) (SEQ ID NO. 187)
QVQLLESGAELVRPGSSVKISCKAS GYAFSSYWMN WVKQRPGQGLEWIG QIWPGDGDTNYNGKFKG KATL TADESSSTAYMQLSSLRSEDSAVYSCAR RETTVGRYYYAMDY WGQGTTVT
100%

*FIG. 10C*

Framework 3 specific rearranged antibody
Antibody sequence GI (gene identification) number: 5542538 (closest germline:VH1-2, GI:4512314) (SEQ ID NO. 188)
QVQLLESGAELVKPGASVKLSCKAS GYTFTSYWMH WVKQRPGRGLEWIG MIDPNSGGTKYNEKFKS KATLTVDKPSNTAYMQLSSLTSEDSAVYYCTR RDMDY WGAGTTVTVSS
                                                                                                    81%

*FIG. 10D*

Framework 4 specific rearranged antibody (there are only two antibody having 100% in FR4)
Antibody sequence GI (gene identification) number: 4530559 (closest germline:VH4-34, GI:4512291) (SEQ ID NO. 189)
QVQLQQWGAGLLKPSETLSLTCAVY GGSFSGYSWS WIRQSPGKGLEWIG EINHSGSTNYNSSLKS RVTISVDTSKNQFSLKLNSVTAADTAVYYCAR GVVKGMDV WGQGTTLTVSS

Antibody sequence GI (gene identification) number: 5834122 (closest germline:VH3-48, GI:4512283) (SEQ ID NO. 190)
EVQLVESGGGLVQPGGSLRLSCAAS GFTFSSYSMN WVRQAPGKGLEWVS YISSSSSTIYYADSVKG RFTI SRDNAKNSLYLQMNSLRAEDTAVYYCAR DWSSSQYYYYGMDV WGQGTTLTVSS

The closest VH1 family number                                                                                    100%
Antibody sequence GI (gene identification) number: 1067092 (closest germline:VH1-69, GI:6512273) (SEQ ID NO. 191)
QVQLVQSGAEVKKPGSSVKVSCKAS GGTFSSYAIS WVRQAPGQGLEWMGG IIPIFGTANYAQKFQG RVTITADESTSTAYMELSSLRSEDTAVYYCAR GYYYYYGMDV WGQGTTVTVSS
                                                                                                                   91%

Hybrid antibody VH sequence
DIV1 FRs with highest homologies (SEQ ID NO. 192)
QVQLQQSGSELKKPGASVKISCKAS GYSFTSYWMH WVKQRPGQG LEWIG MIDPFDSESRLNQEFKD KATLTVDKPSNTAYMQLSSLTSEDSAVYYCTR RNGGYYVFDS WGQGTTLTVSS
                   80%                              100%                                                  81%                              100%
DIV2 FRs from same family (SEQ ID NO. 193)
QVQLVQSGPEVKKPGASVKVSCKAS GYSFTSYWMH WVKQRPGQG LEWIG MIDPFDSESRLNQEFKD KATLTVDKPSNTAYMQLSSLTSEDSAVYYCTR RNGGYYVFDS WGQGTTVTVSS
                   76%*VH1-18                      100%*VH1-3                                             81%*VH1-2                        91%*VH1-69

*FIG. 10F*

Search with VH combined framework (excluding CDRs) of initial antibody
Antibody sequence GI (gene identification) number: 5542536 (closest germline:VH1-2, GI:4512314) (SEQ ID NO. 194)
QVQLLESGAELVKPGASVKLSCKAS GYTFTSYWMH WVKQRPGRGLEWIG MIDPNSGGTKYNECFKS KATLTVDKPSNTAYMQLSSLTSEDSAVYYCTR RDMDY WGAGTTVTVSS
                   76%                              93%                                                  75%                              82%
The most similar human rearranged CDR grafted VH (SEQ ID NO. 195)
QVQLLESGAELVKPGASVKLSCKAS GYSFTSYWMH WVKQRPGRGLEWIG MIDPFDSESRLNQEFKD KATLTVDKPSNTAYMQLSSLTSEDSAVYYCTR RNGGYYVFDS WGAGTTVTVSS

*FIG. 10G*

Sequence homologies of initial, hybrid and bermline VH sequences

| | Antibody comparisons | Frameworks | CDRs | Whole VH |
|---|---|---|---|---|
| VH | Hybrid antibody versus initial antibody | (71/82) 87% | (37/37) 100% | (108/119) 91% |
| VH | Hybrid antibody versus the most similar human germline sequence (VH1-46) | (51/71) 72% | (12/27) 44% | (63/98) 64% |
| VH | The most similar human rearranged CDR grafted VH versus initial antibody | (66/82) 80% | (37/37) 100% | (103/119) 87% |
| VH | The most similar human rearranged CDR grafted VH versus the most similar human germline sequence (VH1-46) | (49/71) 69%* | (12/27) 44%* | (61/98) 62%* |

*does not include D and J regions

FIG. 10H

Binding kinetics of initial antibody and hybrid antibody

| Antibody | Kd ($10^{-10}$ M) | Kon ($10^5 s^{-1} M^{-1}$) | Koff ($10^{-4} s^{-1}$) | Kd (Initial/Hybrid) |
|---|---|---|---|---|
| Initial Ab | 12.4 | 7.01 | 1.17 | |
| Hybrid Ab(1) | 17.7 | 0.426 | 1.11 | |
| Hybrid Ab(2) | 4.96 | 0.85 | 0.3 | |
| Hybrid Ave | 11.33 | 0.638 | 0.7 | 1.09 |

Kon: Association rate constant
Koff: Dissociation rate constant
Kd: Affinity

The retention of Initial and hybrid antibodies on MBL (Mannan-binding lectin) was determined on BIAcore 3000 system.
Kd results show a 9% increase of hybrid antibody versus Initial antibody.

*FIG. 12*

Binding kinetics of anti-hDC-SIGN initial antibody and hybrid antibody

| Antibody | Kd ($10^{-10}$ M) | Kon ($10^5 s^{-1} M^{-1}$) | Koff ($10^{-4} s^{-1}$) | Kd (Initial/Hybrid) |
|---|---|---|---|---|
| Initial Ab(AZND1) | 38.8 | 0.62 | 1.17 | |
| Hybrid Ab(D1V1) | 37 | 0.671 | 1.77 | 1.38 |
| Hybrid Ab(D1V2) | 127 | 0.335 | 2.14 | 0.4 |

Kon: Association rate constant
Koff: Dissociation rate constant
Kd: Affinity

The retention of Initial and hybrid antibodies on hDC-SIGN-Fc (human Dendrtic Cell-Specific, ICAM-3 Grabbing Non-integrin) was determined on BIAcore 3000 system. Kd results show a 38% increase on D1V1 and 60% drop on D1V2 hybrid antibody versus Initial antibody.

*FIG. 13*

HYBRID ANTIBODIES

RELATED APPLICATIONS

This application is a continuation-in-part of U.S. application Ser. No. 10/308,817 filed Dec. 3, 2002 which claims priority to U.S. Provisional Application No. 60/336,591 filed on Dec. 3, 2001.

BACKGROUND

1. Technical Field

The present description relates to hybrid antibodies and hybrid antibody fragments derived from one species which preferentially bind a target object and which have reduced immunogenicity in a different species.

2. Background of Related Art

Antibodies are proteins produced by lymphocytes known as B cells in vertebrates in response to stimulation by antigens. The basic structural unit of an antibody (a.k.a. immunoglobulin (Ig)) molecule consists of four polypeptide chains which come together in the shape of a capital letter "Y". Two of the four chains are identical light (L) chains and two are identical heavy (H) chains. There are five different kinds (isotypes) of heavy chains which divide antibodies into five classes, namely, IgA, IgD, IgE, IgG and IgM. In addition, there are two different isotypes of light chains designated κ and λ. Each class of heavy chains can combine with either of the light chains. The heavy and light chains each contain a variable region (VH and VL, respectively) that is involved in antigen binding and a constant (C) region. The antigen binding site is composed of six hypervariable regions (a.k.a. complementarity determining regions (CDRs)). Three CDRs from the heavy chain and three CDRs from the light chain are respectively positioned between four relatively conserved anti-parallel β-sheets which are called framework regions (FR1, FR2, FR3 and FR4), on each chain. By convention, numbering systems have been utilized to designate the location of the component parts of VH and VL chains. The Kabat definition is based on sequence variability and the Chothia definition is based on the location of structural loop regions.

For each type of Ig chain synthesized by B cells, there is a separate pool of gene segments, known as germline genes, from which a single polypeptide chain is synthesized. Each pool is located on a different chromosome and typically contains a relatively large number of gene segments encoding the V region and a lesser number of gene segments encoding the C region. Each light chain V region is encoded by a nucleic acid sequence assembled from two kinds of germline gene segments, i.e., a long V gene segment, a short joining (J) gene segment, and a C segment. The heavy chain is encoded by four kinds of germline gene segments, three for the variable region and one for the constant region. The three germline gene segments that encode the heavy chain variable region are a V segment, a J segment and a diversity (D) segment. Human germline V, D and J gene sequences have been characterized. The human germline VH gene segments (such "segments" are also referred to herein as family members) are classified into seven families (VH1-VH7) based on sequence homology of at least 80%. See, e.g., Matsuda, et al. J. Exp. Med. (1998) 188:2151-2162. There are approximately fifty-one VH segments (family members). The first two CDRs and three framework regions of the heavy chain variable region are encoded by VH. CDR3 is encoded by a few nucleotides of VH, all of DH and part of JH, while FR4 is encoded by the remainder of the JH gene segment. With regard to light chains, V Kappa (Vκ) or V lambda (Vλ) gene segments (family members) encode the first two CDR and three framework regions of the V region along with a few residues of CDR3. J Kappa (Jκ) and J Lambda (Jλ) segments encode the remainder of the CDR3 region in a Vκ or Vλ region, respectively. DNA encoding the K chain includes approximately forty Vκ segments (family members) that are classified into six families (VκI-Vκ VI) based on sequence homology. DNA encoding the λ chain includes approximately thirty-one Vλ segments (family members) that are classified into ten families. See FIGS. 1, 2, 3 and 6.

Antibodies and antibody fragments have become promising therapeutic agents in connection with various human diseases in both acute and chronic settings. There are several methods being utilized to generate antibodies including hybridoma technology, bacterial display, ribosome display, yeast display, and recombinant expression of human antibody fragments on the surface of replicative bacteriophage. Monoclonal antibodies (mAbs), which may be produced by hybridomas, have been applied successfully as diagnostics for many years, but their use as therapeutic agents is just emerging. The vast majority of mAbs are of non-human (largely rodent) origin, posing the problem of immunogenicity in humans. When antibodies of rodent origin are administered to humans, anti-rodent antibodies are generated which result in enhanced clearance of the rodent antibody from the serum, blocking of its therapeutic effect and hypersensitivity reactions. These limitations have prompted the development of engineering technologies known as "humanization".

The first humanization strategies were based on the knowledge that heavy and light chain variable domains are responsible for binding to antigen, and the constant domains for effector function. Chimeric antibodies were created, for example, by transplanting the variable domains of a rodent mAb to the constant domains of human antibodies (e.g. Neuberger M S, et al., Nature 314, 268-70, 1985 and Takeda, et al., Nature 314, 452-4, 1985). Although these chimeric antibodies induce better effector functions in humans and exhibit reduced immunogenicity, the rodent variable region still poses the risk of inducing an immune response. When it was recognized that the variable domains consist of a beta sheet framework surmounted by antigen-binding loops (complementarity determining regions or CDR's), humanized antibodies were designed to contain the rodent CDR's grafted onto a human framework. Several different antigen-binding sites were successfully transferred to a single human framework, often using an antibody where the entire human framework regions have the closest homology to the rodent sequence (e.g., Jones P T, et al., Nature 321, 522-5, 1986; Riechmann L. et al., Nature 332, 323-327, 1988; and Sato K. et al., Mol. Immunol. 31, 371-8, 1994). Alternatively, consensus human frameworks were built based on several human heavy chains (e.g., Carter P. et al., Proc. Nat. Acad. Sci. USA 89, 487-99, 1992). However, simple CDR grafting often resulted in loss of antigen affinity. Other possible interactions between the β-sheet framework and the loops had to be considered to recreate the antigen binding site (Chothia C, et al., Mol. Biol. 196, 901-917, 1987).

Comparison of the essential framework residues required in humanization of several antibodies, as well as computer modeling based on antibody crystal structures revealed a set of framework residues termed as "Vernier zone residues" (Foote J., et al., Mol Biol 224, 487-99, 1992) that most likely contributes to the integrity of the binding site. In addition, several residues in the VH-VL interface zone might be important in maintaining affinity for the antigen (Santos A D, et al., Prog. Nucleic Acid Res Mol Biol 60, 169-94 1998). Initially, framework residues were stepwise mutated back to the rodent sequence (Kettleborough C A, et al. Protein Engin. 4, 773-783, 1991). However, this mutation approach is very time-consuming and cannot cover every important residue.

For any particular antibody a small set of changes may suffice to optimize binding, yet it is difficult to select from the set of Vernier and VH/VL residues. Combinatorial library approaches combined with selection technologies (such as phage display) revolutionized humanization technologies by creating a library of humanized molecules that represents alternatives between rodent and human sequence in all important framework residues and allows for simultaneous determination of binding activity of all humanized forms (e.g. Rosok M J, J Biol Chem, 271, 22611-8, 1996 and Baca M, et al. J Biol Chem 272, 10678-84, 1997).

The above approaches utilize entire framework regions from a single antibody variable heavy or variable light chain to receive the CDRs. It is advantageous to provide highly homologous engineered antibodies based on antibodies from an originating species which exhibit reduced immunogenicity while maintaining an optimum binding profile that can be administered to a target species for therapeutic and diagnostic purposes.

SUMMARY

In one aspect, a method for producing a hybrid antibody or hybrid antibody fragment is provided which includes providing an initial antibody having specificity for a target; determining the sequence of at least a portion of a variable region of the initial antibody; and (i) selecting a first component of the variable region selected from the group consisting of FR1, FR2, FR3 and FR4; comparing the sequence of the first selected component to sequences contained in a reference database of antibody sequences or antibody fragment sequences from a target species; and selecting a sequence from an antibody in the database which demonstrates a high degree of homology to the first component; (ii) selecting a second component of the variable region which is different than the first component, the second component selected from the group consisting of FR1, FR2, FR3 and FR4; comparing the sequence of the second component to sequences contained in a reference database of antibody sequences or antibody fragment sequences from the target species; selecting a sequence from the database which demonstrates a high degree of homology to the second component and which is from a different antibody than the antibody selected in step (i); and (iii) operatively linking the selected framework sequences to one or more CDRs of the initial antibody to produce a hybrid antibody or hybrid antibody fragment. The method described above may be continued with respect to the remaining components of the variable region until an entire variable region is synthesized. The remaining components may be from the same or different antibodies than those selected from the database in steps (i) and (ii) above. The first, second and/or remaining components above may include one or more CDRs. It should be understood that combinations of the framework regions within the first, second and/or remaining components can be used for comparison in the steps set forth above. The variable region of the initial antibody may be a variable light chain or a variable heavy chain. The sequences referred to above may be amino acid sequences or nucleic acid sequences. The antibody may be any known antibody form known to those skilled in the art, e.g., whole antibodies, chimeric antibodies, bivalent antibodies and the like. The antibody fragment referred to above may be selected from the group consisting of scFv, Fab, Fab', F(ab')$_2$, Fd, antibody light chains and antibody heavy chains. The target species may be human.

In one embodiment, the FR1 region sequence from the initial antibody is used individually to search the reference database for sequences having a high degree of homology. In another embodiment, the FR2 region sequence from the initial antibody is used individually to search the reference database for sequences having a high degree of homology. In another embodiment, the FR3 region sequence from the initial antibody is used individually to search the reference database for sequences having a high degree of homology. In another embodiment, the FR4 region sequence from the initial antibody is used individually to search the reference database for sequences having a high degree of homology. The reference database may contain germline or rearranged antibody sequences of the target species.

In another aspect, a method for producing a hybrid antibody or hybrid antibody fragment is provided which includes providing an initial antibody having specificity for a target; determining the sequence of at least a portion of a variable framework region of the initial antibody; and (i) selecting a first component of the variable region selected from the group consisting of FR1, FR2 and FR3; comparing the sequence of the first component of the variable region to sequences contained in a reference database of antibody sequences or antibody fragment sequences from a target species; selecting a sequence from the database which demonstrates a high degree of homology to the first component; and determining the germline gene family from which the sequence was derived; (ii) selecting a second component of the variable region which is different than the first component, the second component selected from the group consisting of FR1, FR2 and FR3; comparing the sequence of the second component to sequences contained in a reference database of antibody sequences or antibody fragment sequences from the target species; selecting a sequence from the database which demonstrates a high degree of homology to the second component and which corresponds to the same germline gene family as the first sequence selected from the database in step (i) of this paragraph; and (iii) operatively linking the selected framework sequences to one or more CDRs of the initial antibody to produce a hybrid antibody or hybrid antibody fragment. The method described in this aspect may be continued with respect to the third component of the framework region. In one embodiment, FR4 is added and operatively linked to the product of step (iii) of this paragraph and an entire variable region is synthesized. The method can be extended until an entire hybrid antibody is produced. The variable framework region of the initial antibody may be a light chain or a heavy chain. The first, second and/or third components in this paragraph may include one or more CDRs. It should be understood that combinations of the framework regions within the first, second and/or third components can be used for comparison in the steps set forth in this paragraph.

In one embodiment, two or more of the sequences selected from the reference database are from different antibodies. The sequences referred to above may be amino acid sequences or nucleic acid sequences. The antibody may be any known antibody form known to those skilled in the art, e.g., whole antibodies, chimeric antibodies, bivalent antibodies and the like. The antibody fragment referred to above may be selected from the group consisting of scFv, Fab, Fab', F(ab')$_2$, Fd, antibody light chains and antibody heavy chains. The target species may be human.

In one embodiment, the FR1 region sequence from the initial antibody is used individually to search the reference database for sequences having a high degree of homology and the germline gene family to which it belongs is used as the family to which the other selected sequence corresponds. In another embodiment, the FR2 region sequence from the initial antibody is used individually to search the reference database for sequences having a high degree of homology and the germline gene family to which it belongs is used as the family to which the other selected sequence corresponds. In another embodiment, the FR3 region sequence from the initial antibody is used individually to search the reference database for sequences having a high degree of homology and the germline gene family to which it belongs is used as the family to which the other selected sequence corresponds. In another embodiment, the FR4 region sequence from the initial antibody is used individually to search the reference database for FR4 germline sequences which are chosen from those which have the highest homology of human JH, Jκ, or Jλ family members. The reference database may contain germline or rearranged sequences of the target species. In one embodiment, at least two of the selected sequences correspond to the same family member in the germline gene family.

In another aspect, a hybrid antibody or hybrid antibody fragment includes a first heavy chain framework region from a first antibody, and a second heavy chain framework region from a second antibody. In one embodiment, the hybrid antibody or hybrid antibody fragment includes a third heavy chain framework region originating from an antibody selected from the group consisting of the first antibody, the second antibody and a third antibody which is neither the first nor the second antibody. In another embodiment, the hybrid antibody or hybrid antibody fragment includes a fourth heavy chain framework region from an antibody selected from the group consisting of the first antibody, the second antibody, the third antibody and a fourth antibody which is neither the first, second nor third antibody. In one embodiment, the framework regions are of human origin and the CDRs are of nonhuman origin.

In another aspect, a hybrid antibody includes a first light chain framework region from a first antibody, and a second light chain framework region from a second antibody. In one embodiment, the hybrid antibody includes a third light chain framework region originating from an antibody selected from the group consisting of the first antibody, the second antibody and a third antibody which is neither the first nor the second antibody. In another embodiment, the hybrid antibody includes a fourth light chain framework region, originating from an antibody selected from the group consisting of the first antibody, the second antibody, the third antibody and a fourth antibody which is neither the first, second nor third antibody. In one embodiment, the framework regions are of human origin and the CDRs are of nonhuman origin.

In another aspect, a hybrid antibody includes a first heavy chain framework region from a first antibody, the first heavy chain framework region corresponding to a particular VH family, and a second heavy chain framework region from a second antibody, the second heavy chain framework region corresponding to the same VH family as the first heavy chain framework region. In one embodiment, the hybrid antibody includes a third heavy chain framework region originating from an antibody selected from the group consisting of the first antibody, the second antibody and a third antibody which is neither the first nor the second antibody. The third framework region corresponds to the same VH family as the first heavy chain framework region. In another embodiment, the hybrid antibody includes a fourth heavy chain framework region from an antibody selected from the group consisting of the first antibody, the second antibody, the third antibody and a fourth antibody which is neither the first, second nor third antibody. In yet another embodiment, either, or both, of the second heavy chain framework region and the third heavy chain framework region correspond to the same member of the VH family as the first heavy chain framework region. In one embodiment, the framework regions are of human origin and the CDRs are of nonhuman origin. Germline FR4 is selected from those of the highest homology of corresponding J region.

In another aspect, a hybrid antibody includes a first light chain framework region from a first antibody, the first light chain framework region corresponding to a particular Vκ family, and a second light chain framework region from a second antibody, the second light chain framework region corresponding to the same Vκ family as the first light chain framework region. In one embodiment, the hybrid antibody includes a third light chain framework region originating from an antibody selected from the group consisting of the first antibody, the second antibody and a third antibody which is neither the first nor the second antibody. The third framework region corresponds to the same Vκ family as the first light chain framework region. In another embodiment, the hybrid antibody includes a fourth light chain framework region, originating from an antibody selected from the group consisting of the first antibody, the second antibody, the third antibody and a fourth antibody which is neither the first, second nor third antibody. In yet another embodiment, either, or both, of the second light chain framework region and the third light chain framework region correspond to the same member of the Vκ family as the first light chain framework region. In one embodiment, the framework regions are of human origin and the CDRs are of nonhuman origin.

In another aspect, a hybrid antibody includes a first light chain framework region from a first antibody, the first light chain framework region corresponding to a particular Vλ family, and a second light chain framework region from a second antibody, the second light chain framework region corresponding to the same Vλ family as the first light chain framework region. In one embodiment, the hybrid antibody includes a third light chain framework region originating from an antibody selected from the group consisting of the first antibody, the second antibody and a third antibody which is neither the first nor the second antibody. The third framework region corresponds to the same Vλ family as the first light chain framework region. In another embodiment, the hybrid antibody includes a fourth light chain framework region, originating from an antibody selected from the group consisting of the first antibody, the second antibody, the third antibody and a fourth antibody which is neither the first, second nor third antibody. In yet another embodiment, either, or both, of the second light chain framework region and the third light chain framework region correspond to the same member of the Vλ family as the first light chain framework region. In one embodiment, the framework regions are of human origin and the CDRs are of nonhuman origin.

In another aspect, a library of antibodies or antibody fragments is provided which includes hybrid antibodies and/or hybrid antibody fragments according to the present disclosure.

BRIEF DESCRIPTION OF THE DRAWINGS

FIG. 1 is a chart depicting germline genes of the Vκ gene locus. Vκ exon amino acid sequence alignment is shown. Alignments, numbering and loop regions are according to the structural criteria defined by Chothia. CDRs are according to Kabat, et al.

FIG. 2 is a chart depicting germline genes of the VH gene locus. VH exon amino acid sequence alignment is shown. Alignments, numbering and loop regions are according to the structural criteria defined by Chothia. CDRs are according to Kabat, et al.

FIG. 3 is a chart depicting germline genes of the Vλ gene locus. Vλ exon amino acid sequence alignment is shown. Alignments, numbering and loop regions are according to the structural criteria defined by Chothia. CDRs are according to Kabat, et al.

FIG. 4A depicts the amino acid sequence (Seq. Id. No. 123) of a murine antibody variable light chain directed to human mannose binding lectin (i.e., the light chain of the initial antibody), separating the sequence into framework and CDR components.

FIG. 4B depicts the amino acid sequence (Seq. Id. No. 124) of human antibody variable light chain sequence gene identification (GI) number 3747016, separating the sequence into framework and CDR component parts.

FIG. 4C depicts the amino acid sequence (Seq. Id. No. 125) of human antibody variable light chain sequence gene identification (GI) number 5833827, separating the sequence into framework and CDR component parts.

FIG. 4D depicts the amino acid sequence (Seq. Id. No. 126) of human antibody variable light chain sequence gene identification (GI) number 722614, separating the sequence into framework and CDR component parts.

FIG. 4E depicts the amino acid sequence (Seq. Id. No. 127) of human antibody variable light chain sequence gene identification (GI) number 1785870, separating the sequence into framework and CDR component parts.

FIG. 4F depicts the amino acid sequence of a hybrid humanized antibody light chain (Seq. Id. No. 128), separating the sequence into framework and CDR component parts. Percent homology of each framework region to the initial murine monoclonal antibody light chain of FIG. 4A is provided.

FIG. 4G is a chart showing the degree of homology between the hybrid humanized version of the murine monoclonal antibody light chain (see FIG. 4F) and the initial murine monoclonal antibody light chain (see FIG. 4A) in terms of framework regions alone, CDRs alone and whole Vκ chain. Also shown is the degree of homology between the hybrid humanized version of the murine monoclonal antibody light chain and the most similar human germline sequence VκVI (A10/A26). Also shown is the degree of homology between the most similar human rearranged CDR grafted variable light chain obtained by prior art methods and the initial murine monoclonal antibody light chain. Also shown is the most similar human rearranged CDR grafted VL versus the most similar human germline sequence VκVI (A14).

FIG. 4H depicts an amino acid sequence (Seq. Id. No. 129) resulting from a BLAST query in Genbank using the entire variable light chain of the initial murine monoclonal antibody depicted in FIG. 4a.

FIG. 4I depicts an amino acid sequence (Seq. Id. No. 130) resulting from a BLAST query in Genbank using only the combined framework regions of the variable light chain of the initial murine monoclonal antibody depicted in FIG. 4a.

FIG. 5A depicts the amino acid sequence (Seq. Id. No. 131) of a murine antibody variable heavy chain directed to human mannose binding lectin (i.e., the heavy chain of the initial antibody), separating the sequence into framework and CDR components.

FIG. 5B depicts the amino acid sequence (Seq. Id. No. 132) of human antibody variable heavy chain sequence gene identification (GI) number 563649, separating the sequence into framework and CDR component parts.

FIG. 5C depicts the amino acid sequence (Seq. Id. No. 133) of human antibody variable heavy chain sequence gene identification (GI) number 951263, separating the sequence into framework and CDR component parts.

FIG. 5D depicts the amino acid sequence (Seq. Id. No. 134) of human antibody variable heavy chain sequence gene identification (GI) number 484852, separating the sequence into framework and CDR component parts.

FIG. 5E depicts the amino acid sequence (Seq. Id. No. 135) of human antibody variable heavy chain sequence gene identification (GI) number 2367531, separating the sequence into framework and CDR component parts.

FIG. 5F depicts the amino acid sequence of a hybrid humanized antibody heavy chain (Seq. Id. No. 136), separating the sequence into framework and CDR component parts. Percent homology of each framework region to the initial murine monoclonal antibody heavy chain of FIG. 5a is provided.

FIG. 5G is a chart showing the degree of homology between the hybrid humanized version of the murine monoclonal antibody heavy chain (see FIG. 5F) and the initial murine monoclonal antibody heavy chain (see FIG. 5A) in terms of framework regions alone, CDRs alone and whole VH chain. Also shown is the degree of homology between the hybrid humanized version of the murine monoclonal antibody heavy chain and the most similar human germline sequence VH4-31. Also shown is the degree of homology between the most similar human rearranged CDR grafted variable heavy chain obtained by prior art methods and the initial murine monoclonal antibody heavy chain. Also shown is the degree of homology between the most similar human rearranged CDR grafted VH versus the most similar germline sequence VH4-31.

FIG. 5H depicts an amino acid sequence (Seq. Id. No. 137) resulting from a BLAST query in Genbank using the entire variable heavy chain of the murine antibody depicted in FIG. 5A.

FIG. 5I depicts an amino acid sequence (Seq. Id. No. 138) resulting from a BLAST query in Genbank using only the combined framework regions of the variable heavy chain of the murine monoclonal antibody depicted in FIG. 5A.

FIG. 6 is a chart depicting translated germline genes of the JH, JK and JL gene loci in terms of amino acid sequence alignment.

FIG. 7 depicts the nucleic acid (Seq. Id. No. 154) and amino acid (Seq. Id. No. 155) sequences of the hybrid humanized variable light chain and of the nucleic acid sequence (Seq. Id. No. 156) and amino acid sequence (Seq. Id. No. 157) of the hybrid humanized variable heavy chain and indicates the positions of particular nucleotides and amino acids that were altered as compared to the initial murine antibody sequences. Framework regions are underlined and altered nucleotides and amino acids are boldface.

FIG. 8 depicts the nucleotide sequences of oligonucleotide chains that were utilized for site directed mutagenesis of the initial murine antibody variable light and variable heavy chains. The chains are designated as follows: for VL: Oligo 1 (Seq. Id. No. 158), Oligo 2 (Seq. Id. No. 159), Oligo 3 (Seq. Id. No. 160), Oligo 4 (Seq. Id. No. 161), Oligo 5 (Seq. Id. No. 162), Oligo 6 (Seq. Id. No. 163), Oligo 7 (Seq. Id. No. 164); for VH: Oligo 8 (Seq. Id. No. 165), Oligo 9 (Seq. Id. No. 166), Oligo 10 (Seq. Id. No. 167), Oligo 11 (Seq. Id. No. 168), Oligo 12 (Seq. Id. No. 169), Oligo 13 (Seq. Id. No. 170), Oligo 14 (Seq. Id. No. 171).

FIG. 9A depicts the amino acid sequence (Seq. Id. No. 172) of a murine antibody variable light chain directed to h-DC-SIGN (i.e., the light chain of the initial antibody), separating the sequence into framework and CDR components.

FIG. 9B depicts the amino acid sequences (Seq. Id. Nos. 173 and 174) of human antibody variable light chain sequence gene identification (GI) numbers 441333 and 5578780, separating the sequence into framework and CDR component parts.

FIG. 9C depicts the amino acid sequences (Seq. Id. Nos. 175 and 176) of human antibody variable light chain sequence gene identification (GI) number 4324018 and 18041766, separating the sequence into framework and CDR component parts.

FIG. 9D depicts the amino acid sequence (Seq. Id. No. 177) of human antibody variable light chain sequence gene identification (GI) numbers 553476 and 33251, separating the sequence into framework and CDR component parts.

FIG. 9E depicts the amino acid sequence (Seq. Id. No. 178) of human antibody variable light chain sequence gene identification (GI) number 446245, separating the sequence into framework and CDR component parts.

FIG. 9F depicts the amino acid sequences of hybrid humanized antibody light chain (Seq. Id. Nos. 179, 180 and 181), separating the sequence into framework and CDR component parts. Percent homology of each framework region to the initial murine monoclonal antibody light chain of FIG. 9A is provided.

FIG. 9G is a chart showing the degree of homology between the hybrid humanized version of the murine monoclonal antibody light chain (see FIG. 9F) and the initial murine monoclonal antibody light chain (see FIG. 9A) in terms of framework regions alone, CDRs alone and whole Vκ chain. Also shown is the degree of homology between the hybrid humanized version of the murine monoclonal antibody light chain and the most similar human germline sequence. Also shown is the degree of homology between the most similar human rearranged CDR grafted variable light chain obtained by prior art methods and the initial murine monoclonal antibody light chain. Also shown is the most similar human rearranged CDR grafted VL versus the most similar human germline sequence.

FIG. 9H depicts an amino acid sequence (Seq. Id. No. 182) resulting from a BLAST query in Genbank using the entire variable light chain of the initial murine monoclonal antibody (excluding CDRs) depicted in FIG. 9A.

FIG. 10A depicts the amino acid sequence (Seq. Id. No. 183) of a murine antibody variable heavy chain directed to h-DC-SIGN (i.e., the heavy chain of the initial antibody), separating the sequence into framework and CDR components.

FIG. 10B depicts the amino acid sequences (Seq. Id. Nos. 184 and 185) of human antibody variable heavy chain sequence gene identification (GI) numbers 18698373 and 392677, separating the sequence into framework and CDR component parts.

FIG. 10C depicts the amino acid sequences (Seq. Id. Nos. 186 and 187) of human antibody variable heavy chain sequence gene identification (GI) numbers 886288 and 999106, separating the sequence into framework and CDR component parts.

FIG. 10D depicts the amino acid sequence (Seq. Id. No. 188) of human antibody variable heavy chain sequence gene identification (GI) number 5542538, separating the sequence into framework and CDR component parts.

FIG. 10E depicts the amino acid sequences (Seq. Id. Nos. 189, 190 and 191) of human antibody variable heavy chain sequence gene identification (GI) numbers 4530559, 5834122 and 106709, separating the sequence into framework and CDR component parts.

FIG. 10F depicts the amino acid sequences of a hybrid humanized antibody heavy chain (Seq. Id. Nos. 192 and 193), separating the sequence into framework and CDR component parts. Percent homology of each framework region to the initial murine monoclonal antibody heavy chain of FIG. 10A is provided.

FIG. 10G depicts an amino acid sequences (Seq. Id. Nos. 194 and 195) resulting from a BLAST query in Genbank using the entire variable heavy chain of the murine antibody depicted in FIG. 10A.

FIG. 10H is a chart showing the degree of homology between the hybrid humanized version of the murine monoclonal antibody heavy chain (see FIG. 10F) and the initial murine monoclonal antibody heavy chain (see FIG. 10A) in terms of framework regions alone, CDRs alone and whole VH chain. Also shown is the degree of homology between the hybrid humanized version of the murine monoclonal antibody heavy chain and the most similar human germline sequence. Also shown is the degree of homology between the most similar human rearranged CDR grafted variable heavy chain obtained by prior art methods and the initial murine monoclonal antibody heavy chain. Also shown is the degree of homology between the most similar human rearranged CDR grafted VH versus the most similar germline sequence.

FIG. 12 shows the results of binding affinity testing on the initial antibody and a hybrid antibody directed to mannan-binding lectin (MBL).

FIG. 13 shows the results of binding affinity testing on the initial antibody and hybrid antibodies directed to h-DC-SIGN.

DETAILED DESCRIPTION OF PREFERRED EMBODIMENTS

Figure 11:
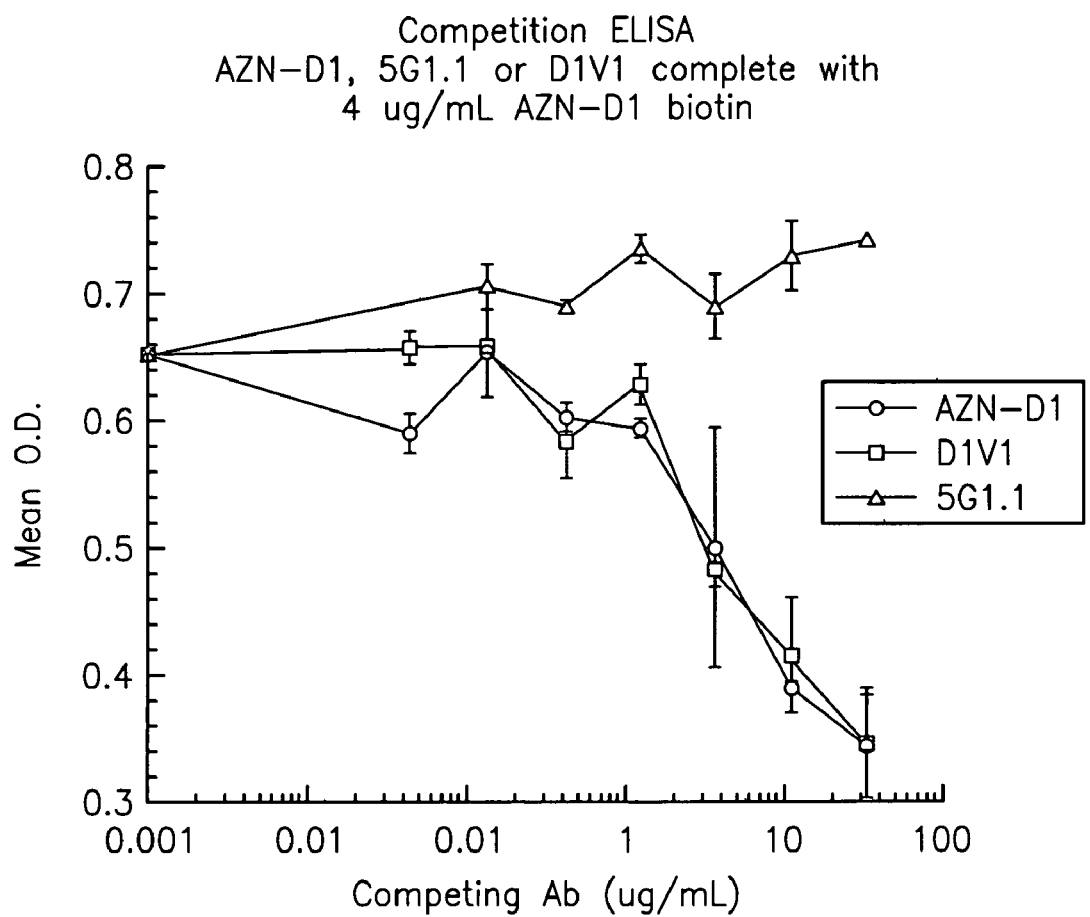
FIG. 11 shows the results of competition ELISA experiments involving an antibody in accordance with the present disclosure and comparative antibodies.

The techniques described herein provide hybrid antibodies or hybrid antibody fragments (collectively referred to herein as "hybrids") which are active against a target object and which reduce the risk of immunogenicity when administered to a target species. The present disclosure provides techniques which maximize homology between framework regions of antibodies or antibody fragments obtained from an originating species and those of a target species. Hybrids that have been constructed by incorporation of highly homologous framework regions from two or more antibodies of a target species and which have been manipulated in accordance with the present disclosure maintain a high degree of affinity to the target object while reducing the risk of an adverse immune response when administered to the target species. In addition, hybrids that have been constructed by incorporation of highly homologous framework regions from one or more antibodies of a target species which correspond to the same family of germline gene sequences and which have been manipulated in accordance with the present disclosure also maintain a high degree of affinity to the target object while reducing the risk of an adverse immune response when administered to the target species. In one embodiment, the target species is human and the engineered antibody is humanized.

Technical and scientific terms used herein have the meanings commonly understood by one of ordinary skill in the art to which the present teachings pertain, unless otherwise defined herein. Reference is made herein to various methodologies known to those of skill in the art. Publications and other materials setting forth such known methodologies to which reference is made are incorporated herein by reference in their entireties as though set forth in full. Practice of the methods described herein will employ, unless otherwise indicated, conventional techniques of chemistry, molecular biology, microbiology, recombinant DNA, and immunology, which are within the skill of the art. Such conventional techniques are explained fully in the literature. See, e.g., Sambrook, Fritsch, and Maniatis, Molecular Cloning; Laboratory Manual 2nd ed. (1989); DNA Cloning, Volumes I and II (D. N Glover ed. 1985); Oligonucleotide Synthesis (M. J. Gait ed, 1984); Nucleic Acid Hybridization (B. D. Hames & S. J. Higgins eds. 1984); the series, Methods in Enzymology (Academic Press, Inc.), particularly Vol. 154 and Vol. 155 (Wu and Grossman, eds.); PCR-A Practical Approach (McPherson, Quirke, and Taylor, eds., 1991); Immunology, 2d Edition, 1989, Roitt et al., C. V. Mosby Company, and New York; Advanced Immunology, 2d Edition, 1991, Male et al., Grower Medical Publishing, New York; DNA Cloning: A Practical Approach, Volumes I and II, 1985 (D. N. Glover ed.); Oligonucleotide Synthesis, 1984, (M. L. Gait ed); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; and Gene Transfer Vectors for Mammalian Cells, 1987 (J. H. Miller and M. P. Calos eds., Cold Spring Harbor Laboratory); WO97/08320; U.S. Pat. Nos. 5,427,908; 5,885,793; 5,969,108; 5,565,332; 5,837,500; 5,223,409; 5,403,484; 5,643,756; 5,723,287; 5,952,474; Knappik et al., 2000, J. Mol. Biol. 296:57-86; Barbas et al., 1991, Proc. Natl. Acad. Sci. USA 88:7978-7982; Schaffitzel et al. 1999, J. Immunol. Meth. 10:119-135; Kitamura, 1998, Int. J. Hematol., 67:351-359; Georgiou et al., 1997, Nat. Biotechnol. 15:29-34; Little, et al., 1995, J. Biotech. 41:187-195; Chauthaiwale et al., 1992, Microbiol. Rev., 56:577-591; Aruffo, 1991, Curr. Opin. Biotechnol. 2:735-741; McCafferty (Editor) et al., 1996, Antibody Engineering: A Practical Approach, the contents of which are incorporated herein by reference.

Any suitable materials and/or methods known to those of skill can be utilized in carrying out the methods described herein; however, preferred materials and/or methods are described. Materials, reagents and the like to which reference is made in the following description and examples are obtainable from commercial sources, unless otherwise noted.

The hybrid antibodies and hybrid antibody fragments include complete antibody molecules having full length heavy and light chains, or any fragment thereof, such as Fab, Fab', F(ab')$_2$, Fd, scFv, antibody light chains and antibody heavy chains. Chimeric antibodies which have variable regions as described herein and constant regions from various species are also suitable.

Initially, a predetermined target object is chosen to which an antibody may be raised. Techniques for generating monoclonal antibodies directed to target objects are well known to those skilled in the art. Examples of such techniques include, but are not limited to, those involving display libraries, xeno or humab mice, hybridomas, etc. Target objects include any substance which is capable of exhibiting antigenicity and are usually proteins or protein polysaccharides. Examples include receptors, enzymes, hormones, growth factors, peptides and the like. It should be understood that not only are naturally occurring antibodies suitable for use in accordance with the present disclosure, but engineered antibodies and antibody fragments which are directed to a predetermined object are also suitable.

Antibodies (Abs) that can be subjected to the techniques set forth herein include monoclonal and polyclonal Abs, and antibody fragments such as Fab, Fab', F(ab')$_2$, Fd, scFv, diabodies, antibody light chains, antibody heavy chains and/or antibody fragments derived from phage or phagemid display technologies. To begin with, an initial antibody is obtained from an originating species. More particularly, the nucleic acid or amino acid sequence of the variable portion of the light chain, heavy chain or both, of an originating species antibody having specificity for a target antigen is needed. The originating species is any species which was used to generate the antibodies or antibody libraries, e.g., rat, mice, rabbit, chicken, monkey, human, etc. Techniques for generating and cloning monoclonal antibodies are well known to those skilled in the art. After a desired antibody is obtained, the variable regions (VH and VL) are separated into component parts (i.e, frameworks (FRs) and CDRs) using any possible definition of CDRs (e.g., Kabat alone, Chothia alone, Kabat and Chothia combined, and any others known to those skilled in the art). Once that has been obtained, the selection of appropriate target species frameworks is necessary. One embodiment involves alignment of each individual framework region from the originating species antibody sequence with variable amino acid sequences or gene sequences from the target species. Programs for searching for alignments are well known in the art, e.g., BLAST and the like. For example, if the target species is human, a source of such amino acid sequences or gene sequences (germline or rearranged antibody sequences) may be found in any suitable reference database such as Genbank, the NCBI protein databank (world wide web at ncbi.nlm.nih.gov/BLAST), VBASE, a database of human antibody genes (world wide web at mrc-cpe.cam.ac.uk/imt-doc), and the Kabat database of immunoglobulins (world wide web at immuno.bme.nwu.edu) or translated products thereof. If the alignments are done based on the nucleotide sequences, then the selected genes should be analyzed to determine which genes of that subset have the closest amino acid homology to the originating species antibody. It is contemplated that amino acid sequences or gene sequences which approach a higher degree homology as compared to other sequences in the database can be utilized and manipulated in accordance with the procedures described herein. Moreover, amino acid sequences or genes which have lesser homology can be utilized when they encode products which, when manipulated and selected in accordance with the procedures described herein, exhibit specificity for the predetermined target antigen. In certain embodiments, an acceptable range of homology is greater than about 50%. It should be understood that target species may be other than human.

In one aspect, after determining the degree of homology of an individual framework region from an originating species, i.e., FR1, FR2, FR3 or FR4, with the most similar matches from two or more different antibodies in the reference database of the target species, a set of homologous sequences is selected which can include, e.g., the top 100 hits. This is done with each individual framework region while looking for matches in the database with the closest homology to the antibody from the originating species. It is contemplated that at least two of the selected sequences may be obtained from different antibodies in the database. For example, FR1 may come from antibody one, FR2 may come from antibody two, FR3 may come from either antibody one, antibody two or a third antibody which is neither the antibody one nor antibody two, and FR4 may come from either antibody one, antibody two, antibody three or antibody four which is neither antibody one nor antibody two nor antibody three, with the caveat that at least two FRs are from different antibodies. As another example, FR1 may come from antibody one, FR3 may come from antibody two, FR2 may come from either antibody one, antibody two or a third antibody which is neither the antibody one nor antibody two, and FR4 may come from either antibody one, antibody two, antibody three or antibody four which is neither antibody one nor antibody two nor antibody three, with the caveat that at least two FRs are from different antibodies. As another example, FR1 may come from antibody one, FR4 may come from antibody two, FR2 may come from either antibody one, antibody two or a third antibody which is neither the antibody one nor antibody two, and FR3 may come from either antibody one, antibody two, antibody three or antibody four which is neither antibody one nor antibody two nor antibody three, with the caveat that at least two FRs are from different antibodies. After selecting suitable framework region candidates, either or both the heavy and light chains variable regions are produced as further discussed below by grafting the CDRs from the originating species into the hybrid framework regions.

In another aspect, after determining the degree of homology of an individual framework region from an originating species, i.e., FR1, FR2, FR3 or FR4, with the most similar matches of germline or rearranged antibody sequences, a set of homologous sequences is selected which can include, e.g., the top 100 hits. At that point, with respect to FR1, FR2, and FR3, the members of the set are categorized into original germline families, i.e., VH1, VH2, VH3, etc., VκI, VκII, VκIII, etc. and Vλ1, Vλ2, Vλ3, etc., and further, into family members where possible. See FIGS. 1, 2 and 3 for a more complete listing of families and family members. Although not always the case, the most similar sequence matches for each individual framework region will typically come from different antibodies or antibody fragments. In one embodiment, two or more framework regions come from antibodies in the same variable family. In another embodiment, two or more framework regions come from a different antibody from the same family member. In another embodiment, up to three framework regions can be from the same antibody. It is contemplated that even though there may be framework sequences in the database from a different family with a higher degree of homology, the more preferable candidate sequence may actually have lower homology but be from the same family as the other selected frameworks. Similarly, there may be framework sequences in the database from the same family with high homology, but from different members of the same family; the more preferable candidates may be from the same family member as the other selected frameworks. An optional selection criteria involves checking to see which framework sequences most closely resemble the somatic mutations contained in the originating species antibody. Somatic mutations cause the sequences of antibodies to be different even if they come from the same family member. In certain embodiments it is preferable to make a selection that is closer to the somatic mutations occurring in the originating species sequence.

FR4 regions are not matched between families and family members of FR1, FR2, and FR3. Indeed, FR4 is encoded by J segments (See FIG. 6) and a choice of suitable FR4 sequences can be determined based on homology between the initial antibody FR4 sequences and the most similar FR4 sequences in a reference database. In one embodiment, the FR4 is chosen based on the degree of maximum homology between the initial antibody and those found in rearranged antibody sequence reference databases. In certain embodiments, 100% homology is preferred between the FR4 from the initial antibody and the FR4 selected from the reference database of the target species. Choices based on the germline sequence databases, while not necessarily completely homologous to the initial antibody may also be appropriate. An optional selection criteria involves checking to see which framework sequences most closely resemble the somatic mutations contained in the originating species antibody. Somatic mutations cause the sequences of antibodies to be different even if they come from the same family member. In certain embodiments it is preferable to make a selection that is closer to the somatic mutations occurring in the originating species sequence.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) may be produced by oligonucleotide synthesis and/or PCR. The nucleic acid encoding CDR regions may also be isolated from the originating species antibodies using suitable restriction enzymes and ligated into the target species framework by ligating with suitable ligation enzymes. Alternatively, the framework regions of the variable chains of the originating species antibody may be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

Assembly of a physical antibody or antibody fragment library is preferably accomplished using synthetic oligonucleotides. In one example, oligonucleotides are designed to have overlapping regions so that they could anneal and be filled in by a polymerase, such as with polymerase chain reaction (PCR). Multiple steps of overlap extension are performed in order to generate the VL and VH gene inserts. Those fragments are designed with regions of overlap with human constant domains so that they could be fused by overlap extension to produce full length light chains and Fd heavy chain fragments. The light and heavy Fd chain regions may be linked together by overlap extension to create a single Fab library insert to be cloned into a display vector. Alternative methods for the assembly of the humanized library genes can also be used. For example, the library may be assembled from overlapping oligonucleotides using a Ligase Chain Reaction (LCR) approach. See, e.g., Chalmers and Curnow, Biotechniques (2001) 30-2, p249-252.

Various forms of antibody fragments may be generated and cloned into an appropriate vector to create a hybrid antibody library or hybrid antibody fragment library. For example variable genes can be cloned into a vector that contains, in-frame, the remaining portion of the necessary constant domain. Examples of additional fragments that can be cloned include whole light chains, the Fd portion of heavy chains, or fragments that contain both light chain and heavy chain Fd coding sequence. Alternatively, the antibody fragments used for humanization may be single chain antibodies (scFv).

Any selection display system may be used in conjunction with a library according to the present disclosure. Selection protocols for isolating desired members of large libraries are known in the art, as typified by phage display techniques. Such systems, in which diverse peptide sequences are displayed on the surface of filamentous bacteriophage (Scott and Smith (1990) *Science*, 249: 386), have proven useful for creating libraries of antibody fragments (and the nucleotide sequences that encode them) for the in vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage or T7 capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward. Methods for the construction of bacteriophage antibody display libraries and lambda phage expression libraries are well known in the art (see, e.g., McCafferty et al. (1990) *Nature*, 348: 552; Kang et al. (1991) *Proc. Natl. Acad. Sci. U.S.A.*, 88: 4363).

One display approach has been the use of scFv phage-libraries (see, e.g., Huston et al., 1988, Proc. Natl. Acad. Sci U.S.A., 85: 5879-5883; Chaudhary et al. (1990) Proc. Natl. Acad. Sci U.S.A., 87: 1066-1070. Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference. The display of Fab libraries is also known, for instance as described in WO92/01047 (CAT/MRC) and WO91/17271 (Affymax).

Hybrid antibodies or hybrid antibody fragments that are cloned into a display vector can be selected against the appropriate antigen in order to identify variants that maintained good binding activity because the antibody or antibody fragment will be present on the surface of the phage or phagemid particle. See for example Barbas III, et al. (2001) Phage Display, A Laboratory Manual, Cold Spring Harbor Laboratory Press, Cold Spring Harbor, N.Y., the contents of which are incorporated herein by reference. For example, in the case of Fab fragments, the light chain and heavy chain Fd products are under the control of a lac promoter, and each chain has a leader signal fused to it in order to be directed to the periplasmic space of the bacterial host. It is in this space that the antibody fragments will be able to properly assemble. The heavy chain fragments are expressed as a fusion with a phage coat protein domain which allows the assembled antibody fragment to be incorporated into the coat of a newly made phage or phagemid particle. Generation of new phagemid particles requires the addition of helper phage which contain all the necessary phage genes. Once a library of antibody fragments is presented on the phage or phagemid surface, a process termed panning follows. This is a method whereby) the antibodies displayed on the surface of phage or phagemid particles are bound to the desired antigen, ii) non-binders are washed away, iii) bound particles are eluted from the antigen, and iv) eluted particles are exposed to fresh bacterial hosts in order to amplify the enriched pool for an additional round of selection. Typically three or four rounds of panning are performed prior to screening antibody clones for specific binding. In this way phage/phagemid particles allow the linkage of binding phenotype (antibody) with the genotype (DNA) making the use of antibody display technology very successful. However, other vector formats could be used for this humanization process, such as cloning the antibody fragment library into a lytic phage vector (modified T7 or Lambda Zap systems) for selection and/or screening.

After selection of desired hybrid antibodies and/or hybrid antibody fragments, it is contemplated that they can be produced in large volume by any technique known to those skilled in the art, e.g., prokaryotic or eukaryotic cell expression and the like. For example, hybrid antibodies or fragments may be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which may be manipulated as described herein, thereby producing a vector for the expression of a hybrid antibody heavy chain.

Additionally, an expression vector can be constructed that encodes an antibody light chain in which one or more CDRs and, if necessary, a minimal portion of the variable region framework, that are required to retain original species antibody binding specificity which may be manipulated as provided herein are derived from the originating species antibody, and the remainder of the antibody is derived from a target species immunoglobulin which can be manipulated as provided herein, thereby producing a vector for the expression of hybrid antibody light chain.

The expression vectors may then be transferred to a suitable host cell by conventional techniques to produce a transfected host cell for expression of optimized engineered antibodies or antibody fragments. The transfected or transformed host cell is then cultured using any suitable technique known to these skilled in the art to produce hybrid antibodies or hybrid antibody fragments.

In certain embodiments, host cells may be contransfected with two expression vectors, the first vector encoding a heavy chain derived polypeptide and the second encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both.

In certain embodiments, the host cell used to express hybrid antibodies or hybrid antibody fragments may be either a bacterial cell such as *Escherichia coli*, or preferably a eukaryotic cell. Preferably a mammalian cell such as a chinese hamster ovary cell or NSO cells, may be used. The choice of expression vector is dependent upon the choice of host cell, and may be selected so as to have the desired expression and regulatory characteristics in the selected host cell.

Once produced, the hybrid antibodies or hybrid antibody fragments may be purified by standard procedures of the art, including cross-flow filtration, ammonium sulphate precipitation, affinity column chromatography (e.g., protein A), gel electrophoresis and the like.

The hybrid antibodies or hybrid antibody fragments may be used in conjunction with, or attached to other proteins (or parts thereof) such as human or humanized monoclonal antibodies. These other proteins may be reactive with other markers (epitopes) characteristic for a disease against which the antibodies are directed or may have different specificities chosen, for example, to recruit molecules or cells of the target species, e.g., receptors, target proteins, diseased cells, etc. The hybrid antibodies or antibody fragments may be administered with such proteins (or parts thereof) as separately administered compositions or as a single composition with the two agents linked by conventional chemical or by molecular biological methods. Additionally the diagnostic and therapeutic value of the antibodies may be augmented by labeling the antibodies with labels that produce a detectable signal (either in vitro or in vivo) or with a label having a therapeutic property. Some labels, e.g. radionucleotides may produce a detectable signal and have a therapeutic property. Examples of radionuclide labels include $^{125}I$, $^{131}I$, $^{14}C$. Examples of other detectable labels include a fluorescent chromosphere such as green fluorescent protein, fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization.

Hybrid antibodies or hybrid antibody fragments herein may typically be administered to a patient in a composition comprising a pharmaceutical carrier. A pharmaceutical carrier can be any compatible, non-toxic substance suitable for delivery of the monoclonal antibodies to the patient, Sterile water, alcohol, fats, waxes, and inert solids may be included in the carrier. Pharmaceutically acceptable adjuvants (buffering agents, dispersing agent) may also be incorporated into the pharmaceutical composition.

The hybrid antibody or hybrid antibody fragment compositions may be administered to a patient in a variety of ways. Preferably, the pharmaceutical compositions may be administered parenterally, e.g., subcutaneously, intramuscularly or intravenously. Thus, compositions for parental administration may include a solution of the antibody, antibody fragment or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody or antibody fragment in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science*, 17$^{th}$ Ed., Mack Publishing Company, Easton, Pa. (1985), which is incorporated herein by reference.

The following examples are provided by way of illustration and should not be construed or interpreted as limiting any of the subject matter described herein.

EXAMPLE 1

A murine monoclonal antibody directed to human mannose binding lectin (the "initial antibody") was utilized in connection with the techniques described herein. The VH and VL regions were cloned and sequenced, and the individual framework regions designated FR1, FR2, FR3, and FR4 were distinguished from the CDRs using a combined Kabat/Chothia numbering system. See FIG. 4A for the variable light chain sequence of the monoclonal antibody. A BLAST search of the NCBI protein databank was conducted using each individual variable light chain framework region as a query starting with FR1. Antibody sequence gene identification number 3747016 was selected as having an FR1 with good homology to FR1 of the initial antibody light chain. See FIG. 4B. 3747016 belongs to human germline family Vκ III (see FIG. 1), either member L2 or L16, and its FR1 has 78% homology to FR1 of the initial antibody. Antibody sequence gene identification number 5833827 was selected as having an FR2 with good homology (73%) to FR2 of the initial antibody. See FIG. 4C. 5833827 belongs to family Vκ III, either members L2 or L16. Antibody sequence gene identification number 722614 was selected as having an FR3 with good homology (81%) to FR3 of the initial antibody. See FIG. 4D. 722614 belongs to family Vκ III, member L6. Antibody sequence gene identification number 1785870 was selected as having an FR4 with good homology (100%) to FR4 of the initial antibody.

The hybrid humanized variable light chain was constructed by site directed mutagenesis of the initial antibody variable light chain framework regions using the Altered Sites II in vitro Mutagenesis System commercially available from Promega Corp (Madison, Wis.). FIG. 7 depicts the respective nucleic acid and amino acid sequences of the hybrid humanized variable light chain and shows the positions of particular nucleotides and amino acids that were altered as compared to the initial antibody sequences. Framework regions are underlined and altered nucleotides and amino acids are boldface. In summary, according to the Altered Sites II system, cloning and transformation was accomplished by ligating the initial antibody VL with plasmid pALTER-EX2 (which contains the genes for chloroamphenicol and tetracycline resistance, the chloamphenicol gene containing a frameshift mutation which can be restored using the chloramphenicol repair oligonucleotide to provide selection of mutant strands). After ligation, JM109 *E. coli* cells were transformed with the plasmid, cultured, and resulting plasmids were isolated. The isolated pALTER-EX2-VL plasmids were denatured using NaOH (alkaline). Annealing and mutagenic reactions involved mixing the alkaline-denatured pALTER-EX2-VL with phosphorylated repair, knockout and mutagenic oligonucleotides (see FIG. 8), plus 10× annealing buffer (commercially available from Promega Corp.). The mixture was heated to 75° C. for 5 minutes and allowed to cool to room temperature. T4 polymerase, T4 ligase and 10× synthesis buffer was added to the annealing mixture which was incubated for 90 minutes at 37° C. to synthesize the mutant strand. The mutated product was analyzed by transforming ES1301 mutS competent cells (commercially available from Promega Corp.) with the products of the mutagenic reaction mixture. The cells suppress in vivo mismatch repair. Resulting miniprep plasmids were transformed into JM109 competent cells (commercially available from Promega Corp.). Purified plasmids from the resulting JM109 cells were screened by sequencing analysis. The resulting variable light chain contained the selected frameworks operatively linked to CDRs as shown in FIG. 4F.

FIG. 4G is a chart which shows the degree of homology between the hybrid humanized version of the initial antibody light chain (see FIG. 4F) and the light chain of the initial antibody in terms of framework regions alone (81%), CDRs alone (100%) and the whole VL chain (86%). Also shown is the degree of homology between the hybrid humanized version of the initial antibody light chain and the closest human germlne family members VκVI (A10/A26) in terms of framework regions alone (70%), CDRs alone (78%) and the Vκ chain gene (72%). Also shown is the degree of homology between a humanized light chain constructed by identifying the most similar human rearranged antibody light chain to the initial antibody framework regions and grafting the initial antibody CDRs into this light chain, i.e., human rearranged CDR grafted VL and the initial antibody light chain, is shown in terms of framework regions alone (77%), CDRs alone (100%) and the whole VL chain (83%). Finally, the degree of homology between this human rearranged CDR grafted Vλ and the closest germline family member (A14) in terms of framework regions alone (70%), CDRs alone (60%), and the Vκ chain gene (67%). As can be seen from the chart, the hybrid antibody light chain exemplified above which was made in accordance with the present disclosure demonstrates greater homology in both the framework regions and the overall variable heavy chain as compared to the comparative sequences.

FIGS. 4H and 4I show the framework homologies between the most similar antibodies in GenBank while using either the entire initial antibody light chain as a query or the combined framework regions without CDRs.

FIG. 5A shows the variable heavy chain sequence of the initial antibody. As above, a BLAST search of the NCBI protein databank was conducted using each individual variable heavy chain framework region as a query starting with FR1. Antibody sequence gene identification number 563649 was selected as having an FR1 with good homology (91%) to FR1 of the initial antibody heavy chain. See FIG. 5B. 563649 belongs to human germline family VH4, member 31 (see FIG. 2). Antibody sequence gene identification number 951263 was selected as having an FR2 with good homology (78.5%) to FR2 of the initial antibody heavy chain. See FIG. 5C. 951263 belongs to human germline family VH4, member 31. Antibody sequence gene identification number 484852 was selected as having an FR3 with good homology (81%) to FR3 of the initial antibody heavy chain. See FIG. 5D. 484852 belongs to human germline family VH4, members 4 or 31. Antibody sequence gene identification number 2367531 was selected as having an FR4 with good homology (100%) to FR4 of the initial antibody heavy chain. See FIG. 5E. 2367531 belongs to VH3, member 23.

The hybrid humanized variable heavy chain was constructed by site directed mutagenesis of the initial antibody variable heavy chain framework regions using the Altered Sites II in vitro Mutagenesis System commercially available from Promega Corp (Madison, Wis.). FIG. 7 depicts the respective nucleic acid and amino acid sequences of the hybrid humanized variable heavy chain and shows the positions of particular nucleotides and amino acids that were altered as compared to the initial antibody sequences. Framework regions are underlined and altered nucleotides and amino acids are boldface. In summary, according to the Altered Sites II system, cloning and transformation was accomplished by ligating the initial antibody VH with plasmid pALTER-EX2 (which contains the genes for chloroamphenicol and tetracycline resistance, the chloamphenicol gene containing a frameshift mutation which can be restored using the chloramphenicol repair oligonucleotide to provide selection of mutant strands). After ligation, JM109 *E. coli* cells were transformed with the plasmid, cultured, and resulting plasmids were isolated. The isolated pALTER-EX2-VH plasmids were denatured using NaOH (alkaline). Annealing and mutagenic reactions involved mixing the alkaline-denatured pALTER-EX2-VH with phosphorylated repair, knock-out and mutagenic oligonucleotides (see FIG. 8), plus 10× annealing buffer (commercially available from Promega Corp.). The mixture was heated to 75° C. for 5 minutes and allowed to cool to room temperature. T4 polymerase, T4 ligase and 10× synthesis buffer was added to the annealing mixture which was incubated for 90 minutes at 37° C. to synthesize the mutant strand. The mutated product was analyzed by transforming ES1301 mutS competent cells (commercially available from Promega Corp.) with the products of the mutagenic reaction mixture. The cells suppress in vivo mismatch repair. Resulting miniprep plasmids were transformed into JM109 competent cells (commercially available from Promega Corp.). Purified plasmids from the resulting JM109 cells were screened by sequencing analysis. The resulting variable heavy chain contained the selected frameworks operatively linked to CDRs as shown in FIG. 5F.

FIG. 5G is a chart which shows the degree of homology between the hybrid humanized version of the initial antibody heavy chain (see FIG. 5F) and the heavy chain of the initial antibody in terms of framework regions alone (86.4%), CDRs alone (100%) and the whole VH chain (90%). Also shown is the degree of homology between the hybrid humanized version of the initial antibody and the closest human germline family member VH4-31 in terms of framework regions alone (92.8%), CDRs alone (70%) and the VH chain (86.6%). Also shown is the degree of homology between the initial antibody and a humanized chain constructed by identifying the most similar human rearranged antibody heavy chain to the initial antibody framework regions and grafting the initial antibody CDRs into this heavy chain, i.e., human rearranged CDR grafted VH, is shown in terms of framework regions alone (80%), CDRs alone (100%) and the whole VH chain (86%). Finally, the degree of homology between this human rearranged CDR grafted VH and the closest germline family member (VH4-31) in terms of framework regions alone (97%), CDRs alone (70%), and the whole VH chain gene (89.6%). As can be seen from the chart, the hybrid antibody exemplified above which was made in accordance with the present disclosure demonstrates greater homology in both the framework regions and the overall variable heavy chain as compared to the comparative sequences.

FIGS. 5H and 5I show the framework homologies between the most similar antibodies in GenBank while using either the entire initial antibody light chain as a query or the combined framework regions without CDRs.

Binding affinity, association rate constant and dissociation rate constant are determined for the initial antibody and the hybrid antibody, (h3F8) prepared in accordance with this disclosure using a BIAcore 3000 system (Biacore Inc., Piscataway, N.J.) using mannan-binding lectin (MBL) as the antigen and following the manufacturer's instruction. The results are shown in FIG. 12. Two tests using the same hybrid antibody and the average thereof are shown.

EXAMPLE 2

A murine monoclonal antibody directed to h-DC-SIGN (the "initial antibody") was utilized in connection with the techniques described herein. The VH and VL regions were cloned and sequenced, and the individual framework regions designated FR1, FR2, FR3, and FR4 were distinguished from the CDRs using a combined Kabat/Chothia numbering system. See FIG. 9A for the variable light chain sequence of the monoclonal antibody. A BLAST search of the NCBI protein databank was conducted using each individual variable light chain framework region as a query starting with FR1.

FR1

Antibody sequence gene identification number 441333 was selected as having an FR1 with good homology to FR1 of the initial antibody light chain. See FIG. 9B. 441333 belongs to human germline family V$\kappa$ II (see FIG. 1), member A17 and its FR1 has 82% homology to FR1 of the initial antibody. Antibody sequence gene identification number 5578780 was selected as a second antibody having an FR1 with good homology to FR1 of the initial antibody light chain. See FIG. 9B. 5578780 belongs to human germline family V$\kappa$ II (see FIG. 1), member A3 or A9, and its FR1 has 78% homology to FR1 of the initial antibody.

FR2

Antibody sequence gene identification number 4324018 was selected as having an FR2 with good homology (86%) to FR2 of the initial antibody. See FIG. 9C. 4324018 belongs to family V$\kappa$ II, member A3. Antibody sequence gene identification number 18041766 was selected as a second antibody having an FR2 with good homology to FR2 of the initial antibody light chain. See FIG. 9B. 18041766 belongs to human germline family V$\kappa$ II (see FIG. 1), member A3 and its FR1 has 86% homology to FR1 of the initial antibody.

FR3

Antibody sequence gene identification numbers 553476 and 33251 was selected as having an FR3 with good homology (93%) to FR3 of the initial antibody. See FIG. 9D. 722614 belongs to family V$\kappa$ II, member A3.

FR4

Antibody sequence gene identification number 446245 was selected as having an FR4 with good homology (100%) to FR4 of the initial antibody. See FIG. 9E.

The hybrid humanized variable light chain was constructed by site directed mutagenesis of the initial antibody variable light chain framework regions using the Altered Sites II in vitro Mutagenesis System commercially available from Promega Corp (Madison, Wis.). FIG. 9F depicts the amino acid sequences of hybrid humanized variable light chains and shows the positions of particular amino acids that were altered as compared to the initial antibody sequences. Framework regions are boldface and altered amino acids are underlined. In summary, according to the Altered Sites II system, cloning and transformation was accomplished by ligating the initial antibody VL with plasmid pALTER-EX2 (which contains the genes for chloroamphenicol and tetracycline resistance, the chloamphenicol gene containing a frameshift mutation which can be restored using the chloramphenicol repair oligonucleotide to provide selection of mutant strands). After ligation, JM109 *E. coli* cells were transformed with the plasmid, cultured, and resulting plasmids were isolated. The isolated pALTER-EX2-VL plasmids were denatured using NaOH (alkaline). Annealing and mutagenic reactions involved mixing the alkaline-denatured pALTER-EX2-VL with phosphorylated repair, knockout and mutagenic oligonucleotides (see FIG. 8), plus 10× annealing buffer (commercially available from Promega Corp.). The mixture was heated to 75° C. for 5 minutes and allowed to cool to room temperature. T4 polymerase, T4 ligase and 10× synthesis buffer was added to the annealing mixture which was incubated for 90 minutes at 37° C. to synthesize the mutant strand. The mutated product was analyzed by transforming ES1301 mutS competent cells (commercially available from Promega Corp.) with the products of the mutagenic reaction mixture. The cells suppress in vivo mismatch repair. Resulting miniprep plasmids were transformed into JM109 competent cells (commercially available from Promega Corp.). Purified plasmids from the resulting JM109 cells were screened by sequencing analysis. The resulting variable light chain contained the selected frameworks operatively linked to CDRs as shown in FIG. 9F.

FIG. 9G is a chart which shows the degree of homology between the hybrid humanized version of the initial antibody light chain (see FIG. 9F) and the light chain of the initial antibody in terms of framework regions alone (90%), CDRs alone (100%) and the whole VL chain (93%). Also shown is the degree of homology between the hybrid humanized version of the initial antibody light chain and the closest human germline family members V$\kappa$II (A17) in terms of framework regions alone (93%), CDRs alone (70%) and the V$\kappa$ chain gene (87%). Also shown is the degree of homology between a humanized light chain constructed by identifying the most similar human rearranged antibody light chain to the initial antibody framework regions and grafting the initial antibody CDRs into this light chain, i.e., human rearranged CDR grafted VL and the initial antibody light chain, is shown in terms of framework regions alone (85%), CDRs alone (100%) and the whole VL chain (89%). The degree of homology between this human rearranged CDR grafted V$\kappa$ and the closest germline family member V$\kappa$II (A17) in terms of framework regions alone (88%), CDRs alone (70%), and the V$\kappa$ chain gene (84%). Finally, the degree of homology between the hybrid antibody including frameworks with the highest homology germline sequences to the initial antibody in terms of frameworks alone (89%), CDRs alone (100%) and whole VL chain (92%) is shown. As can be seen from the chart, the hybrid antibody light chain exemplified above which was made in accordance with the present disclosure demonstrates greater homology in both the framework regions and the overall variable heavy chain as compared to the comparative sequences.

FIG. 9H shows the framework homologies between the most similar antibodies in GenBank while using the combined framework regions without CDRs as a query.

FIG. 10A shows the variable heavy chain sequence of the initial antibody. As above, a BLAST search of the NCBI protein databank was conducted using each individual variable heavy chain framework region as a query starting with FR1.

FR1

Antibody sequence gene identification number 18698373 was selected as having an FR1 with good homology (80%) to FR1 of the initial antibody heavy chain. See FIG. 10B. 18698373 belongs to human germline family VH7, member 81 (see FIG. 2). Antibody sequence gene identification number 392677 was selected as a second antibody having an FR1 with good homology to FR1 of the initial antibody heavy chain. See FIG. 9B. 392677 belongs to human germline family VH1, member 2 (see FIG. 2), and its FR1 has 76% homology to FR1 of the initial antibody.

FR2

Antibody sequence gene identification number 886288 was selected as having an FR2 with good homology (100%) to FR2 of the initial antibody heavy chain. See FIG. 10C.

886288 belongs to human germline family VH1, member 2. Antibody sequence gene identification number 999106 was selected as a second antibody having an FR2 with good homology to FR2 of the initial antibody heavy chain. See FIG. 10B. 999106 belongs to human germline family VH1, member 46 (see FIG. 2), and its FR2 has 100% homology to FR2 of the initial antibody.

FR3

Antibody sequence gene identification number 5542538 was selected as having an FR3 with good homology (81%) to FR3 of the initial antibody heavy chain. See FIG. 10D. 5542538 belongs to human germline family VH1, member 2.

FR4

Antibody sequence gene identification number 4530559 was selected as having an FR4 with good homology (100%) to FR4 of the initial antibody heavy chain. See FIG. 10E. 4530559 belongs to VH1, member 2.

The hybrid humanized variable heavy chain was constructed by site directed mutagenesis of the initial antibody variable heavy chain framework regions using the Altered Sites II in vitro Mutagenesis System commercially available from Promega Corp (Madison, Wis.). FIG. 10F depicts the amino acid sequences of the hybrid humanized variable heavy chains and shows the positions of particular nucleotides and amino acids that were altered as compared to the initial antibody sequences. Framework regions are boldface and altered amino acids are underlined. In summary, according to the Altered Sites II system, cloning and transformation was accomplished by ligating the initial antibody VH with plasmid pALTER-EX2 (which contains the genes for chloroamphenicol and tetracycline resistance, the chloamphenicol gene containing a frameshift mutation which can be restored using the chloramphenicol repair oligonucleotide to provide selection of mutant strands). After ligation, JM109 E. coli cells were transformed with the plasmid, cultured, and resulting plasmids were isolated. The isolated pALTER-EX2-VH plasmids were denatured using NaOH (alkaline). Annealing and mutagenic reactions involved mixing the alkaline-denatured pALTER-EX2-VH with phosphorylated repair, knockout and mutagenic oligonucleotides (see FIG. 8), plus 10× annealing buffer (commercially available from Promega Corp.). The mixture was heated to 75° C. for 5 minutes and allowed to cool to room temperature. T4 polymerase, T4 ligase and 10× synthesis buffer was added to the annealing mixture which was incubated for 90 minutes at 37° C. to synthesize the mutant strand. The mutated product was analyzed by transforming ES1301 mutS competent cells (commercially available from Promega Corp.) with the products of the mutagenic reaction mixture. The cells suppress in vivo mismatch repair. Resulting miniprep plasmids were transformed into JM109 competent cells (commercially available from Promega Corp.). Purified plasmids from the resulting JM109 cells were screened by sequencing analysis. The resulting variable heavy chain contained the selected frameworks operatively linked to CDRs as shown in FIG. 10F.

FIG. 10H is a chart which shows the degree of homology between the hybrid humanized version of the initial antibody heavy chain (see FIG. 10F) and the heavy chain of the initial antibody in terms of framework regions alone (87%), CDRs alone (100%) and the whole VH chain (91%). Also shown is the degree of homology between the hybrid humanized version of the initial antibody and the closest human germline family member VH4-31 in terms of framework regions alone (72%), CDRs alone (44%) and the VH chain (64%). Also shown is the degree of homology between the initial antibody and a humanized chain constructed by identifying the most similar human rearranged antibody heavy chain to the initial antibody framework regions and grafting the initial antibody CDRs into this heavy chain, i.e., human rearranged CDR grafted VH, is shown in terms of framework regions alone (80%), CDRs alone (100%) and the whole VH chain (87%). The degree of homology between this human rearranged CDR grafted VH and the closest germline family member (VH1-46) in terms of framework regions alone (69%), CDRs alone (44%), and the whole VH chain gene (62%) is also shown. Finally, the degree of homology between the hybrid antibody having frameworks with highest homology human germline sequences versus the initial antibody in terms of frameworks alone (73%), CDRs alone (100%) and whole VH chain (81.5%) is shown. As can be seen from the chart, the hybrid antibody exemplified above which was made in accordance with the present disclosure demonstrates greater homology in both the framework regions and the overall variable heavy chain as compared to the comparative sequences.

FIG. 10G shows the framework homologies between the most similar antibodies in GenBank while using the combined framework regions without CDRs as a query.

Competition ELISA

ELISA plates were coated with 2 ug/ml Goat anti-human IgG in Carbonate coating buffer, washed twice with wash buffer. After blocking with blocking buffer at 37° C., the wells washed twice with wash buffer and then incubated with 0.25 ug/ml hDC-SIGN (in blocking buffer) for 1 hr at 37° C., washed 4 times with wash buffer.

For competition assay, either 4 ug/ml or 1 ug/ml of biotin conjugated AZN-D1 was mixed with different concentrations of AZN-D1 or a hybrid antibody in accordance with the present disclosure (hD1V1) or 5G1.1 antibody (an antibody described in U.S. Pat. No. 6,355,245, the disclosure of which is incorporated herein by this reference) in blocking buffer and incubated for 2 hrs at RT (room temperature), the wells were then washed 6 times with wash buffer, incubated with 1:1000 SA-HRP (Streptavidin-Horseradish perosidase) in blocking buffer for 45 min at RT. After washing 8 times with wash buffer, the wells were developed by OPD (o-Phenylenediamine) in 0.1M citrate-phosphate buffer, PH5.0 containing 0.03% hydrogen peroxide and read at 492 nm.

Anti-hDC-SIGN ELISA Reagents
  Carbonate Coating Buffer, pH 9.6
  $Na_2CO_3$ 1.6 g+$NaHCO_3$ 2.9 g
  Add 800 mL $H_2O$, pH to 9.6 then make to 1 L with $H_2O$
  Blocking Buffer
  BSA 1 g+PBS 100 mL
  Add BSA to PBS and allow to dissolve fully before using. Store at 4 .degree. C.
  Wash Buffer
  (0.05% Tween/PBS):Tween 20 0.5 g+PBS 1 L
  Add Tween to PBS and mix thoroughly before use
  Citrate Buffer
  Citric Acid. 2.1 g in 50 mL
  Sodium Citrate (Dihydrate) 1.47 g in 50 mL
  Add solutions together and adjust pH to 4.0-4.2

All incubations can be carried out at 4° C. overnight or at room temperature for 2 hrs OR at 37° C. for 1 hr.

The results of the competition ELISA experiments are shown in FIG. 11.

Binding affinity, association rate constant and dissociation rate constant are determined for the initial antibody and two hybrid antibodies (D1V1 and D1V2) prepared in accordance with their disclosure using h-Dc-SIGN as the antigen and following the manufacturer's instruction. The results are shown in FIG. 13.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended herein.

What is claimed is:

1. A hybrid antibody or hybrid antibody fragment comprising
   (a) complementarity determining regions (CDRs) of an initial antibody, wherein said initial antibody is specific for a target,
   (b) a first heavy chain framework region from a first antibody, the first heavy chain framework region corresponding to a particular VH germline gene family, and
   (c) a second heavy chain framework region from a second antibody, the second heavy chain framework region corresponding to the same VH germline gene family as the first heavy chain framework region,
   wherein the first and second heavy chain framework regions are selected from the group consisting of FR1, FR2 and FR3, and wherein the hybrid antibody or hybrid antibody fragment is specific for said target.

2. A hybrid antibody or hybrid antibody fragment according to claim 1 further comprising a third heavy chain framework region from an antibody selected from the group consisting of the first antibody, the second antibody and a third antibody which is neither the first nor the second antibody, the third heavy chain framework region corresponding to the same VH germline gene family as the first heavy chain framework region, wherein the third heavy chain framework region is selected from the group consisting of FR1, FR2 and FR3.

3. A hybrid antibody or hybrid antibody fragment according to claim 2 further comprising an FR4 heavy chain framework region from an antibody selected from the group consisting of the first antibody, the second antibody, the third antibody and a fourth antibody which is neither the first, the second nor the third antibody.

4. A hybrid antibody or hybrid antibody fragment according to claim 3 wherein either, or both, of the second heavy chain framework region and the third heavy chain framework region correspond to the same member of the VH germline gene family as the first heavy chain framework region.

5. A hybrid antibody or hybrid antibody fragment according to claim 1 wherein the framework regions are of human origin and the CDRs are of nonhuman origin.

6. A hybrid antibody or hybrid antibody fragment comprising
   (a) CDRs of an initial antibody, wherein said initial antibody is specific for a target,
   (b) a first light chain framework region from a first antibody, the first light chain framework region corresponding to a particular VK germline gene family, and
   (c) a second light chain framework region from a second antibody, the second light chain framework region corresponding to the same VK germline gene family as the first light chain framework region,
   wherein the first and second light chain framework regions are selected from the group consisting of FR1, FR2 and FR3, and wherein the hybrid antibody or hybrid antibody fragment is specific for said target.

7. A hybrid antibody or hybrid antibody fragment according to claim 6 further comprising a third light chain framework region from an antibody selected from the group consisting of the first antibody, the second antibody and a third antibody which is neither the first nor the second antibody, the third light chain framework region corresponding to the same VK germline gene family as the first light chain framework region, wherein the third light chain framework region is selected from the group consisting of FR1, FR2 and FR3.

8. A hybrid antibody or hybrid antibody fragment according to claim 7 further comprising an FR4 light chain framework region from an antibody selected from the group consisting of the first antibody, the second antibody, the third antibody and a fourth antibody which is neither the first, the second nor the third antibody.

9. A hybrid antibody or hybrid antibody fragment according to claim 8 wherein either, or both, of the second light chain framework region and the third light chain framework region correspond to the same member of the VK germline gene family as the first light chain framework region.

10. A hybrid antibody or hybrid antibody fragment according to claim 6 wherein the framework regions are of human origin and the CDRs are of nonhuman origin.

11. A hybrid antibody or hybrid antibody fragment comprising
   (a) CDRs of an initial antibody, wherein said initial antibody is specific for a target,
   (b) a first light chain framework region from a first antibody, the first light chain framework region corresponding to a particular VL germline gene family, and
   (c) a second light chain framework region from a second antibody, the second light chain framework region corresponding to the same VL germline gene family as the first light chain framework region,
   wherein the first and second light chain framework regions are selected from the group consisting of FR1, FR2 and FR3, and wherein the hybrid antibody or hybrid antibody fragment is specific for said target.

12. A hybrid antibody or hybrid antibody fragment according to claim 11 further comprising a third light chain framework region from an antibody selected from the group consisting of the first antibody, the second antibody and a third antibody which is neither the first nor the second antibody, the third light chain framework region corresponding to the same VL germline gene family as the first light chain framework region, wherein the third light chain framework region is selected from the group consisting of FR1, FR2 and FR3.

13. A hybrid antibody or hybrid antibody fragment according to claim 12 further comprising an FR4 light chain framework region from an antibody selected from the group consisting of the first antibody, the second antibody, the third antibody and a fourth antibody which is neither the first, the second nor the third antibody.

14. A hybrid antibody or hybrid antibody fragment according to claim 13 wherein either, or both, of the second light chain framework region and the third light chain framework region correspond to the same member of the VL germline gene family as the first light chain framework region.

15. A hybrid antibody or hybrid antibody fragment according to claim 11 wherein the framework regions are of human origin and the CDRs are of nonhuman origin.

* * * * *

UNITED STATES PATENT AND TRADEMARK OFFICE
CERTIFICATE OF CORRECTION

PATENT NO. : 7,393,648 B2  Page 1 of 1
APPLICATION NO. : 10/453698
DATED : July 1, 2008
INVENTOR(S) : Rother et al.

It is certified that error appears in the above-identified patent and that said Letters Patent is hereby corrected as shown below:

On the Title Page,

Item [*] Notice: Subject to any disclaimer, the term of this patent is extended or adjusted under 35 USC 154(b) by 462 days Delete the phrase "by 462 days" and insert -- by 757 days --

Signed and Sealed this

Twenty-seventh Day of April, 2010

David J. Kappos
*Director of the United States Patent and Trademark Office*

```
                        SEQUENCE LISTING

<160> NUMBER OF SEQ ID NOS: 196

<210> SEQ ID NO 1
<211> LENGTH: 95
<212> TYPE: PRT
<213> ORGANISM: human

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 2
<211> LENGTH: 95
<212> TYPE: PRT
<213> ORGANISM: human

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 3
<211> LENGTH: 95
<212> TYPE: PRT
<213> ORGANISM: human

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45
```

```
Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95

<210> SEQ ID NO 4
<211> LENGTH: 95
<212> TYPE: PRT
<213> ORGANISM: human

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95

<210> SEQ ID NO 5
<211> LENGTH: 95
<212> TYPE: PRT
<213> ORGANISM: human

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
                 85                  90                  95

<210> SEQ ID NO 6
<211> LENGTH: 95
<212> TYPE: PRT
<213> ORGANISM: human

<400> SEQUENCE: 6

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
```

```
                50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95

<210> SEQ ID NO 7
<211> LENGTH: 95
<212> TYPE: PRT
<213> ORGANISM: human

<400> SEQUENCE: 7

Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile Ser Asn Tyr
                20                  25                  30

Leu Ala Trp Phe Gln Gln Lys Pro Gly Lys Val Pro Lys His Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95

<210> SEQ ID NO 8
<211> LENGTH: 95
<212> TYPE: PRT
<213> ORGANISM: human

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 9
<211> LENGTH: 95
<212> TYPE: PRT
<213> ORGANISM: human

<400> SEQUENCE: 9

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 10
<211> LENGTH: 95
<212> TYPE: PRT
<213> ORGANISM: human

<400> SEQUENCE: 10

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 11
<211> LENGTH: 95
<212> TYPE: PRT
<213> ORGANISM: human

<400> SEQUENCE: 11

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 12
<211> LENGTH: 95
<212> TYPE: PRT
<213> ORGANISM: human

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 13
<211> LENGTH: 95
<212> TYPE: PRT
<213> ORGANISM: human

<400> SEQUENCE: 13

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 14
<211> LENGTH: 95
<212> TYPE: PRT
<213> ORGANISM: human

<400> SEQUENCE: 14

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Leu Gln Pro
 65                  70                  75                  80

Glu Asp Phe Ala Thr Tyr Tyr Cys Gln Gln Leu Asn Ser Tyr Pro
                 85                  90                  95

<210> SEQ ID NO 15
<211> LENGTH: 95
<212> TYPE: PRT
<213> ORGANISM: human

<400> SEQUENCE: 15

Ala Ile Arg Met Thr Gln Ser Pro Phe Ser Leu Ser Ala Ser Val Gly
 1               5                  10                  15

Asp Arg Val Thr Ile Thr Cys Trp Ala Ser Gln Gly Ile Ser Ser Tyr
             20                  25                  30

Leu Ala Trp Tyr Gln Gln Lys Pro Ala Lys Ala Pro Lys Leu Phe Ile
         35                  40                  45

Tyr Tyr Ala Ser Ser Leu Gln Ser Gly Val Pro Ser Arg Phe Ser Gly
     50                  55                  60

Ser Gly Ser Gly Thr Asp Tyr Thr Leu Thr Ile Ser Ser Leu Gln Pro
```

```
                65                  70                  75                  80
Glu Asp Phe Ala Thr Tyr Tyr Cys Gln Gln Tyr Ser Thr Pro
                    85                  90                  95

<210> SEQ ID NO 16
<211> LENGTH: 95
<212> TYPE: PRT
<213> ORGANISM: human

<400> SEQUENCE: 16

Ala Ile Arg Met Thr Gln Ser Pro Ser Phe Ser Ala Ser Thr Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Ser Tyr Pro
                    85                  90                  95

<210> SEQ ID NO 17
<211> LENGTH: 95
<212> TYPE: PRT
<213> ORGANISM: human

<400> SEQUENCE: 17

Val Ile Trp Met Thr Gln Ser Pro Ser Leu Leu Ser Ala Ser Thr Gly
 1               5                  10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                    85                  90                  95

<210> SEQ ID NO 18
<211> LENGTH: 95
<212> TYPE: PRT
<213> ORGANISM: human

<400> SEQUENCE: 18

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Asp Tyr Asn Tyr Pro
                85                  90                  95

<210> SEQ ID NO 19
<211> LENGTH: 95
<212> TYPE: PRT
<213> ORGANISM: human

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 20
<211> LENGTH: 101
<212> TYPE: PRT
<213> ORGANISM: human

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 21
<211> LENGTH: 101
<212> TYPE: PRT
<213> ORGANISM: human

<400> SEQUENCE: 21

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60
```

```
Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro
            100

<210> SEQ ID NO 22
<211> LENGTH: 100
<212> TYPE: PRT
<213> ORGANISM: human

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
            100

<210> SEQ ID NO 23
<211> LENGTH: 100
<212> TYPE: PRT
<213> ORGANISM: human

<400> SEQUENCE: 23

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
            100

<210> SEQ ID NO 24
<211> LENGTH: 100
<212> TYPE: PRT
<213> ORGANISM: human

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
```

```
                    20                  25                  30

Asp Gly Lys Thr Tyr Leu Tyr Trp Tyr Leu Gln Lys Pro Gly Gln Ser
            35                  40                  45

Pro Gln Leu Leu Ile Tyr Glu Val Ser Ser Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 25
<211> LENGTH: 100
<212> TYPE: PRT
<213> ORGANISM: human

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 26
<211> LENGTH: 100
<212> TYPE: PRT
<213> ORGANISM: human

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 27
<211> LENGTH: 106
<212> TYPE: PRT
```

<213> ORGANISM: human

<400> SEQUENCE: 27

Asp Val Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Pro Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Phe Thr Leu Ser Ile Ser Ser Val Glu Ser Glu
65                  70                  75                  80

Asp Ile Ala Asp Tyr Tyr Cys Gln Gln Thr Asn Ser Trp Pro Thr Thr
                85                  90                  95

Phe Gly Gly Gly Thr Lys Leu Glu Ile Lys
            100                 105

<210> SEQ ID NO 28
<211> LENGTH: 101
<212> TYPE: PRT
<213> ORGANISM: human

<400> SEQUENCE: 28

Asp Ile Val Met Thr Gln Thr Pro Leu Ser Pro Val Thr Leu Gly
1               5                   10                  15

Gln Pro Ala Ser Ile Ser Cys Arg Ser Ser Gln Ser Leu Val Ile Ile
            20                  25                  30

Ser Asp Gly Asn Thr Tyr Leu Ser Trp Leu Gln Arg Pro Gly Gln
        35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Thr Gln Phe Pro
            100

<210> SEQ ID NO 29
<211> LENGTH: 96
<212> TYPE: PRT
<213> ORGANISM: human

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 30
<211> LENGTH: 96
<212> TYPE: PRT
<213> ORGANISM: human

<400> SEQUENCE: 30

```
Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 31
<211> LENGTH: 95
<212> TYPE: PRT
<213> ORGANISM: human

<400> SEQUENCE: 31

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 32
<211> LENGTH: 95
<212> TYPE: PRT
<213> ORGANISM: human

<400> SEQUENCE: 32

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

```
<210> SEQ ID NO 33
<211> LENGTH: 95
<212> TYPE: PRT
<213> ORGANISM: human

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 34
<211> LENGTH: 95
<212> TYPE: PRT
<213> ORGANISM: human

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 35
<211> LENGTH: 96
<212> TYPE: PRT
<213> ORGANISM: human

<400> SEQUENCE: 35

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95
```

<210> SEQ ID NO 36
<211> LENGTH: 101
<212> TYPE: PRT
<213> ORGANISM: human

<400> SEQUENCE: 36

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro
            100

<210> SEQ ID NO 37
<211> LENGTH: 95
<212> TYPE: PRT
<213> ORGANISM: human

<400> SEQUENCE: 37

Glu Thr Thr Leu Thr Gln Ser Pro Ala Phe Met Ser Ala Thr Pro Gly
1               5                   10                  15
Asp Lys Val Asn Ile Ser Cys Lys Ala Ser Gln Asp Ile Asp Asp Asp
            20                  25                  30
Met Asn Trp Tyr Gln Gln Lys Pro Gly Glu Ala Ala Ile Phe Ile Ile
        35                  40                  45
Gln Glu Ala Thr Thr Leu Val Pro Gly Ile Pro Pro Arg Phe Ser Gly
    50                  55                  60
Ser Gly Tyr Gly Thr Asp Phe Thr Leu Thr Ile Asn Asn Ile Glu Ser
65                  70                  75                  80
Glu Asp Ala Ala Tyr Tyr Phe Cys Leu Gln His Asp Asn Phe Pro
                85                  90                  95

<210> SEQ ID NO 38
<211> LENGTH: 95
<212> TYPE: PRT
<213> ORGANISM: human

<400> SEQUENCE: 38

Glu Ile Val Leu Thr Gln Ser Pro Asp Phe Gln Ser Val Thr Pro Lys
1               5                   10                  15
Glu Lys Val Thr Ile Thr Cys Arg Ala Ser Gln Ser Ile Gly Ser Ser
            20                  25                  30
Leu His Trp Tyr Gln Gln Lys Pro Asp Gln Ser Pro Lys Leu Leu Ile
        35                  40                  45
Lys Tyr Ala Ser Gln Ser Phe Ser Gly Val Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys His Gln Ser Ser Ser Leu Pro
                85                  90                  95

```
<210> SEQ ID NO 39
<211> LENGTH: 95
<212> TYPE: PRT
<213> ORGANISM: human

<400> SEQUENCE: 39

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 40
<211> LENGTH: 95
<212> TYPE: PRT
<213> ORGANISM: human

<400> SEQUENCE: 40

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95

<210> SEQ ID NO 41
<211> LENGTH: 98
<212> TYPE: PRT
<213> ORGANISM: human

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg

<210> SEQ ID NO 42
<211> LENGTH: 98
<212> TYPE: PRT
<213> ORGANISM: human

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 43
<211> LENGTH: 98
<212> TYPE: PRT
<213> ORGANISM: human

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Arg Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 44
<211> LENGTH: 98
<212> TYPE: PRT
<213> ORGANISM: human

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr

```
                65                  70                  75                  80
Met Glu Leu Arg Ser Leu Arg Ser Asp Asp Thr Ala Val Tyr Tyr Cys
                    85                  90                  95

Ala Arg

<210> SEQ ID NO 45
<211> LENGTH: 98
<212> TYPE: PRT
<213> ORGANISM: human

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 46
<211> LENGTH: 98
<212> TYPE: PRT
<213> ORGANISM: human

<400> SEQUENCE: 46

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
            35                  40                  45

Gly Trp Ile Thr Pro Phe Asn Gly Asn Thr Asn Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 47
<211> LENGTH: 98
<212> TYPE: PRT
<213> ORGANISM: human

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45
```

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 48
<211> LENGTH: 98
<212> TYPE: PRT
<213> ORGANISM: human

<400> SEQUENCE: 48

Gln Met Gln Leu Val Gln Ser Gly Pro Glu Val Lys Lys Pro Gly Thr
 1               5                  10                  15

Ser Val Lys Val Ser Cys Lys Ala Ser Gly Phe Thr Phe Thr Ser Ser
                 20                  25                  30

Ala Val Gln Trp Val Arg Gln Ala Arg Gly Gln Arg Leu Glu Trp Ile
             35                  40                  45

Gly Trp Ile Val Val Gly Ser Gly Asn Thr Asn Tyr Ala Gln Lys Phe
            50                  55                  60

Gln Glu Arg Val Thr Ile Thr Arg Asp Met Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala

<210> SEQ ID NO 49
<211> LENGTH: 98
<212> TYPE: PRT
<213> ORGANISM: human

<400> SEQUENCE: 49

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 50
<211> LENGTH: 98
<212> TYPE: PRT
<213> ORGANISM: human

<400> SEQUENCE: 50

Gln Val Gln Leu Val Gln Ser Gly Ala Glu Val Lys Lys Pro Gly Ser
 1               5                  10                  15

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
65                   70                  75                  80

Met Glu Leu Ser Ser Leu Arg Ser Glu Asp Thr Ala Val Tyr Tyr Cys
            85                  90                  95

Ala Arg
```

<210> SEQ ID NO 51
<211> LENGTH: 98
<212> TYPE: PRT
<213> ORGANISM: human

<400> SEQUENCE: 51

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Ala Pro Gly Lys Gly Leu Glu Trp Met
            35                  40                  45

Gly Leu Val Asp Pro Glu Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
65                   70                  75                  80

Met Glu Leu Ser Ser Leu Arg Ser Glu Asp Thr Ala Val Tyr Tyr Cys
            85                  90                  95

Ala Thr
```

<210> SEQ ID NO 52
<211> LENGTH: 100
<212> TYPE: PRT
<213> ORGANISM: human

<400> SEQUENCE: 52

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
65                   70                  75                  80

Val Leu Thr Met Thr Asn Met Asp Pro Val Asp Thr Ala Thr Tyr Tyr
            85                  90                  95

Cys Ala His Arg
            100
```

<210> SEQ ID NO 53
<211> LENGTH: 100
<212> TYPE: PRT
<213> ORGANISM: human

<400> SEQUENCE: 53

Gln Val Thr Leu Lys Glu Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 54
<211> LENGTH: 100
<212> TYPE: PRT
<213> ORGANISM: human

<400> SEQUENCE: 54

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Arg Val Ser Trp Ile Arg Gln Pro Pro Gly Lys Ala Leu Glu
            35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 55
<211> LENGTH: 98
<212> TYPE: PRT
<213> ORGANISM: human

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 56
<211> LENGTH: 99
<212> TYPE: PRT
<213> ORGANISM: human

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 57
<211> LENGTH: 98
<212> TYPE: PRT
<213> ORGANISM: human

<400> SEQUENCE: 57

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 58
<211> LENGTH: 97
<212> TYPE: PRT
<213> ORGANISM: human

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu

```
                65                  70                  75                  80
Gln Met Asn Ser Leu Arg Ala Gly Asp Thr Ala Val Tyr Tyr Cys Ala
                    85                  90                  95
Arg

<210> SEQ ID NO 59
<211> LENGTH: 100
<212> TYPE: PRT
<213> ORGANISM: human

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 60
<211> LENGTH: 98
<212> TYPE: PRT
<213> ORGANISM: human

<400> SEQUENCE: 60

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 61
<211> LENGTH: 98
<212> TYPE: PRT
<213> ORGANISM: human

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
```

```
                35                  40                  45
Ser Ser Ile Ser Ser Ser Ser Tyr Ile Tyr Tyr Ala Asp Ser Val
         50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 62
<211> LENGTH: 98
<212> TYPE: PRT
<213> ORGANISM: human

<400> SEQUENCE: 62

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 63
<211> LENGTH: 98
<212> TYPE: PRT
<213> ORGANISM: human

<400> SEQUENCE: 63

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 64
<211> LENGTH: 98
<212> TYPE: PRT
<213> ORGANISM: human

<400> SEQUENCE: 64

Gln Val Gln Leu Val Glu Ser Gly Gly Gly Val Val Gln Pro Gly Arg
 1               5                  10                  15
```

```
Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 65
<211> LENGTH: 98
<212> TYPE: PRT
<213> ORGANISM: human

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 66
<211> LENGTH: 98
<212> TYPE: PRT
<213> ORGANISM: human

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 67
<211> LENGTH: 99
<212> TYPE: PRT
<213> ORGANISM: human
```

```
<400> SEQUENCE: 67

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 68
<211> LENGTH: 98
<212> TYPE: PRT
<213> ORGANISM: human

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 69
<211> LENGTH: 100
<212> TYPE: PRT
<213> ORGANISM: human

<400> SEQUENCE: 69

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100
```

<210> SEQ ID NO 70
<211> LENGTH: 97
<212> TYPE: PRT
<213> ORGANISM: human

<400> SEQUENCE: 70

Glu Val Gln Leu Val Glu Thr Gly Gly Gly Leu Ile Gln Pro Gly Gly
1               5                   10                  15
Ser Leu Arg Leu Ser Cys Ala Ala Ser Gly Phe Thr Val Ser Ser Asn
            20                  25                  30
Tyr Met Ser Trp Val Arg Gln Ala Pro Gly Lys Gly Leu Glu Trp Val
        35                  40                  45
Ser Val Ile Tyr Ser Gly Gly Ser Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg

<210> SEQ ID NO 71
<211> LENGTH: 98
<212> TYPE: PRT
<213> ORGANISM: human

<400> SEQUENCE: 71

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Tyr Val
        35                  40                  45
Ser Ala Ile Ser Ser Asn Gly Gly Ser Thr Tyr Tyr Ala Asn Ser Val
    50                  55                  60
Lys Gly Arg Phe Thr Ile Ser Arg Asp Asn Ser Lys Asn Thr Leu Tyr
65                  70                  75                  80
Leu Gln Met Gly Ser Leu Arg Ala Glu Asp Met Ala Val Tyr Tyr Cys
                85                  90                  95
Ala Arg

<210> SEQ ID NO 72
<211> LENGTH: 97
<212> TYPE: PRT
<213> ORGANISM: human

<400> SEQUENCE: 72

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser Ser Asn
            20                  25                  30
Tyr Met Ser Trp Val Arg Gln Ala Pro Gly Lys Gly Leu Glu Trp Val
        35                  40                  45
Ser Val Ile Tyr Ser Gly Gly Ser Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 73
<211> LENGTH: 100
<212> TYPE: PRT
<213> ORGANISM: human

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 74
<211> LENGTH: 100
<212> TYPE: PRT
<213> ORGANISM: human

<400> SEQUENCE: 74

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 75
<211> LENGTH: 98
<212> TYPE: PRT
<213> ORGANISM: human

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val

```
                35                  40                  45
Ser Arg Ile Asn Ser Asp Gly Ser Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 76
<211> LENGTH: 96
<212> TYPE: PRT
<213> ORGANISM: human

<400> SEQUENCE: 76

Glu Val Gln Leu Val Glu Ser Arg Gly Val Leu Val Gln Pro Gly Gly
 1               5                  10                  15

Ser Leu Arg Leu Ser Cys Ala Ala Ser Gly Phe Thr Val Ser Ser Asn
                20                  25                  30

Glu Met Ser Trp Val Arg Gln Ala Pro Gly Lys Gly Leu Glu Trp Val
                35                  40                  45

Ser Ser Ile Ser Gly Gly Ser Thr Tyr Tyr Ala Asp Ser Arg Lys Gly
 50                  55                  60

Arg Phe Thr Ile Ser Arg Asp Asn Ser Lys Asn Thr Leu His Leu Gln
 65                  70                  75                  80

Met Asn Ser Leu Arg Ala Glu Asp Thr Ala Val Tyr Tyr Cys Lys Lys
                85                  90                  95

<210> SEQ ID NO 77
<211> LENGTH: 98
<212> TYPE: PRT
<213> ORGANISM: human

<400> SEQUENCE: 77

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
                35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg

<210> SEQ ID NO 78
<211> LENGTH: 98
<212> TYPE: PRT
<213> ORGANISM: human

<400> SEQUENCE: 78

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Ser Ser Ser
```

```
                        20                  25                  30
Asn Trp Trp Gly Trp Ile Arg Gln Pro Pro Gly Lys Gly Leu Glu Trp
                35                  40                  45
Ile Gly Tyr Ile Tyr Tyr Ser Gly Ser Thr Tyr Tyr Asn Pro Ser Leu
         50                  55                  60
Lys Ser Arg Val Thr Met Ser Val Asp Thr Ser Lys Asn Gln Phe Ser
 65                  70                  75                  80
Leu Lys Leu Ser Ser Val Thr Ala Val Asp Thr Ala Val Tyr Tyr Cys
                 85                  90                  95
Ala Arg

<210> SEQ ID NO 79
<211> LENGTH: 99
<212> TYPE: PRT
<213> ORGANISM: human

<400> SEQUENCE: 79

Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
                 20                  25                  30
Gly Tyr Tyr Trp Ser Trp Ile Arg Gln His Pro Gly Lys Gly Leu Glu
                35                  40                  45
Trp Ile Gly Tyr Ile Tyr Tyr Ser Gly Ser Thr Tyr Tyr Asn Pro Ser
         50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg

<210> SEQ ID NO 80
<211> LENGTH: 99
<212> TYPE: PRT
<213> ORGANISM: human

<400> SEQUENCE: 80

Gln Leu Gln Leu Gln Glu Ser Gly Ser Gly Leu Val Lys Pro Ser Gln
 1               5                  10                  15
Thr Leu Ser Leu Thr Cys Ala Val Ser Gly Gly Ser Ile Ser Ser Gly
                 20                  25                  30
Gly Tyr Ser Trp Ser Trp Ile Arg Gln Pro Pro Gly Lys Gly Leu Glu
                35                  40                  45
Trp Ile Gly Tyr Ile Tyr His Ser Gly Ser Thr Tyr Tyr Asn Pro Ser
         50                  55                  60
Leu Lys Ser Arg Val Thr Ile Ser Val Asp Arg Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg

<210> SEQ ID NO 81
<211> LENGTH: 99
<212> TYPE: PRT
<213> ORGANISM: human

<400> SEQUENCE: 81
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 82
<211> LENGTH: 99
<212> TYPE: PRT
<213> ORGANISM: human

<400> SEQUENCE: 82

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 83
<211> LENGTH: 97
<212> TYPE: PRT
<213> ORGANISM: human

<400> SEQUENCE: 83

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 84

<211> LENGTH: 99
<212> TYPE: PRT
<213> ORGANISM: human

<400> SEQUENCE: 84

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 85
<211> LENGTH: 97
<212> TYPE: PRT
<213> ORGANISM: human

<400> SEQUENCE: 85

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 86
<211> LENGTH: 99
<212> TYPE: PRT
<213> ORGANISM: human

<400> SEQUENCE: 86

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 87
<211> LENGTH: 98
<212> TYPE: PRT
<213> ORGANISM: human

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 88
<211> LENGTH: 98
<212> TYPE: PRT
<213> ORGANISM: human

<400> SEQUENCE: 88

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 89
<211> LENGTH: 98
<212> TYPE: PRT
<213> ORGANISM: human

<400> SEQUENCE: 89

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 90
<211> LENGTH: 101
<212> TYPE: PRT
<213> ORGANISM: human

<400> SEQUENCE: 90

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 91
<211> LENGTH: 98
<212> TYPE: PRT
<213> ORGANISM: human

<400> SEQUENCE: 91

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 92
<211> LENGTH: 98
<212> TYPE: PRT
<213> ORGANISM: human

<400> SEQUENCE: 92

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30
```

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly

<210> SEQ ID NO 93
<211> LENGTH: 99
<212> TYPE: PRT
<213> ORGANISM: human

<400> SEQUENCE: 93

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly

<210> SEQ ID NO 94
<211> LENGTH: 98
<212> TYPE: PRT
<213> ORGANISM: human

<400> SEQUENCE: 94

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly

<210> SEQ ID NO 95
<211> LENGTH: 98
<212> TYPE: PRT
<213> ORGANISM: human

<400> SEQUENCE: 95

Gln Ser Val Leu Thr Gln Pro Pro Ser Ala Ser Gly Thr Pro Gly Gln
 1               5                  10                  15

-continued

```
                1               5                   10                  15

Arg Val Thr Ile Ser Cys Ser Gly Ser Ser Asn Ile Gly Ser Asn
                        20                  25                  30

Tyr Val Tyr Trp Tyr Gln Gln Leu Pro Gly Thr Ala Pro Lys Leu Leu
                        35                  40                  45

Ile Tyr Arg Asn Asn Gln Arg Pro Ser Gly Val Pro Asp Arg Phe Ser
                    50                  55                  60

Gly Ser Lys Ser Gly Thr Ser Ala Ser Leu Ala Ile Ser Gly Leu Arg
         65                 70                  75                  80

Ser Glu Asp Glu Ala Asp Tyr Tyr Cys Ala Ala Trp Asp Asp Ser Leu
                        85                  90                  95

Ser Gly
```

<210> SEQ ID NO 96
<211> LENGTH: 98
<212> TYPE: PRT
<213> ORGANISM: human

<400> SEQUENCE: 96

```
        Gln Ser Val Leu Thr Gln Pro Pro Ser Val Ser Ala Ala Pro Gly Gln
         1               5                   10                  15

Lys Val Thr Ile Ser Cys Ser Gly Ser Ser Ser Asn Ile Gly Asn Asn
                        20                  25                  30

Tyr Val Ser Trp Tyr Gln Gln Leu Pro Gly Thr Ala Pro Lys Leu Leu
                        35                  40                  45

Ile Tyr Asp Asn Asn Lys Arg Pro Ser Gly Ile Pro Asp Arg Phe Ser
                    50                  55                  60

Gly Ser Lys Ser Gly Thr Ser Ala Thr Leu Gly Ile Thr Gly Leu Gln
         65                 70                  75                  80

Thr Gly Asp Glu Ala Asp Tyr Tyr Cys Gly Thr Trp Asp Ser Ser Leu
                        85                  90                  95

Ser Ala
```

<210> SEQ ID NO 97
<211> LENGTH: 99
<212> TYPE: PRT
<213> ORGANISM: human

<400> SEQUENCE: 97

```
        Gln Ser Ala Leu Thr Gln Pro Pro Ser Ala Ser Gly Ser Pro Gly Gln
         1               5                   10                  15

Ser Val Thr Ile Ser Cys Thr Gly Thr Ser Ser Asp Val Gly Gly Tyr
                        20                  25                  30

Asn Tyr Val Ser Trp Tyr Gln Gln His Pro Gly Lys Ala Pro Lys Leu
                        35                  40                  45

Met Ile Tyr Glu Val Ser Lys Arg Pro Ser Gly Val Pro Asp Arg Phe
                    50                  55                  60

Ser Gly Ser Lys Ser Gly Asn Thr Ala Ser Leu Thr Val Ser Gly Leu
         65                 70                  75                  80

Gln Ala Glu Asp Glu Ala Asp Tyr Tyr Cys Ser Ser Tyr Ala Gly Ser
                        85                  90                  95

Asn Asn Phe
```

<210> SEQ ID NO 98
<211> LENGTH: 99
<212> TYPE: PRT

<213> ORGANISM: human

<400> SEQUENCE: 98

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Cys Ser Tyr Ala Gly Ser
                85                  90                  95

Tyr Thr Phe

<210> SEQ ID NO 99
<211> LENGTH: 99
<212> TYPE: PRT
<213> ORGANISM: human

<400> SEQUENCE: 99

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 100
<211> LENGTH: 99
<212> TYPE: PRT
<213> ORGANISM: human

<400> SEQUENCE: 100

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Leu Tyr Thr Ser Ser
                85                  90                  95

Ser Thr Phe

<210> SEQ ID NO 101
<211> LENGTH: 99
<212> TYPE: PRT
<213> ORGANISM: human

<400> SEQUENCE: 101

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe

<210> SEQ ID NO 102
<211> LENGTH: 95
<212> TYPE: PRT
<213> ORGANISM: human

<400> SEQUENCE: 102

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95

<210> SEQ ID NO 103
<211> LENGTH: 95
<212> TYPE: PRT
<213> ORGANISM: human

<400> SEQUENCE: 103

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala

<210> SEQ ID NO 104
<211> LENGTH: 96
<212> TYPE: PRT
<213> ORGANISM: human

<400> SEQUENCE: 104

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

<210> SEQ ID NO 105
<211> LENGTH: 96
<212> TYPE: PRT
<213> ORGANISM: human

<400> SEQUENCE: 105

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
            20                  25                  30

Tyr Trp Tyr Gln Gln Lys Pro Gly Gln Phe Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Ile Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Tyr
                85                  90                  95

<210> SEQ ID NO 106
<211> LENGTH: 96
<212> TYPE: PRT
<213> ORGANISM: human

<400> SEQUENCE: 106

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 107
<211> LENGTH: 96
<212> TYPE: PRT
<213> ORGANISM: human

<400> SEQUENCE: 107

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

<210> SEQ ID NO 108
<211> LENGTH: 94
<212> TYPE: PRT
<213> ORGANISM: human

<400> SEQUENCE: 108

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
                85                  90

<210> SEQ ID NO 109
<211> LENGTH: 96
<212> TYPE: PRT
<213> ORGANISM: human

<400> SEQUENCE: 109

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

<210> SEQ ID NO 110
<211> LENGTH: 94
<212> TYPE: PRT
<213> ORGANISM: human

<400> SEQUENCE: 110

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn
                85                  90

<210> SEQ ID NO 111
<211> LENGTH: 103
<212> TYPE: PRT
<213> ORGANISM: human

<400> SEQUENCE: 111

Leu Pro Val Leu Thr Gln Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 112
<211> LENGTH: 99
<212> TYPE: PRT
<213> ORGANISM: human

<400> SEQUENCE: 112

Gln Pro Val Leu Thr Gln Ser Ser Ala Ser Ala Ser Leu Gly Ser
1               5                   10                  15

Ser Val Lys Leu Thr Cys Thr Leu Ser Ser Gly His Ser Ser Tyr Ile
            20                  25                  30

Ile Ala Trp His Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Ser Gly Ser Ser Gly Ala Asp Arg Tyr Leu Thr Ile Ser
65                  70                  75                  80

Asn Leu Gln Leu Glu Asp Glu Ala Asp Tyr Tyr Cys Glu Thr Trp Asp

-continued

```
                85                  90                  95

Ser Asn Thr

<210> SEQ ID NO 113
<211> LENGTH: 99
<212> TYPE: PRT
<213> ORGANISM: human

<400> SEQUENCE: 113

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly Ile

<210> SEQ ID NO 114
<211> LENGTH: 104
<212> TYPE: PRT
<213> ORGANISM: human

<400> SEQUENCE: 114

Gln Pro Val Leu Thr Gln Pro Pro Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 115
<211> LENGTH: 104
<212> TYPE: PRT
<213> ORGANISM: human

<400> SEQUENCE: 115

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
```

```
                50                  55                  60
Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Ser Ser Ala Ser
            100

<210> SEQ ID NO 116
<211> LENGTH: 105
<212> TYPE: PRT
<213> ORGANISM: human

<400> SEQUENCE: 116

Gln Pro Val Leu Thr Gln Pro Ser Ser His Ser Ala Ser Gly Ala
 1               5                  10                  15

Ser Val Arg Leu Thr Cys Met Leu Ser Ser Gly Phe Ser Val Gly Asp
                 20                  25                  30

Phe Trp Ile Arg Trp Tyr Gln Gln Lys Pro Gly Asn Pro Pro Arg Tyr
             35                  40                  45

Leu Leu Tyr Tyr His Ser Asp Ser Asn Lys Gly Gln Gly Ser Gly Val
         50                  55                  60

Pro Ser Arg Phe Ser Gly Ser Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                 85                  90                  95

Gly Thr Trp His Ser Asn Ser Lys Thr
            100                 105

<210> SEQ ID NO 117
<211> LENGTH: 98
<212> TYPE: PRT
<213> ORGANISM: human

<400> SEQUENCE: 117

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                 20                  25                  30

Tyr Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
         50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn

<210> SEQ ID NO 118
<211> LENGTH: 98
<212> TYPE: PRT
<213> ORGANISM: human

<400> SEQUENCE: 118

Gln Thr Val Val Thr Gln Glu Pro Ser Leu Thr Val Ser Pro Gly Gly
 1               5                  10                  15
```

```
Thr Val Thr Leu Thr Cys Ala Ser Ser Thr Gly Ala Val Thr Ser Gly
             20                  25                  30

Tyr Tyr Pro Asn Trp Phe Gln Gln Lys Pro Gly Gln Ala Pro Arg Ala
         35                  40                  45

Leu Ile Tyr Ser Thr Ser Asn Lys His Ser Trp Thr Pro Ala Arg Phe
     50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Leu Leu Tyr Tyr Gly Gly
                 85                  90                  95

Ala Gln

<210> SEQ ID NO 119
<211> LENGTH: 98
<212> TYPE: PRT
<213> ORGANISM: human

<400> SEQUENCE: 119

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
             20                  25                  30

His Tyr Pro Tyr Trp Phe Gln Gln Lys Pro Gly Gln Ala Pro Arg Thr
         35                  40                  45

Leu Ile Tyr Asp Thr Ser Asn Lys His Ser Trp Thr Pro Ala Arg Phe
     50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Leu Leu Ser Tyr Ser Gly
                 85                  90                  95

Ala Arg

<210> SEQ ID NO 120
<211> LENGTH: 98
<212> TYPE: PRT
<213> ORGANISM: human

<400> SEQUENCE: 120

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
             20                  25                  30

Tyr Tyr Pro Ser Trp Tyr Gln Gln Thr Pro Gly Gln Ala Pro Arg Thr
         35                  40                  45

Leu Ile Tyr Ser Thr Asn Thr Arg Ser Ser Gly Val Pro Asp Arg Phe
     50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                 85                  90                  95

Gly Ile

<210> SEQ ID NO 121
<211> LENGTH: 104
<212> TYPE: PRT
<213> ORGANISM: human
```

-continued

```
<400> SEQUENCE: 121

Gln Pro Val Leu Thr Gln Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
            100

<210> SEQ ID NO 122
<211> LENGTH: 98
<212> TYPE: PRT
<213> ORGANISM: human

<400> SEQUENCE: 122

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala

<210> SEQ ID NO 123
<211> LENGTH: 107
<212> TYPE: PRT
<213> ORGANISM: mouse

<400> SEQUENCE: 123

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asp
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105
```

<210> SEQ ID NO 124
<211> LENGTH: 107
<212> TYPE: PRT
<213> ORGANISM: human

<400> SEQUENCE: 124

Glu Ile Val Leu Thr Gln Ser Pro Ala Thr Leu Ser Val Ser Pro Gly
1               5                   10                  15

Glu Ser Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Lys Trp Pro Arg
                85                  90                  95

Thr Phe Gly Gln Gly Thr Lys Val Glu Ile Lys
            100                 105

<210> SEQ ID NO 125
<211> LENGTH: 91
<212> TYPE: PRT
<213> ORGANISM: human

<400> SEQUENCE: 125

Leu Ser Val Ser Pro Gly Glu Arg Val Thr Phe Ser Cys Arg Ala Ser
1               5                   10                  15

Gln Thr Leu Ala Thr Asn Phe Leu Ala Trp Tyr Gln Gln Lys Ser Asp
            20                  25                  30

Gln Ala Pro Arg Leu Leu Ile Tyr Asp Ser Ser Thr Arg Ser Thr Gly
        35                  40                  45

Ile Pro Pro Arg Phe Ser Gly Thr Gly Ser Gly Thr Asp Phe Thr Leu
50                  55                  60

Thr Ile Ser Ser Leu Gln Ser Asp Asp Phe Ala Val Tyr Phe Cys Gln
65                  70                  75                  80

Gln Tyr His Asp Trp Pro Leu Thr Phe Gly Gly
                85                  90

<210> SEQ ID NO 126
<211> LENGTH: 99
<212> TYPE: PRT
<213> ORGANISM: human

<400> SEQUENCE: 126

Ala Thr Leu Ser Leu Ser Pro Gly Glu Gly Ala Thr Leu Ser Cys Arg
1               5                   10                  15

Ala Ser Gln Ser Val Asn Thr Phe Val Ala Trp Tyr Gln Gln Lys Ser
            20                  25                  30

Gly Gln Ala Pro Arg Leu Leu Ile Tyr Asp Ala Ser Lys Arg Ala Ala
        35                  40                  45

Asp Ile Pro Ser Arg Phe Ser Gly Ser Gly Ser Gly Thr Asp Phe Thr
50                  55                  60

Leu Thr Ile Ser Ser Leu Glu Pro Glu Asp Phe Gly Val Tyr Phe Cys
65                  70                  75                  80

```
Gln Gln Arg Ser Tyr Trp Pro Gln Thr Phe Gly Gln Gly Thr Lys Leu
                85                  90                  95

Glu Ile Lys
```

<210> SEQ ID NO 127
<211> LENGTH: 108
<212> TYPE: PRT
<213> ORGANISM: human

<400> SEQUENCE: 127

```
Met Ala Glu Leu Thr Gln Ser Pro Ala Thr Leu Ser Val Ser Pro Gly
1               5                   10                  15

Glu Thr Ala Ser Leu Ser Cys Arg Ala Ser Gln Ser Val Ser Asn Asn
                20                  25                  30

Leu Ala Trp Tyr Gln Gln Lys Pro Gly Gln Ala Pro Arg Leu Leu Ile
                35                  40                  45

Tyr Ala Ala Ser Thr Arg Ala Pro Gly Ile Ala Ala Arg Phe Ser Gly
            50                  55                  60

Ser Val Ser Gly Ala Asp Phe Thr Leu Thr Ile Ser Arg Leu Glu Pro
65                  70                  75                  80

Glu Asp Phe Ala Ala Tyr Phe Cys Gln Gln Tyr Gly Arg Thr Pro Leu
                85                  90                  95

Leu Thr Phe Gly Gly Gly Thr Lys Leu Glu Ile Lys
                100                 105
```

<210> SEQ ID NO 128
<211> LENGTH: 107
<212> TYPE: PRT
<213> ORGANISM: artificial sequence
<220> FEATURE:
<223> OTHER INFORMATION: hybrid humanized antibody light chain

<400> SEQUENCE: 128

```
Glu Ile Val Leu Thr Gln Ser Pro Ala Thr Leu Ser Val Ser Pro Gly
1               5                   10                  15

Glu Ser Ala Thr Leu Ser Cys Arg Ala Ser Gln Ser Ile Ser Asn Asp
                20                  25                  30

Leu His Trp Tyr Gln Gln Lys Ser Asp Gln Ala Pro Arg Leu Leu Ile
                35                  40                  45

Tyr Tyr Ala Ser Gln Ser Ile Ser Asp Ile Pro Ser Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Gly Val Tyr Phe Cys Gln Gln Ser Asn Ser Trp Pro Tyr
                85                  90                  95

Thr Phe Gly Gly Gly Thr Lys Leu Glu Ile Lys
                100                 105
```

<210> SEQ ID NO 129
<211> LENGTH: 107
<212> TYPE: PRT
<213> ORGANISM: human

<400> SEQUENCE: 129

```
Asp Val Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30
```

```
Ile His Trp Tyr Gln Gln Arg Thr Asn Gly Pro Pro Arg Leu Leu Ile
            35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Ser Ser Val Glu Ser
65                  70                  75                  80

Glu Asp Ile Ala Asp Tyr Tyr Cys Gln Gln Thr Asn Ser Trp Pro Thr
                85                  90                  95

Thr Phe Gly Gly Gly Thr Lys Leu Glu Ile Lys
            100                 105

<210> SEQ ID NO 130
<211> LENGTH: 107
<212> TYPE: PRT
<213> ORGANISM: human

<400> SEQUENCE: 130

Asp Val Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Pro Pro Arg Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Ser Ser Val Glu Ser
65                  70                  75                  80

Glu Asp Ile Ala Asp Tyr Tyr Cys Gln Gln Thr Asn Ser Trp Pro Thr
                85                  90                  95

Thr Phe Gly Gly Gly Thr Lys Leu Glu Ile Lys
            100                 105

<210> SEQ ID NO 131
<211> LENGTH: 115
<212> TYPE: PRT
<213> ORGANISM: mouse

<400> SEQUENCE: 131

Val Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Thr Ser Asp Tyr
            20                  25                  30

Ala Trp Asn Trp Ile Arg Gln Phe Pro Gly Asn Lys Leu Glu Trp Met
            35                  40                  45

Gly Tyr Ile Ser Tyr Ser Gly Ser Thr Ser Tyr Asn Pro Ser Leu Lys
    50                  55                  60

Ser Arg Val Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Trp Glu Ser Trp Phe Ala Tyr Trp Gly Gln Gly Thr Leu Val Thr
            100                 105                 110

Val Ser Ala
    115

<210> SEQ ID NO 132
<211> LENGTH: 119
```

```
<212> TYPE: PRT
<213> ORGANISM: human

<400> SEQUENCE: 132

Val Gln Leu Gln Glu Ser Gly Pro Gly Leu Val Lys Pro Ser Gln Thr
1               5                   10                  15

Leu Ser Leu Thr Cys Thr Val Ser Gly Gly Ser Ile Ser Ser Gly Arg
                20                  25                  30

Tyr Tyr Trp Ser Trp Val Arg Gln Pro Ala Gly Lys Gly Leu Glu Trp
            35                  40                  45

Ile Gly Arg Ile Tyr Ser Thr Gly Thr Thr Lys Tyr Asn Ser Ser Leu
50                  55                  60

Lys Ser Arg Ile Thr Ile Ser Val Asp Thr Ser Lys Asn Gln Phe Ser
65                  70                  75                  80

Leu Lys Leu Ser Ser Val Ile Pro Ala Asp Thr Ala Val Tyr Tyr Cys
                85                  90                  95

Ala Arg Glu Val Asp Gly Asp Tyr Ile Phe Asp Tyr Trp Gly Gln Gly
            100                 105                 110

Thr Leu Val Thr Val Ser Ser
        115

<210> SEQ ID NO 133
<211> LENGTH: 119
<212> TYPE: PRT
<213> ORGANISM: human

<400> SEQUENCE: 133

Val Gln Leu Gln Gln Trp Gly Ala Gly Leu Leu Lys Pro Ser Glu Thr
1               5                   10                  15

Leu Ser Leu Thr Cys Ala Val Ser Gly Gly Ser Phe Ser Val Asp Tyr
                20                  25                  30

Trp Ser Trp Ile Arg Gln Phe Pro Gly Lys Gly Leu Glu Trp Ile Gly
            35                  40                  45

Glu Ile Asn Asp Ser Gly Ser Thr Asn Tyr Lys Ser Ser Leu Lys Ser
50                  55                  60

Arg Val Thr Ile Ser Ile Asp Thr Ser Lys Asn Gln Phe Ser Leu Asn
65                  70                  75                  80

Leu Ser Ala Val Thr Ala Ala Asp Thr Ala Val Tyr Phe Cys Ala Arg
                85                  90                  95

Asp Arg Arg Val Gly Thr Tyr Asn Trp Phe Asp Pro Trp Gly Gln Gly
            100                 105                 110

Thr Leu Val Thr Val Ser Ser
        115

<210> SEQ ID NO 134
<211> LENGTH: 109
<212> TYPE: PRT
<213> ORGANISM: human

<400> SEQUENCE: 134

Pro Gly Leu Val Lys Pro Ser Gln Thr Leu Ser Leu Thr Cys Thr Val
1               5                   10                  15

Ser Gly Gly Ser Ile Ser Ser Gly Ser Tyr Tyr Trp Asn Trp Ile Arg
                20                  25                  30

Gln Pro Gly Gly Lys Gly Leu Glu Trp Ile Gly Arg Ile Tyr Thr Ser
            35                  40                  45

Gly Ser Thr Asn Tyr Asn Pro Ser Leu Lys Ser Arg Val Thr Ile Ser
```

```
                 50                  55                  60
Val Asp Thr Ser Lys Asn Gln Phe Ser Leu Gln Leu Asn Ser Val Thr
 65                  70                  75                  80

Pro Glu Asp Thr Ala Val Tyr Tyr Cys Ala Arg Gln Ser Asn Trp Phe
                 85                  90                  95

Asp Pro Trp Gly Gln Gly Thr Leu Val Thr Val Ser Ser
            100                 105

<210> SEQ ID NO 135
<211> LENGTH: 124
<212> TYPE: PRT
<213> ORGANISM: human

<400> SEQUENCE: 135

Val Gln Leu Leu Glu Ser Gly Gly Gly Leu Val Gln Pro Gly Gly Ser
 1               5                  10                  15

Leu Arg Leu Ser Cys Ala Ala Ser Gly Phe Thr Phe Ser Ser Tyr Ala
                 20                  25                  30

Met Asn Trp Val Arg Gln Ala Pro Gly Lys Gly Leu Glu Trp Val Ser
             35                  40                  45

Thr Ile Ser Gly Ser Gly Asp Asn Thr Ile Ile Tyr Ala Asp Ser Val
         50                  55                  60

Arg Gly Arg Phe Thr Ile Ser Arg Asp Asn Ser Lys Asn Thr Leu Ser
 65                  70                  75                  80

Leu Gln Met Asn Ser Leu Gly Ala Glu Asp Thr Ala Val Tyr Tyr Cys
                 85                  90                  95

Ala Lys Asp Leu Val Val Val Tyr Tyr Asp Ser Ser Gly Tyr Ser Ile
                100                 105                 110

Ile Trp Gly Gln Gly Thr Leu Val Thr Val Ser Ala
            115                 120

<210> SEQ ID NO 136
<211> LENGTH: 115
<212> TYPE: PRT
<213> ORGANISM: artificial sequence
<220> FEATURE:
<223> OTHER INFORMATION: hybrid humanized antibody heavy chain

<400> SEQUENCE: 136

Val Gln Leu Gln Glu Ser Gly Pro Gly Leu Val Lys Pro Ser Gln Thr
 1               5                  10                  15

Leu Ser Leu Thr Cys Thr Val Ser Gly Tyr Ser Ile Thr Ser Asp Tyr
                 20                  25                  30

Ala Trp Asn Trp Ile Arg Gln Phe Pro Gly Lys Gly Leu Glu Trp Ile
             35                  40                  45

Gly Tyr Ile Ser Tyr Ser Gly Ser Thr Ser Tyr Asn Pro Ser Leu Lys
         50                  55                  60

Ser Arg Val Thr Ile Ser Val Asp Thr Ser Lys Asn Gln Phe Ser Leu
 65                  70                  75                  80

Gln Leu Asn Ser Val Thr Pro Glu Asp Thr Ala Val Tyr Tyr Cys Ala
                 85                  90                  95

Arg Trp Glu Ser Trp Phe Ala Tyr Trp Gly Gln Gly Thr Leu Val Thr
                100                 105                 110

Val Ser Ala
    115

<210> SEQ ID NO 137
```

```
<211> LENGTH: 121
<212> TYPE: PRT
<213> ORGANISM: human

<400> SEQUENCE: 137

Val Gln Leu Gln Glu Ser Gly Pro Gly Leu Val Lys Pro Ser Gln Thr
1               5                   10                  15

Leu Ser Leu Thr Cys Thr Val Ser Gly Gly Ser Ile Ser Ser Gly Gly
            20                  25                  30

Tyr Tyr Trp Asn Trp Ile Arg Gln His Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Leu Lys Trp Gly Ser Asn His Tyr Phe Asp Tyr Trp Gly
            100                 105                 110

Gln Gly Thr Leu Val Thr Val Ser Ser
            115                 120

<210> SEQ ID NO 138
<211> LENGTH: 118
<212> TYPE: PRT
<213> ORGANISM: human

<400> SEQUENCE: 138

Val Gln Leu Gln Glu Ser Gly Pro Gly Leu Val Lys Pro Ser Gln Thr
1               5                   10                  15

Leu Ser Leu Thr Cys Thr Val Ser Gly Gly Ser Ile Ser Ser Gly Gly
            20                  25                  30

Tyr Tyr Trp Ser Trp Ile Arg Gln His Pro Gly Lys Gly Leu Glu Trp
        35                  40                  45

Ile Gly Tyr Ile Tyr Tyr Ser Ala Ser Thr Tyr Tyr Lys Gln Ser Leu
    50                  55                  60

Lys Ser Arg Val Phe Ile Ser Leu Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Cys Glu Glu Tyr Tyr Phe Asp His Trp Gly Gln Gly Thr
            100                 105                 110

Leu Val Thr Val Ser Ser
        115

<210> SEQ ID NO 139
<211> LENGTH: 17
<212> TYPE: PRT
<213> ORGANISM: human

<400> SEQUENCE: 139

Ala Glu Tyr Phe Gln His Trp Gly Gln Gly Thr Leu Val Thr Val Ser
1               5                   10                  15

Ser

<210> SEQ ID NO 140
<211> LENGTH: 17
<212> TYPE: PRT
```

```
<213> ORGANISM: human

<400> SEQUENCE: 140

Tyr Trp Tyr Phe Asp Leu Trp Gly Arg Gly Thr Leu Val Thr Val Ser
1               5                   10                  15

Ser

<210> SEQ ID NO 141
<211> LENGTH: 15
<212> TYPE: PRT
<213> ORGANISM: human

<400> SEQUENCE: 141

Ala Phe Asp Ile Trp Gly Gln Gly Thr Met Val Thr Val Ser Ser
1               5                   10                  15

<210> SEQ ID NO 142
<211> LENGTH: 15
<212> TYPE: PRT
<213> ORGANISM: human

<400> SEQUENCE: 142

Tyr Phe Asp Tyr Trp Gly Gln Gly Thr Leu Val Thr Val Ser Ser
1               5                   10                  15

<210> SEQ ID NO 143
<211> LENGTH: 16
<212> TYPE: PRT
<213> ORGANISM: human

<400> SEQUENCE: 143

Asn Trp Phe Asp Pro Trp Gly Gln Gly Thr Leu Val Thr Val Ser Ser
1               5                   10                  15

<210> SEQ ID NO 144
<211> LENGTH: 20
<212> TYPE: PRT
<213> ORGANISM: human

<400> SEQUENCE: 144

Tyr Tyr Tyr Tyr Tyr Gly Met Asp Val Trp Gly Gln Gly Thr Thr Val
1               5                   10                  15

Thr Val Ser Ser
            20

<210> SEQ ID NO 145
<211> LENGTH: 12
<212> TYPE: PRT
<213> ORGANISM: human

<400> SEQUENCE: 145

Trp Thr Phe Gly Gln Gly Thr Lys Val Glu Ile Lys
1               5                   10

<210> SEQ ID NO 146
<211> LENGTH: 12
<212> TYPE: PRT
<213> ORGANISM: human

<400> SEQUENCE: 146

Tyr Thr Phe Gly Gln Gly Thr Lys Leu Glu Ile Lys
1               5                   10
```

```
<210> SEQ ID NO 147
<211> LENGTH: 12
<212> TYPE: PRT
<213> ORGANISM: human

<400> SEQUENCE: 147

Phe Thr Phe Gly Pro Gly Thr Lys Val Asp Ile Lys
1               5                   10

<210> SEQ ID NO 148
<211> LENGTH: 12
<212> TYPE: PRT
<213> ORGANISM: human

<400> SEQUENCE: 148

Leu Thr Phe Gly Gly Gly Thr Lys Val Glu Ile Lys
1               5                   10

<210> SEQ ID NO 149
<211> LENGTH: 12
<212> TYPE: PRT
<213> ORGANISM: human

<400> SEQUENCE: 149

Ile Thr Phe Gly Gln Gly Thr Arg Leu Glu Ile Lys
1               5                   10

<210> SEQ ID NO 150
<211> LENGTH: 12
<212> TYPE: PRT
<213> ORGANISM: human

<400> SEQUENCE: 150

Tyr Val Phe Gly Thr Gly Thr Lys Val Thr Val Leu
1               5                   10

<210> SEQ ID NO 151
<211> LENGTH: 12
<212> TYPE: PRT
<213> ORGANISM: human

<400> SEQUENCE: 151

Val Val Phe Gly Gly Gly Thr Lys Leu Thr Val Leu
1               5                   10

<210> SEQ ID NO 152
<211> LENGTH: 12
<212> TYPE: PRT
<213> ORGANISM: human

<400> SEQUENCE: 152

Val Val Phe Gly Gly Gly Thr Lys Leu Thr Val Leu
1               5                   10

<210> SEQ ID NO 153
<211> LENGTH: 12
<212> TYPE: PRT
<213> ORGANISM: human

<400> SEQUENCE: 153

Ala Val Phe Gly Gly Gly Thr Gln Leu Thr Val Leu
1               5                   10

<210> SEQ ID NO 154
<211> LENGTH: 321
```

```
<212> TYPE: DNA
<213> ORGANISM: artificial sequence
<220> FEATURE:
<223> OTHER INFORMATION: hybrid antibody variable light chain

<400> SEQUENCE: 154
gaaattgtgc taactcagtc tccagccacc ctgtctgtga gtccaggaga tagcgccact    60
ctttcctgca gggccagcca agtattagc aacgacctac actggtatca acaaaaatca   120
gatcaggctc caaggcttct catctactat gcttcccagt ccatctctga tatcccctcc   180
cggttcagtg gcagtggatc agggacagat ttcactctca ctatcagcag tctggagcct   240
gaagattttg gagtgtattt ctgtcaacag agtaacagct ggccgtacac gttcggaggg   300
gggaccaagc tggaaataaa a                                              321

<210> SEQ ID NO 155
<211> LENGTH: 107
<212> TYPE: PRT
<213> ORGANISM: artificial sequence
<220> FEATURE:
<223> OTHER INFORMATION: hybrid antibody variable light chain

<400> SEQUENCE: 155

Glu Ile Val Leu Thr Gln Ser Pro Ala Thr Leu Ser Val Ser Pro Gly
1               5                   10                  15

Glu Ser Ala Thr Leu Ser Cys Arg Ala Ser Gln Ser Ile Ser Asn Asp
            20                  25                  30

Leu His Trp Tyr Gln Gln Lys Ser Asp Gln Ala Pro Arg Leu Leu Ile
        35                  40                  45

Tyr Tyr Ala Ser Gln Ser Ile Ser Asp Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Gly Val Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 156
<211> LENGTH: 348
<212> TYPE: DNA
<213> ORGANISM: artificial sequence
<220> FEATURE:
<223> OTHER INFORMATION: hybrid antibody variable heavy chain

<400> SEQUENCE: 156
gatgtgcagc ttcaggagtc gggacctggc ctggtgaaac cttctcagac tctgtccctc    60
acctgcactg tctctggcta ctcaatcacc agtgattatg cctggaactg gatccggcag   120
tttccaggaa aaggactgga gtggattggc tacataagct acagtggtag cactagctac   180
aacccatctc tcaaaagtcg agtcactatc tctgtagaca catccaagaa ccagttctcc   240
ctgcagttga attctgtgac tcctgaggac acagccgtat attactgtgc aagatgggag   300
tcctggtttg cttactgggg ccaagggact ctggtcactg tctctgca                348

<210> SEQ ID NO 157
<211> LENGTH: 116
<212> TYPE: PRT
<213> ORGANISM: artificial sequence
<220> FEATURE:
<223> OTHER INFORMATION: hybrid antibody variable heavy chain
```

<400> SEQUENCE: 157

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Tyr Asn Pro Ser Leu
    50                  55                  60

Lys Ser Arg Val Thr Ile Ser Val Asp Thr Ser Lys Asn Gln Phe Ser
65                  70                  75                  80

Leu Gln Leu Asn Ser Val Thr Pro Glu Asp Thr Ala Val Tyr Tyr Cys
                85                  90                  95

Ala Arg Trp Glu Ser Trp Phe Ala Tyr Trp Gly Gln Gly Thr Leu Val
            100                 105                 110

Thr Val Ser Ala
        115

<210> SEQ ID NO 158
<211> LENGTH: 31
<212> TYPE: DNA
<213> ORGANISM: artificial sequence
<220> FEATURE:
<223> OTHER INFORMATION: primer

<400> SEQUENCE: 158
gatataccca tgggaaattg tgctaactca g                              31

<210> SEQ ID NO 159
<211> LENGTH: 48
<212> TYPE: DNA
<213> ORGANISM: artificial sequence
<220> FEATURE:
<223> OTHER INFORMATION: primer

<400> SEQUENCE: 159
gccaccctgt ctgtgagtcc aggagatagc gccactcttt cctgcagg            48

<210> SEQ ID NO 160
<211> LENGTH: 39
<212> TYPE: DNA
<213> ORGANISM: artificial sequence
<220> FEATURE:
<223> OTHER INFORMATION: primer

<400> SEQUENCE: 160
tatcaacaaa aatcagatca ggctccaagg cttctcatc                      39

<210> SEQ ID NO 161
<211> LENGTH: 33
<212> TYPE: DNA
<213> ORGANISM: artificial sequence
<220> FEATURE:
<223> OTHER INFORMATION: primer

<400> SEQUENCE: 161
aggcttctca tctactatgc ttcccagtcc atc                            33

<210> SEQ ID NO 162
<211> LENGTH: 27
<212> TYPE: DNA

<213> ORGANISM: artificial sequence
<220> FEATURE:
<223> OTHER INFORMATION: primer

<400> SEQUENCE: 162
cagtccatct ctgatatccc ctcccgg                                27

<210> SEQ ID NO 163
<211> LENGTH: 45
<212> TYPE: DNA
<213> ORGANISM: artificial sequence
<220> FEATURE:
<223> OTHER INFORMATION: primer

<400> SEQUENCE: 163
acagatttca ctctcactat cagcagtctg gagcctgaag atttt             45

<210> SEQ ID NO 164
<211> LENGTH: 30
<212> TYPE: DNA
<213> ORGANISM: artificial sequence
<220> FEATURE:
<223> OTHER INFORMATION: primer

<400> SEQUENCE: 164
gaagattttg gagtgtattt ctgtcaacag                             30

<210> SEQ ID NO 165
<211> LENGTH: 36
<212> TYPE: DNA
<213> ORGANISM: artificial sequence
<220> FEATURE:
<223> OTHER INFORMATION: primer

<400> SEQUENCE: 165
ggcctggtga aaccttctca gactctgtcc ctcacc                      36

<210> SEQ ID NO 166
<211> LENGTH: 33
<212> TYPE: DNA
<213> ORGANISM: artificial sequence
<220> FEATURE:
<223> OTHER INFORMATION: primer

<400> SEQUENCE: 166
ctcacctgca ctgtctctgg ctactcaatc acc                         33

<210> SEQ ID NO 167
<211> LENGTH: 42
<212> TYPE: DNA
<213> ORGANISM: artificial sequence
<220> FEATURE:
<223> OTHER INFORMATION: primer

<400> SEQUENCE: 167
cagtttccag gaaaaggact ggagtggatt ggctacataa gc               42

<210> SEQ ID NO 168
<211> LENGTH: 45
<212> TYPE: DNA
<213> ORGANISM: artificial sequence
<220> FEATURE:
<223> OTHER INFORMATION: primer

<400> SEQUENCE: 168
ccatctctca aaagtcgagt cactacttct gtagacacat ccaag            45

<210> SEQ ID NO 169
<211> LENGTH: 33
<212> TYPE: DNA
<213> ORGANISM: artificial sequence
<220> FEATURE:
<223> OTHER INFORMATION: primer

<400> SEQUENCE: 169
tccaagaacc agttctccct gcagttgaat tct                        33

<210> SEQ ID NO 170
<211> LENGTH: 30
<212> TYPE: DNA
<213> ORGANISM: artificial sequence
<220> FEATURE:
<223> OTHER INFORMATION: primer

<400> SEQUENCE: 170
ttgaattctg tgactcctga ggacacagcc                            30

<210> SEQ ID NO 171
<211> LENGTH: 27
<212> TYPE: DNA
<213> ORGANISM: artificial sequence
<220> FEATURE:
<223> OTHER INFORMATION: primer

<400> SEQUENCE: 171
gaggacacag ccgtatatta ctgtgca                               27

<210> SEQ ID NO 172
<211> LENGTH: 112
<212> TYPE: PRT
<213> ORGANISM: mouse

<400> SEQUENCE: 172

Asp Val Leu Met Thr Gln Ser Pro Leu Ser Leu Pro Val Ser Leu Gly
1               5                   10                  15

Asp Lys Ala Ser Ile Ser Cys Arg Ser Ser Gln Asn Ile Val His Ser
            20                  25                  30

Asn Gly Asp Thr Tyr Leu Glu Trp Tyr Leu Gln Arg Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 173
<211> LENGTH: 113
<212> TYPE: PRT
<213> ORGANISM: human

<400> SEQUENCE: 173

Asp Val Val Met Thr Gln Ser Pro Leu Ser Leu Pro Val Thr Leu Gly
1               5                   10                  15

Gln Ser Ala Ser Ile Ser Cys Thr Ser Ser Gln Ser Leu Val Tyr Thr
            20                  25                  30

```
Asp Gly Lys Ile Tyr Leu Asn Trp Phe Gln Gln Arg Pro Gly Gln Ser
            35                  40                  45

Pro Arg Arg Leu Ile Phe Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Ala Ile Tyr Tyr Cys Met Gln Gly
                85                  90                  95

Thr His Trp Pro Gly Thr Phe Gly Gln Gly Thr Lys Val Glu Ile Lys
                100                 105                 110

Arg

<210> SEQ ID NO 174
<211> LENGTH: 112
<212> TYPE: PRT
<213> ORGANISM: human

<400> SEQUENCE: 174

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Phe Ala Trp Tyr Leu Gln Lys Pro Gly Gln Ser
            35                  40                  45

Pro Gln Leu Leu Val Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Val
                85                  90                  95

Leu Gln Thr Pro Tyr Thr Phe Gly Gln Gly Thr Lys Leu Glu Ile Ser
                100                 105                 110

<210> SEQ ID NO 175
<211> LENGTH: 101
<212> TYPE: PRT
<213> ORGANISM: human

<400> SEQUENCE: 175

Leu Pro Val Thr Pro Gly Glu Pro Ala Ser Ile Ser Cys Arg Ser Ser
 1               5                  10                  15

Gln Ser Leu Leu His Ser Asn Gly Lys Asn Tyr Leu Asp Trp Tyr Leu
                20                  25                  30

Gln Lys Pro Gly Gln Ser Pro Lys Leu Leu Ile Tyr Phe Gly Ser Thr
            35                  40                  45

Arg Ala Ser Gly Val Pro Asp Arg Phe Ser Gly Ser Gly Ser Gly Thr
 50                  55                  60

Asp Phe Thr Leu Lys Ile Ser Arg Val Glu Ala Glu Asp Val Gly Ile
 65                  70                  75                  80

Tyr Tyr Cys Met Lys Ala Gln Gln Thr Pro Ala Phe Gly Pro Gly Thr
                85                  90                  95

Lys Val Glu Ile Lys
                100

<210> SEQ ID NO 176
<211> LENGTH: 99
```

```
<212> TYPE: PRT
<213> ORGANISM: human

<400> SEQUENCE: 176

Leu Pro Val Thr Pro Gly Glu Pro Ala Ser Ile Ser Cys Arg Ser Ser
 1               5                  10                  15

Gln Ser Leu Leu Pro Gly Asn Gly Tyr Asn Tyr Leu Asp Trp Phe Leu
            20                  25                  30

Gln Arg Pro Gly Gln Ser Pro Gln Leu Leu Ile Phe Leu Thr Ser Asn
        35                  40                  45

Arg Ala Ser Gly Val Pro Asp Arg Phe Ser Gly Ser Gly Ser Gly Thr
 50                  55                  60

Asp Phe Thr Leu Lys Ile Ser Arg Val Glu Ala Glu Asp Val Gly Val
 65                  70                  75                  80

Tyr Tyr Cys Met Gln Ala Arg Gln Thr Pro Tyr Ile Phe Gly Gln Gly
                85                  90                  95

Thr Lys Leu

<210> SEQ ID NO 177
<211> LENGTH: 113
<212> TYPE: PRT
<213> ORGANISM: human

<400> SEQUENCE: 177

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Val Glu Ile Lys
            100                 105                 110

Arg

<210> SEQ ID NO 178
<211> LENGTH: 112
<212> TYPE: PRT
<213> ORGANISM: human

<400> SEQUENCE: 178

Asp Ile Val Met Thr Gln Ala Ala Phe Ser Asn Pro Val Thr Leu Gly
 1               5                  10                  15

Thr Ser Ala Ser Ile Ser Cys Arg Ser Ser Lys Asn Leu Leu His Ser
            20                  25                  30

Asn Gly Ile Thr Phe Leu Tyr Trp Tyr Leu Gln Arg Pro Gly Gln Ser
        35                  40                  45

Pro Gln Leu Leu Ile Tyr Arg Val Ser Asn Leu Ala Ser Gly Val Pro
 50                  55                  60

Asn Arg Phe Ser Gly Ser Glu Ser Gly Thr Asp Phe Thr Leu Arg Ile
 65                  70                  75                  80
```

```
Ser Arg Val Glu Ala Glu Asp Val Gly Val Tyr Tyr Cys Ala Gln Leu
                85                  90                  95

Leu Glu Leu Pro Tyr Thr Phe Gly Gly Gly Thr Lys Leu Glu Ile Lys
            100                 105                 110

<210> SEQ ID NO 179
<211> LENGTH: 112
<212> TYPE: PRT
<213> ORGANISM: artificial sequence
<220> FEATURE:
<223> OTHER INFORMATION: hybrid humanized antibody light chain

<400> SEQUENCE: 179

Asp Val Val Met Thr Gln Ser Pro Leu Ser Leu Pro Val Thr Leu Gly
1               5                   10                  15

Gln Ser Ala Ser Ile Ser Cys Arg Ser Ser Gln Asn Ile Val His Ser
            20                  25                  30

Asn Gly Asp Thr Tyr Leu Glu Trp Phe Leu Gln Arg Pro Gly Gln Ser
        35                  40                  45

Pro Gln Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 180
<211> LENGTH: 112
<212> TYPE: PRT
<213> ORGANISM: artificial sequence
<220> FEATURE:
<223> OTHER INFORMATION: hybrid humanized antibody light chain

<400> SEQUENCE: 180

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ser
            20                  25                  30

Asn Gly Asp Thr Tyr Leu Glu Trp Phe Leu Gln Arg Pro Gly Gln Ser
        35                  40                  45

Pro Gln Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 181
<211> LENGTH: 112
<212> TYPE: PRT
<213> ORGANISM: artificial sequence
<220> FEATURE:
<223> OTHER INFORMATION: hybrid humanized antibody light chain

<400> SEQUENCE: 181

Asp Val Val Met Thr Gln Ser Pro Leu Ser Leu Pro Val Thr Leu Gly
```

```
                    1               5                  10                 15
Gln Pro Ala Ser Ile Ser Cys Arg Ser Ser Gln Asn Ile Val His Ser
                20                  25                 30

Asn Gly Asp Thr Tyr Leu Glu Trp Tyr Leu Gln Lys Pro Gly Gln Ser
                35                  40             45

Pro Gln Leu Leu Ile Tyr Lys Val Ser Asn Arg Phe Ser Gly Val Pro
            50                  55              60

Asp Arg Phe Ser Gly Ser Gly Ser Gly Thr Asp Phe Thr Leu Lys Ile
65                      70              75                      80

Ser Arg Val Glu Ala Glu Asp Val Gly Val Tyr Tyr Cys Phe Gln Gly
                85                  90                 95

Ser His Val Pro Trp Thr Phe Gly Gly Gly Thr Lys Leu Glu Ile Lys
            100                 105             110

<210> SEQ ID NO 182
<211> LENGTH: 112
<212> TYPE: PRT
<213> ORGANISM: human

<400> SEQUENCE: 182

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ser
                20                  25                 30

Asn Gly Asp Thr Tyr Leu Glu Trp Tyr Leu Gln Lys Pro Gly Gln Ser
                35                  40             45

Pro Gln Leu Leu Ile Tyr Lys Val Ser Asn Arg Phe Ser Gly Val Pro
            50                  55              60

Asp Arg Phe Ser Gly Ser Gly Ser Gly Thr Asp Phe Thr Leu Lys Ile
65                      70              75                      80

Ser Arg Val Glu Ala Glu Asp Val Gly Val Tyr Tyr Cys Phe Gln Gly
                85                  90                 95

Ser His Val Pro Trp Thr Phe Gly Gly Gly Thr Lys Val Glu Ile Lys
            100                 105             110

<210> SEQ ID NO 183
<211> LENGTH: 119
<212> TYPE: PRT
<213> ORGANISM: mouse

<400> SEQUENCE: 183

Gln Val Gln Leu Gln Gln Ser Gly Pro Gln Ser Val Arg Pro Gly Ala
1               5                   10                  15

Ser Val Lys Ile Ser Cys Lys Ala Ser Gly Tyr Ser Phe Thr Ser Tyr
                20                  25                 30

Trp Met Gly Trp Val Lys Gln Arg Pro Gly Gln Gly Leu Glu Trp Ile
            35                  40              45

Gly Met Ile Asp Pro Phe Asp Ser Glu Ser Arg Leu Asn Gln Glu Phe
        50                  55              60

Lys Asp Lys Ala Thr Leu Thr Val Asp Lys Ser Ser Thr Val Tyr
65                      70              75                      80

Met Gln Leu Ser Ser Pro Thr Ser Glu Asp Ser Ala Ile Tyr Tyr Cys
                85                  90                 95

Val Arg Arg Asn Gly Gly Tyr Tyr Val Phe Asp Ser Trp Gly Gln Gly
            100                 105             110

Thr Thr Leu Thr Val Ser Ser
```

<210> SEQ ID NO 184
<211> LENGTH: 120
<212> TYPE: PRT
<213> ORGANISM: human

<400> SEQUENCE: 184

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Leu Thr Asp Tyr
            20                  25                  30

Thr Ile Asn Trp Val Arg Gln Ala Pro Gly Gln Gly Leu Glu Trp Met
        35                  40                  45

Gly Trp Ile Asn Thr Lys Thr Gly Asn Ser Thr Tyr Ala Gln Asp Phe
    50                  55                  60

Ile Gly Arg Phe Val Phe Ala Leu Asp Thr Ser Val Ser Thr Ala Tyr
65                  70                  75                  80

Leu Gln Ile Ser Ser Leu Lys Ala Glu Asp Thr Ala Leu Tyr Tyr Cys
                85                  90                  95

Ala Arg Gly Arg Tyr Ser Leu Thr Arg Phe Asp Pro Trp Gly Gln Gly
            100                 105                 110

Thr Leu Val Thr Val Ser Thr Ser
        115                 120

<210> SEQ ID NO 185
<211> LENGTH: 117
<212> TYPE: PRT
<213> ORGANISM: human

<400> SEQUENCE: 185

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Val Ser Trp Val Arg Gln Ala Pro Gly Gln Gly Leu Glu Trp Met
        35                  40                  45

Gly Trp Ile Ser Thr Ser Asp Gly Asn Thr Arg Tyr Pro Gln Lys Leu
    50                  55                  60

Gln Gly Arg Val Thr Met Thr Asp Thr Ser Ser Ser Thr Thr Tyr Met
65                  70                  75                  80

Glu Leu Arg Ser Leu Arg Pro Asp Asp Thr Ala Val Tyr Phe Cys Ala
                85                  90                  95

Arg Asp Lys Glu Pro Ala Tyr Phe Asp Tyr Trp Gly Gln Gly Thr Leu
            100                 105                 110

Val Thr Val Ser Ser
        115

<210> SEQ ID NO 186
<211> LENGTH: 117
<212> TYPE: PRT
<213> ORGANISM: human

<400> SEQUENCE: 186

Gln Val Gln Leu Leu Glu Ser Gly Ala Val Leu Ala Arg Pro Gly Thr
1               5                   10                  15

Ser Val Lys Ile Ser Cys Lys Ala Ser Gly Tyr Asn Phe Thr Ser Tyr
            20                  25                  30

```
Trp Met Leu Trp Val Lys Gln Arg Pro Gly Gln Gly Leu Glu Trp Ile
        35                  40                  45

Gly Ala Leu Phe Pro Gly Asn Ser Asp Thr Thr Tyr Lys Glu Met Leu
 50                  55                  60

Lys Gly Arg Ala Lys Leu Thr Ala Ala Thr Ser Ala Ser Ile Ala Tyr
 65                  70                  75                  80

Leu Glu Phe Ser Ser Leu Thr Asn Glu Asp Ser Ala Val Tyr Tyr Cys
                 85                  90                  95

Ala Arg Gly Asp Phe Gly Ala Met Asp Tyr Trp Gly Gln Gly Thr Leu
                100                 105                 110

Val Thr Val Ser Ser
            115

<210> SEQ ID NO 187
<211> LENGTH: 121
<212> TYPE: PRT
<213> ORGANISM: human

<400> SEQUENCE: 187

Gln Val Gln Leu Leu Glu Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
                 20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Ser Thr Ala Tyr
 65                  70                  75                  80

Met Gln Leu Ser Ser Leu Arg Ser Glu Asp Ser Ala Val Tyr Ser Cys
                 85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr
            115                 120

<210> SEQ ID NO 188
<211> LENGTH: 114
<212> TYPE: PRT
<213> ORGANISM: human

<400> SEQUENCE: 188

Gln Val Gln Leu Leu Glu Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Arg Gly Leu Glu Trp Ile
        35                  40                  45

Gly Met Ile Asp Pro Asn Ser Gly Gly Thr Lys Tyr Asn Glu Lys Phe
 50                  55                  60

Lys Ser Lys Ala Thr Leu Thr Val Asp Lys Pro Ser Asn Thr Ala Tyr
 65                  70                  75                  80

Met Gln Leu Ser Ser Leu Thr Ser Glu Asp Ser Ala Val Tyr Tyr Cys
                 85                  90                  95

Thr Arg Arg Asp Met Asp Tyr Trp Gly Ala Gly Thr Thr Val Thr Val
                100                 105                 110
```

Ser Ser

<210> SEQ ID NO 189
<211> LENGTH: 116
<212> TYPE: PRT
<213> ORGANISM: human

<400> SEQUENCE: 189

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Ser Trp Ser Trp Ile Arg Gln Ser Pro Gly Lys Gly Leu Glu Trp Ile
        35                  40                  45

Gly Glu Ile Asn His Ser Gly Ser Thr Asn Tyr Asn Ser Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Val Val Lys Gly Met Asp Val Trp Gly Gln Gly Thr Thr Leu
            100                 105                 110

Thr Val Ser Ser
        115
```

<210> SEQ ID NO 190
<211> LENGTH: 124
<212> TYPE: PRT
<213> ORGANISM: human

<400> SEQUENCE: 190

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ser Ser Gln Tyr Tyr Tyr Tyr Gly Met Asp
            100                 105                 110

Val Trp Gly Gln Gly Thr Thr Leu Thr Val Ser Ser
        115                 120
```

<210> SEQ ID NO 191
<211> LENGTH: 119
<212> TYPE: PRT
<213> ORGANISM: human

<400> SEQUENCE: 191

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                        20                  25                  30
Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Tyr Tyr Gly Met Asp Val Trp Gly Gln Gly
            100                 105                 110

Thr Thr Val Thr Val Ser Ser
        115

<210> SEQ ID NO 192
<211> LENGTH: 119
<212> TYPE: PRT
<213> ORGANISM: artificial sequence
<220> FEATURE:
<223> OTHER INFORMATION: hybrid humanized antibody heavy chain

<400> SEQUENCE: 192

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Met Ile Asp Pro Phe Asp Ser Glu Ser Arg Leu Asn Gln Glu Phe
    50                  55                  60

Lys Asp Lys Ala Thr Leu Thr Val Asp Lys Pro Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Asn Gly Gly Tyr Tyr Val Phe Asp Ser Trp Gly Gln Gly
            100                 105                 110

Thr Thr Leu Thr Val Ser Ser
        115

<210> SEQ ID NO 193
<211> LENGTH: 119
<212> TYPE: PRT
<213> ORGANISM: artificial sequence
<220> FEATURE:
<223> OTHER INFORMATION: hybrid humanized antibody heavy chain

<400> SEQUENCE: 193

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Met Ile Asp Pro Phe Asp Ser Glu Ser Arg Leu Asn Gln Glu Phe
    50                  55                  60

Lys Asp Lys Ala Thr Leu Thr Val Asp Lys Pro Ser Asn Thr Ala Tyr
65                  70                  75                  80
```

```
Met Gln Leu Ser Ser Leu Thr Ser Glu Asp Ser Ala Val Tyr Tyr Cys
            85                  90                  95

Thr Arg Arg Asn Gly Gly Tyr Tyr Val Phe Asp Ser Trp Gly Gln Gly
            100                 105                 110

Thr Thr Val Thr Val Ser Ser
        115

<210> SEQ ID NO 194
<211> LENGTH: 114
<212> TYPE: PRT
<213> ORGANISM: human

<400> SEQUENCE: 194

Gln Val Gln Leu Leu Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Met Ile Asp Pro Asn Ser Gly Gly Thr Lys Tyr Asn Glu Lys Phe
    50                  55                  60

Lys Ser Lys Ala Thr Leu Thr Val Asp Lys Pro Ser Asn Thr Ala Tyr
65                  70                  75                  80

Met Gln Leu Ser Ser Leu Thr Ser Glu Asp Ser Ala Val Tyr Tyr Cys
            85                  90                  95

Thr Arg Arg Asp Met Asp Tyr Trp Gly Ala Gly Thr Thr Val Thr Val
            100                 105                 110

Ser Ser

<210> SEQ ID NO 195
<211> LENGTH: 119
<212> TYPE: PRT
<213> ORGANISM: human

<400> SEQUENCE: 195

Gln Val Gln Leu Leu Glu Ser Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met His Trp Val Lys Gln Arg Pro Gly Arg Gly Leu Glu Trp Ile
        35                  40                  45

Gly Met Ile Asp Pro Phe Asp Ser Glu Ser Arg Leu Asn Gln Glu Phe
    50                  55                  60

Lys Asp Lys Ala Thr Leu Thr Val Asp Lys Pro Ser Asn Thr Ala Tyr
65                  70                  75                  80

Met Gln Leu Ser Ser Leu Thr Ser Glu Asp Ser Ala Val Tyr Tyr Cys
            85                  90                  95

Thr Arg Arg Asn Gly Gly Tyr Tyr Val Phe Asp Ser Trp Gly Ala Gly
            100                 105                 110

Thr Thr Val Thr Val Ser Ser
        115

<210> SEQ ID NO 196
<211> LENGTH: 119
<212> TYPE: PRT
<213> ORGANISM: artificial sequence
<220> FEATURE:
<223> OTHER INFORMATION: hybrid humanized antibody heavy chain
```

```
<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Met
        35                  40                  45

Gly Met Ile Asp Pro Phe Asp Ser Glu Ser Arg Leu Asn Gln Glu Phe
        50              55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asn Gly Gly Tyr Tyr Val Phe Asp Ser Trp Gly Gln Gly
            100                 105                 110

Thr Thr Val Thr Val Ser Ser
            115
```